(12) United States Patent
Georgopoulos et al.

(10) Patent No.: US 10,106,834 B2
(45) Date of Patent: Oct. 23, 2018

(54) METHODS OF DIAGNOSING AND TREATING B CELL ACUTE LYMPHOBLASTIC LEUKEMIA

(71) Applicants: The General Hospital Corporation, Boston, MA (US); Tufts Medical Center, Inc., Boston, MA (US)

(72) Inventors: Katia Georgopoulos, Lexington, MA (US); Richard A. Etten, Laguna Beach, CA (US); Ila Joshi, Malden, MA (US)

(73) Assignees: The General Hospital Corporation, Boston, MA (US); Tufts Medical Center, Inc., Boston, MA (US)

(*) Notice: Subject to any disclaimer, the term of this patent is extended or adjusted under 35 U.S.C. 154(b) by 0 days.

(21) Appl. No.: 15/028,515

(22) PCT Filed: Oct. 9, 2014

(86) PCT No.: PCT/US2014/059870
§ 371 (c)(1),
(2) Date: Apr. 11, 2016

(87) PCT Pub. No.: WO2015/054477
PCT Pub. Date: Apr. 16, 2015

(65) Prior Publication Data
US 2016/0251696 A1    Sep. 1, 2016

Related U.S. Application Data

(60) Provisional application No. 61/927,397, filed on Jan. 14, 2014, provisional application No. 61/888,538, filed on Oct. 9, 2013.

(51) Int. Cl.
*A61K 31/506* (2006.01)
*A61K 31/7088* (2006.01)
*A61K 31/713* (2006.01)
*C12Q 1/48* (2006.01)
*G01N 33/574* (2006.01)
*A61K 45/06* (2006.01)
*G01N 33/50* (2006.01)

(52) U.S. Cl.
CPC ............ *C12Q 1/485* (2013.01); *A61K 31/506* (2013.01); *A61K 31/7088* (2013.01); *A61K 31/713* (2013.01); *A61K 45/06* (2013.01); *G01N 33/5011* (2013.01); *G01N 33/57426* (2013.01); *G01N 2333/912* (2013.01); *G01N 2800/52* (2013.01); *G01N 2800/54* (2013.01); *G01N 2800/7028* (2013.01)

(58) Field of Classification Search
CPC .............. A61K 31/506; A61K 31/7088; A61K 31/713; A61K 45/06
See application file for complete search history.

(56) References Cited

U.S. PATENT DOCUMENTS

| | | |
|---|---|---|
| 2010/0249152 A1 | 9/2010 | Schenone et al. |
| 2013/0017194 A1 | 1/2013 | Holmes et al. |
| 2013/0158005 A1 | 6/2013 | Heinrich et al. |
| 2013/0345091 A1 | 9/2013 | Rozema et al. |
| 2013/0324532 A1 | 12/2013 | Holmes et al. |
| 2013/0324546 A1 | 12/2013 | Holmes et al. |

FOREIGN PATENT DOCUMENTS

| | | |
|---|---|---|
| EP | 2190834 | 6/2010 |
| WO | WO2005014835 | 2/2005 |
| WO | WO 2008115369 | 9/2008 |
| WO | WO2010062578 | 6/2010 |
| WO | 2011/133668 | 10/2011 |
| WO | WO2012045194 | 4/2012 |
| WO | WO 2012110774 | 8/2012 |

OTHER PUBLICATIONS

International Search Report and Written Opinion dated Feb. 4, 2015 in international application No. PCT/US2014/059870, 17 pgs.
Le et al., "FAK silencing inhibits leukemogenesis in BCR/ABL-transformed hematopoietic cells," Am. J. Hematol. 84(5): 273-278 (May 2009).
Iacobucci et al., "Expression of spliced oncogenic Ikaros isoforms in Philadelphia-positive acute lymphoblastic leukemia patients treated with tyrosine kinase inhibitors: implications for a new mechanism of resistance," Blood 112(9): 3847-3855 (Nov. 2011).
Crompton et al., "High-Throughput Tyrosine Kinase Activity Profiling Identifies FAK as a Candidate Therapeutic Target in Ewing Sarcoma," Cancer Res ePub 73(9): 2873-2883 (Mar. 27, 2013).
Despeaux et al., "Focal adhesion kinase splice variants maintain primitive acute myeloid leukemia cells through altered Wnt signaling," Stem Cells 30(8): 1597-1610 (Aug. 2012).
Bernardi et al., "Lymphoid precursor cells adhere to two different sites on fibronectin," J Cell Biol, Jul. 1987, 105: 489-498.
Beviglia et al., "Focal adhesion kinase N-terminus in breast carcinoma cells induces rounding, detachment and apoptosis," Biochem J., 2003, 373:201-210.
Bryant et al., "Focal adhesion kinase is a phospho-regulated repressor of Rac and proliferation in human endothelial cells," Biol Open., Aug. 15, 2012, 1(8):723-30.
Cheng et al., "Syk tyrosine kinase required for mouse viability and B-cell development," Nature, Nov. 16, 1995, 378(6554): 303-306.
Chessells, "Pitfalls in the diagnosis of childhood leukaemia," British Journal of Haematology, Sep. 2001, 114 (3): 506-511.
Choi et al. "Actin and alpha-actinin orchestrate the assembly and maturation of nascent adhesions in a myosin II motor-independent manner," Nature Cell Biology, 2008, 10:1039-1050.
Cobaleda et al., "I. B-cell acute lymphoblastic leukaemia: towards understanding its cellular origin," Bioessays, Jun. 2009, 31(6): 600-609.
Cortes et al., "The value of high-dose systemic chemotherapy and intrathecal therapy for central nervous system prophylaxis in different risk groups of adult acute lymphoblastic leukemia," Blood, Sep. 15, 1995, 86(6):2091-7.

(Continued)

*Primary Examiner* — Sahar Javanmard
(74) *Attorney, Agent, or Firm* — Fish & Richardson P.C.

(57) ABSTRACT

Methods for the diagnosis and treatment of B cell Acute Lymphoblastic Leukemia (B-ALL), based in part on the detection and/or inhibition of Focal Adhesion Kinase (FAK), e.g., phosphorylated FAK (pFAK).

9 Claims, 36 Drawing Sheets
Specification includes a Sequence Listing.

(56) References Cited

OTHER PUBLICATIONS

Dunn et al., "Evolving Therapies and FAK Inhibitors for the Treatment of Cancer," Anticancer Agents Med Chem., Dec. 2010, 10(10): 722-734.
Fleming et al., "Pre-B cell receptor signaling mediates selective response to IL-7 at the pro-B to pre-B cell transition via an ERK/MAP kinase-dependent pathway," Immunity, Oct. 2001, 15: 521-531.
Furqan et al., "Dysregulation of JAK-STAT pathway in hematological malignancies and JAK inhibitors for clinical application," Biomarker Research, Jan. 16, 2013, 1(1):5.
Fuxa et al, "Pax5 induces V-to-DJ rearrangements and locus contraction of the immunoglobulin heavy-chain gene," Genes & Dev, 2004, 18:411-422.
Galbraith et al., "Polymerizing actin fibers position integrins primed to probe for adhesion sites," Science, Feb. 16, 2007, 315: 992-995.
Gauld and Cambier, "Src-family kinases in B-cell development and signaling," Oncogene, 2004, 23: 8001-8006.
Georgopoulos, "Acute Lymphoblastic Leukemia—On the Wings of IKAROS," N Engl J Med, Jan. 29, 2009, 360(5): 524-526.
Georgopoulos et al, "The Ikaros gene is required for the development of all lymphoid lineages," Cell, Oct. 7, 1994, 79: 143-156.
Glodek et al., "Focal adhesion kinase is required for CXCL12-induced chemotactic and pro-adhesive responses in hematopoietic precursor cells," Leukemia, 2007, 21: 1723-1732.
Golubovskaya et al., "The direct effect of Focal Adhesion Kinase (FAK), dominant-negative FAK, FAK-CD and FAK siRNA on gene expression and human MCF-7 breast cancer cell tumorigenesis," BMC Cancer, Aug. 12, 2009, 9:280.
Golubovskaya et al., "A small molecule inhibitor, 1,2,4,5-benzenetetraamine tetrahydrochloride, targeting the y397 site of focal adhesion kinase decreases tumor growth," J Med Chem, Dec. 2008, 51(23): 7405-16.
Gong et al., "Regulation of an early developmental checkpoint in the B cell pathway by lg beta," Science, Apr. 19, 1996, 272(5260): 411-414.
Halder et al., "Focal adhesion kinase silencing augments docetaxel-mediated apoptosis in ovarian cancer cells," Clin. Cancer Res., Dec. 15, 2005, 11: 8829-8836.
Harvey et al., "Identification of novel cluster groups in pediatric high-risk B-precursor acute lymphoblastic leukemia with gene expression profiling: correlation with genome-wide DNA copy number alterations, clinical characteristics, and outcome," Blood, Dec. 2010, 116(23): 4874-4884.
Hayashi et al., "Stepwise progression of B lineage differentiation supported by interleukin 7 and other stromal cell molecules," J Exp Med, May 1990, 171: 1683-1695.
Heasman and Ridley, "Mammalian Rho GTPases: new insights into their functions from in vivo studies," Nat Rev Mol Cell Biol,, Sep. 2008, 9(9): 690-701.
Heerema-McKenny et al., "Pathology and molecular diagnosis of leukemias and lymphomas." In: Pizzo PA, Poplack DG, eds.: Principles and Practice of Pediatric Oncology. 6th ed. Philadelphia, Pa: Lippincott Williams and Wilkins, 2011, pp. 138-163.
Herzog et al., "SLP-65 regulates immunoglobulin light chain gene recombination through the PI(3)K-PKB-Foxo pathway," Nat Immunol, Jun. 2008, 9: 623-631.
Herzog et al., "Regulation of B-cell proliferation and differentiation by pre-B-cell receptor signaling," Nat Rev Immunol,, Mar. 2009, 9:195-205.
Hoelzer and Gale, "Acute lymphoblastic leukemia in adults: recent progress, future directions," Seminars in Hematology, 1987, 24 (1): 27-39.
Iacobucci et al., "Identification and molecular characterization of recurrent genomic deletions on 7p12 in the IKZF1 gene in a large cohort of BCR-ABL1-positive acute lymphoblastic leukemia patients: on behalf of Gruppo Italiano Malattie Ematologiche dell'Adulto Acute Leukemia Working Party (GIMEMA AL WP)," Blood, Sep. 3, 2009,114(10): 2159-2167.

International Preliminary Report on Patentability in International Application No. PCT/USA2014/059870, dated Apr. 12, 2016, 10 pages.
Irwin et al., "Small Molecule ErbB Inhibitors Decrease Proliferative Signaling and Promote Apoptosis in Philadelphia Chromosome-Positive Acute Lymphoblastic Leukemia," PLOS One, Aug. 2013, 8(8):e70608.
Johnson et al., "Regulation of immunoglobulin light-chain recombination by the transcription factor IRF-4 and the attenuation of interleukin-7 Signaling," Immunity, 2008, 28, 335-345.
Kantarjian et al., "Long-term follow-up results of hyperfractionated cyclophosphamide, vincristine, doxorubicin, and dexamethasone (Hyper-CVAD), a dose-intensive regimen, in adult acute lymphocytic leukemia," Cancer. Dec. 15, 2004;101(12):2788-801.
Kersseboom et al., "Bruton's tyrosine kinase cooperates with the B cell linker protein SLP-65 as a tumor suppressor in Pre-B cells," J Exp Med., Jul. 7, 2003, 198(1): 91-98.
Kierny and Dorshkind, "B lymphocyte precursors and myeloid progenitors survive in diffusion chamber cultures but B cell differentiation requires close association with stromal cells," Blood, Nov. 1987, 70(5): 1418-1424.
Kitamura et al., "A critical role of lambda 5 protein in B cell development," Cell, May 1992, 69(5): 823-831.
Kraus et al., "Interference with immunoglobulin (Ig)alpha immunoreceptor tyrosine-based activation motif (ITAM) phosphorylation modulates or blocks B cell development, depending on the availability of an Igbeta cytoplasmic tail," J Exp Med, Aug. 20, 2001, 194(4): 455-469.
Kuiper et al., "IKZF1 deletions predict relapse in uniformly treated pediatric precursor B-ALL," Leukemia, 2010, 24(7):1258-1264.
Kurenova et al., "The FAK scaffold inhibitor C4 disrupts FAK-VEGFR-3 signaling and inhibits pancreatic cancer growth," Oncotarget, Oct. 2013, 4(10): 1632-1646.
Larson et al., "A five-drug remission induction regimen with intensive consolidation for adults with acute lymphoblastic leukemia: cancer and leukemia group B study 8811," Blood, Apr. 15, 1995, 85(8):2025-37.
Ma et al., "Focal adhesion kinase (FAK) inhibition as a potential strategy for anticancer therapies," Drugs Fut, 2009, 34(6): 477.
Ma, "Development of focal adhesion kinase inhibitors in cancer therapy," Anticancer Agents Med Chem., Sep. 2011, 11(7):638-42.
Malin et al, "Role of STAT5 in controlling cell survival and immunoglobulin gene recombination during pro-B cell development," Nat Immunol, 2010, 11: 171-179.
Margolin et al., "Acute lymphoblastic leukemia." Principles and Practice of Pediatric Oncology, 6th ed., 2011, 518-65.
Marshall et al., "Modulation of the IL-7 dose-response threshold during pro-B cell differentiation is dependent on pre-B cell receptor expression," J Immunol, 1998, 161: 6038-6045.
Martinelli et al., "IKZF1 (Ikaros) Deletions in BCR-ABL1-Positive Acute Lymphoblastic Leukemia Are Associated With Short Disease-Free Survival and High Rate of Cumulative Incidence of Relapse: A GIMEMA AL WP Report," J Clin Oncol., Nov. 1, 2009, 27(31):5202-5207.
Middendorp et al., "Tumor suppressor function of Bruton tyrosine kinase is independent of its catalytic activity," Blood, 2005, 105: 259-265.
Monroe, "IT AM-mediated tonic signalling through pre-BCR and BCR complexes," Nat Rev Immunol, Apr. 2006, 6(4): 283-294.
Morgan et al., "Aiolos, a lymphoid restricted transcription factor that interacts with Ikaros to regulate lymphocyte differentiation," Embo J, 1997, 16: 2004-2013.
Mullighan et al., "Deletion of IKZF1 and Prognosis in Acute Lymphoblastic Leukemia," N Engl J Med., Jan. 2009, 360(5):470-480.
Mullighan et al., "BCR-ABL1 lymphoblastic leukaemia is characterized by the deletion of Ikaros," Nature, May 1, 2008, 453(7191):110-114.
Mullighan et al., "Genome-wide analysis of genetic alterations in acute lymphoblastic leukaemia," 2007, Nature 446, 758-764.
Mullighan, "Molecular genetics of B-precursor acute lymphoblastic leukemia," J Clin Invest, Oct. 2012, 122(10):3407-3415.

(56) References Cited

OTHER PUBLICATIONS

Ng et al., "Genome-wide lineage-specific transcriptional networks underscore Ikaros-dependent lymphoid priming in hematopoietic stem cells," Immunity, Apr. 17, 2009, 30(4): 493-507.
Ochiai et al.' "A self-reinforcing regulatory network triggered by limiting IL-7 activates pre-BCR signaling and differentiation," Nat Inimunol, Mar. 2012, 13(3): 300-307.
Onciu, "Acute Lymphoblastic Leukemia," Hematol Oncol Clin North Am, 2009, 23(4): 655-74.
Osmond et al., "Pre-B cells in mouse bone marrow: in vitro maturation of peanut agglutinin binding B lymphocyte precursors separated from bone marrow by fluorescence-activated cell sorting," J Immunol, Jul. 1984, 133(1): 86-90.
Papaemmanuil et al., "Loci on 7p12.2, 10q21.2 and 14q11.2 are associated with risk of childhood acute lymphoblastic leukemia," Nat Genetics, Sep. 2009, 41(9):1006-1010.
Park et al., "Focal adhesion kinase regulates the localization and retention of pro-B cells in bone marrow microenvironments," J Immunol, Dec. 12, 2012, 190: 1094-1102.
Pelanda et al, "B cell progenitors are arrested in maturation but have intact VDJ recombination in the absence ofIg-alpha and Ig-beta," J Immunol, 2002, 169, 865-872.
Pelanda et al., "A prematurely expressed Ig(kappa) transgene, but not V(kappa)J(kappa) gene segment targeted into the Ig(kappa) locus, can rescue B cell development in lambda5-deficient mice," Immunity, Sep. 1996, 5: 229-239.
Radi et al., "Discovery and SAR of 1,3,4-thiadiazole derivatives as potent Abl tyrosine kinase inhibitors and cytodifferentiating agents," Bioorg Med Chem Lett, 2008, 18(3):1207-1211.
Roberts et al., "Antitumor Activity and Pharmacology of a Selective Focal Adhesion Kinase Inhibitor, PF-562,271," Cancer Res., 2008, 68: 1935-44.
Rolink et al., "The c-kit-encoded tyrosine kinase regulates the proliferation of early pre-B cells," Eur J Immunol, Oct. 1991, 21(10): 2609-2612.
Rolink et al., "Precursor B cell receptor-dependent B cell proliferation and differentiation does not require the bone marrow or fetal liver environment," J Exp Med, Jan. 1, 2000, 191(1): 23-32.
Roumiantsev et al., "The src homology 2 domain ofBcr/Abl is required for efficient induction of chronic myeloid leukemia-like disease in mice but not for lymphoid leukemogenesis or activation of phosphatidylinositol 3-kinase," Blood, Jan. 1, 2001, 97(1): 4-13.
Rowe et al., "Induction therapy for adults with acute lymphoblastic leukemia: results of more than 1500 patients from the international ALL trial: MRC UKALL XII/ECOG E2993," Blood, Dec. 1, 2005, 106(12):3760-7.
Saijo et al., "Essential role of Src-family protein tyrosine kinases in NF-kappaB activation during B cell development," Nat Immunol, 2003, 4: 274-279.
Schlissel et al., "Virus-transformed pre-B cells show ordered activation but not inactivation of imrnunoglobulin gene rearrangement and transcription," J Exp Med, Mar. 1991, 173: 711-720.
Schultze and Fiedler, "Clinical importance and potential use of small molecule inhibitors of focal adhesion kinase," Anticancer Agents Med Chem., Sep. 2011, 11(7):593-9.
Schweighoffer et al., "Unexpected requirement for ZAP-70 in pre-B cell development and allelic exclusion," Immunity, Apr. 2003, 18: 523-533.
Schwock et al., "Targeting focal adhesion kinase with dominant-negative FRNK or Hsp90 inhibitor 17-DMAG suppresses tumor growth and metastasis of SiHa cervical xenografts," Cancer Res., Jun. 2009, 69(11):4750-9.
Seiter et al., "Acute Lymphoblastic Leukemia Treatment Protocol," Medline, 2013 available at emedicine.medscape.com/article/2004705-overview.
Shi et al., "A novel low-molecular weight inhibitor of focal adhesion kinase, TAE226, inhibits glioma growth," Mol Carcinog, Jun. 2007, 46:488-96.
Shiotsu et al., "KW-2449, a novel multikinase inhibitor, suppresses the growth of leukemia cells with FLT3 mutations or T315I-mutated BCR/ABL translocation," Blood, Aug. 20, 2009, 114(8):1607-17.
Slack-Davis et al., "Cellular characterization of a novel focal adhesion kinase inhibitor," J Biol Chem, May 18, 2007, 282(20):14845-52.
Smith et al., Effect of focal adhesion kinase (FAK) downregulation with FAK antisense oligonucleotides and 5-fluorouracil on the viability of melanoma cell lines, Oct. 2005, Melanoma Res., 15(5):357-362.
Smith et al., "A talin-dependent LFA-1 focal zone is formed by rapidly migrating T lymphocytes," J Cell Biol ,Jul. 4, 2005, 170(1): 141-151.
Stokes et al., "Inhibition of focal adhesion kinase by PF-562,271 inhibits the growth and metastasis of pancreatic cancer concomitant with altering the tumor microenvironment," Mol Cancer Ther., Nov. 2011, 10(1 1):2135-45.
Sudo et al., "Expression and function of the interleukin 7 receptor in murine lymphocytes," PNAS, Oct. 1993, 90: 9125-9129.
Sun et al., "Zinc finger-mediated protein interactions modulate Ikaros activity, a molecular control oflymphocyte development," Embo J, 1996, 15(19): 5358-5369.
Thomas et al., "Outcome of treatment in adults with acute lymphoblastic leukemia: analysis of the LALA-94 trial," J Clin Oncol., Oct. 15, 2004, 22(20):4075-86.
Thompson et al., "Ikaros DNA-binding proteins as integral components of B cell developmental-stage-specific regulatory circuits," Immunity, Mar. 2007, 26: 335-344.
Tse et al., "B cell receptor-induced phosphorylation of Pyk2 and focal adhesion kinase involves integrins and the Rap GTPases and is required for B cell spreading," J Biol Chem, Aug. 21, 2009, 284: 22865-22877.
Vicente-Manzanares et al., "Integrins in cell migration—the actin connection," J Cell Sci., 2009, 122: 199-206.
Virely et al., "Haploinsufficiency of the IKZF1 (IKAROS) tumor suppressor gene cooperates with BCR-ABL in a transgenic model of acute lymphoblastic leukemia," Leukemia, Jun. 2010, 24(6):1200-1204.
Waanders et al. "Integrated use of minimal residual disease classification and IKZF 1 alteration status accurately predicts 79% of relapses in pediatric acute lyrnphoblastic leukemia," Leukemia, 25: 254-258 (2011.
Wehrle-Haller, "Structure and function of focal adhesions," Curr Opin Cell Biol, Feb. 2012, 24(1): 116-124.
Wen et al., "Essential role of phospholipase C gamma 2 in early Bcell development and Myc-mediated lymphomagenesis," Mol Cell Biol, Dec. 2006, 26: 9364-9376.
Winandy et al., "A dominant mutation in the Ikaros gene leads to rapid development of leukemia and lymphoma," Cell, Oct. 1995, 83: 289-299.
Yasuda et al., "Erk kinases link pre-B cell receptor signaling to transcriptional events required for early B cell expansion," Apr. 2008, Immunity, 28: 499-508.
Ye et al., "Reconstruction of integrin activation," Jan. 2012, Blood 119(1): 26-33.
Yoshida et al., "Early hematopoietic lineage restrictions directed by Ikaros," Nat Immunol, Apr. 2006, 7(4): 382-391.
Churchman et al., "Synergism of FAK and tyrosine kinase inhibition in Ph+ B-ALL," JCI Insight, 2016, 1: e86082.
Tanjoni et al., "PND-1186 FAK inhibitor selectively promotes tumor cell apoptosis in three-dimensional environments," Cancer Biol Ther, May 2010, 9: 764-777.
Vitanza et al., "Ikaros Deletions in BCR-ABL-Negative Childhood Acute Lymphoblastic Leukemia Are Associated with a Distinct Gene Expression Signature but Do Not Result in Intrinsic Chemoresistance," Pediatr Blood Cancer, 2014, 61: 1779-1785.
von Palffy et al., "Dominant-negative IKAROS enhances IL-3-stimulated signaling in wild-type but not BCR-ABL1+ mouse BA/F3 cells," Experimental Hematology, 2015, 43: 514-523.

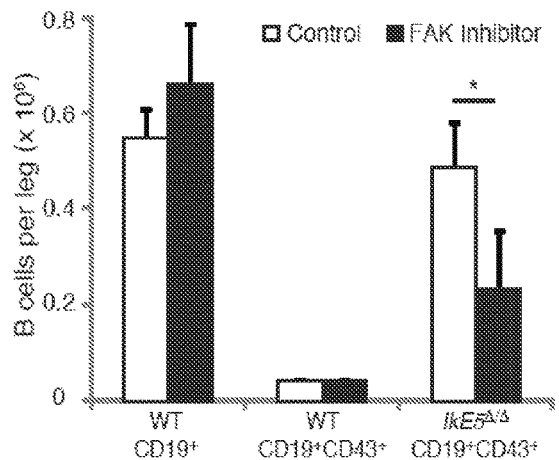
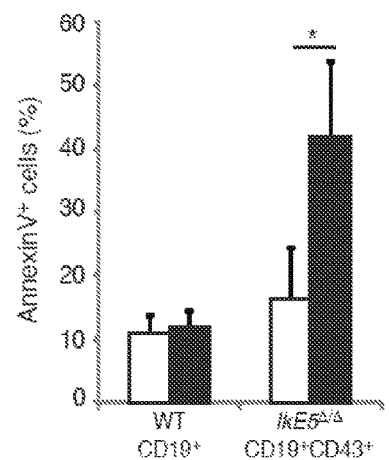
FIG. 6C                FIG. 6D
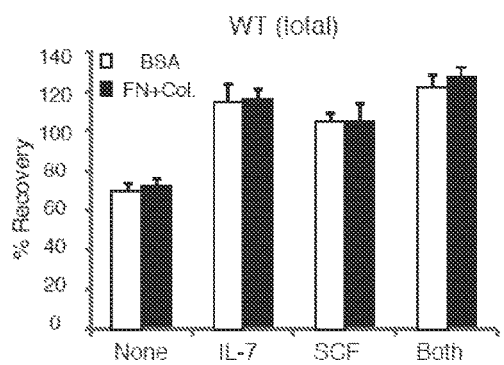
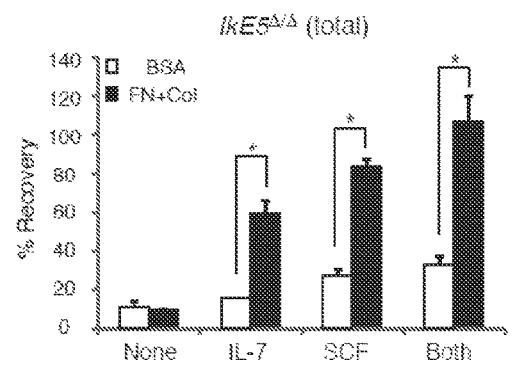
FIG. 7A
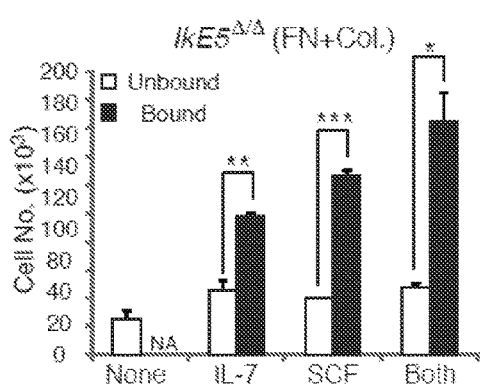
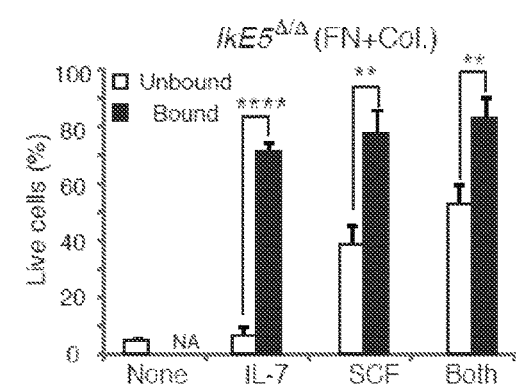
FIG. 7B

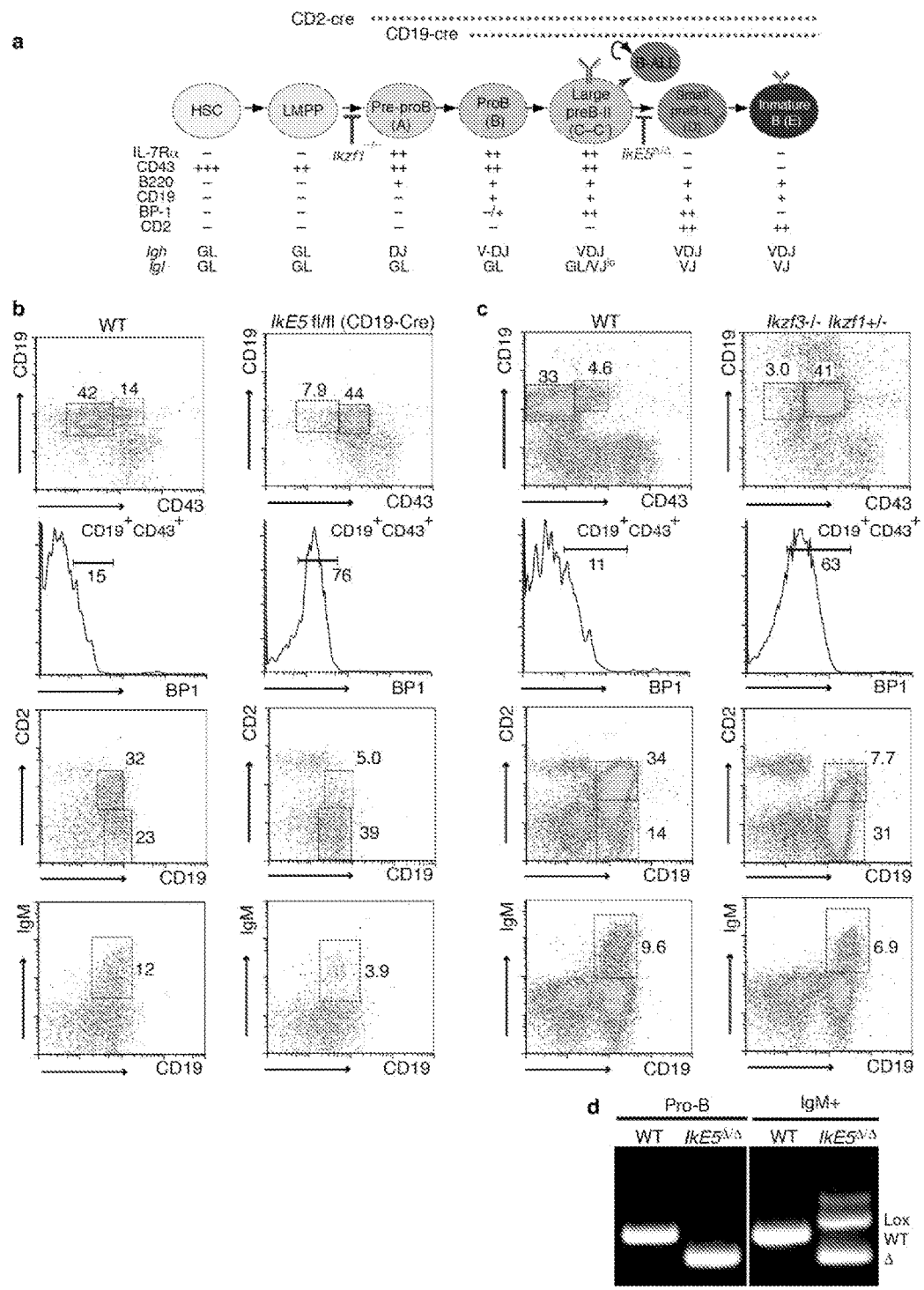
FIGs. 9A-D

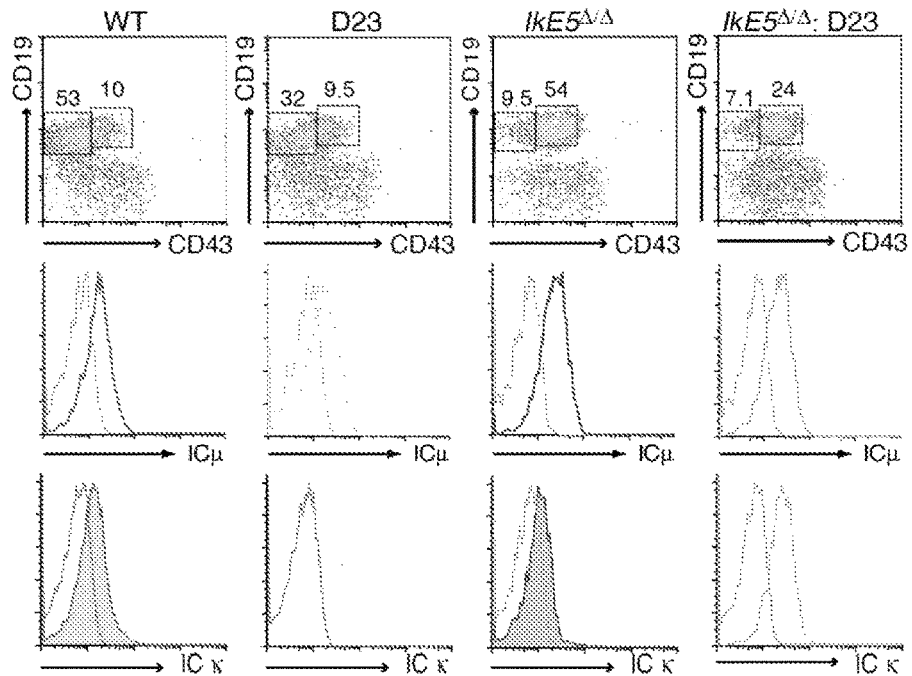
FIG. 10
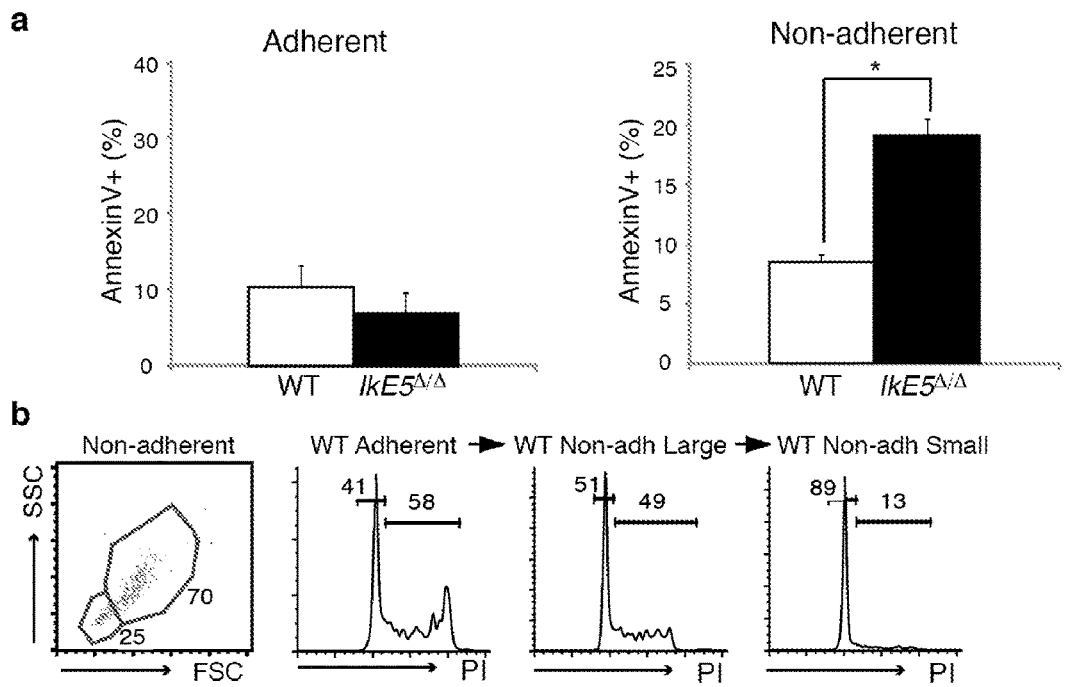
FIGs. 11A-B

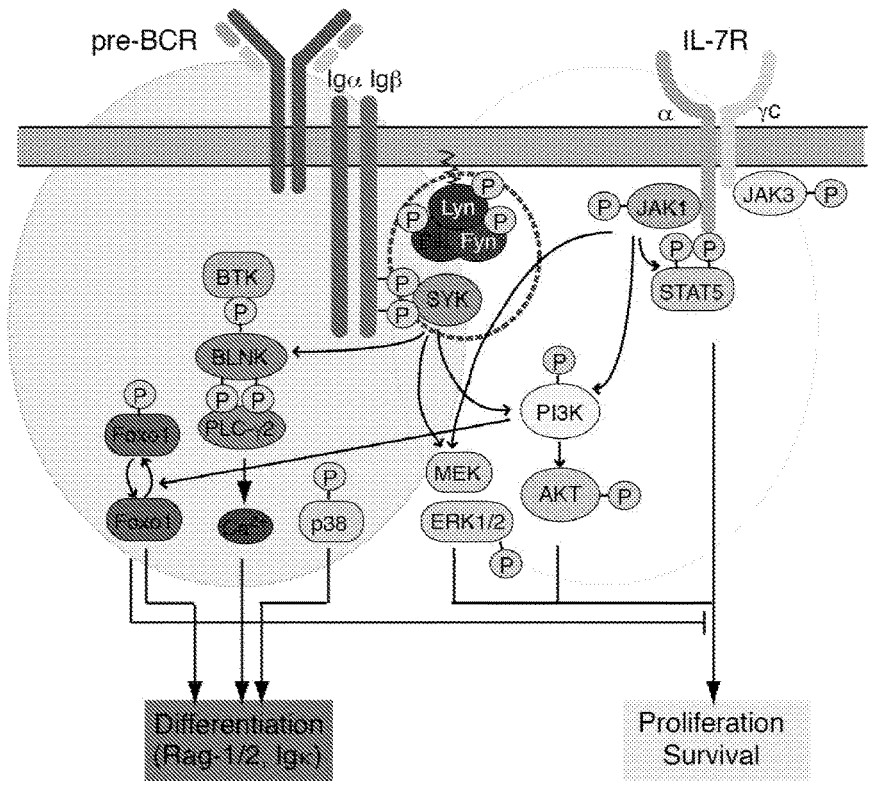
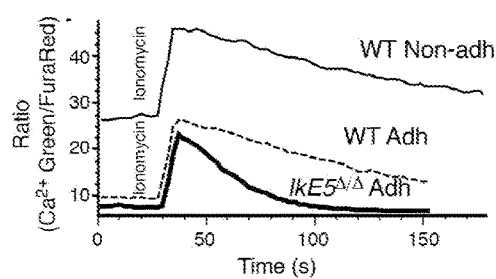
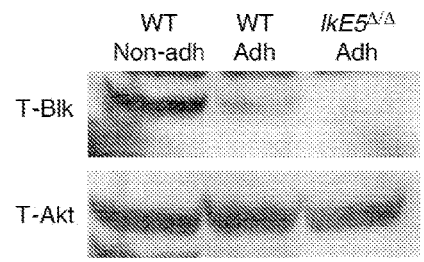
FIGs. 12A-C

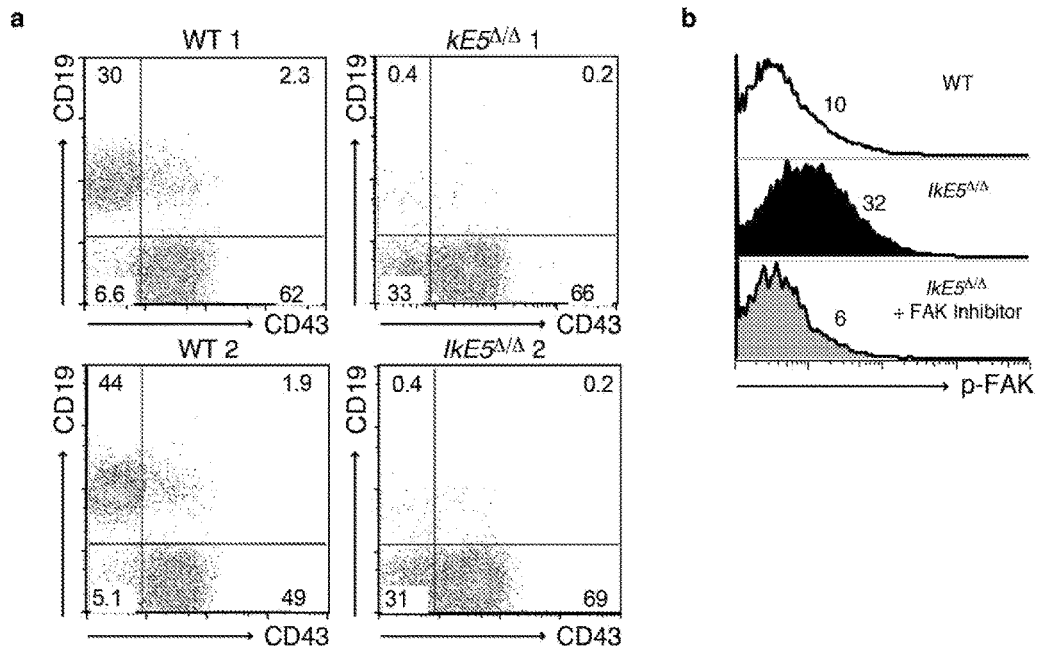
FIGs. 13A-B
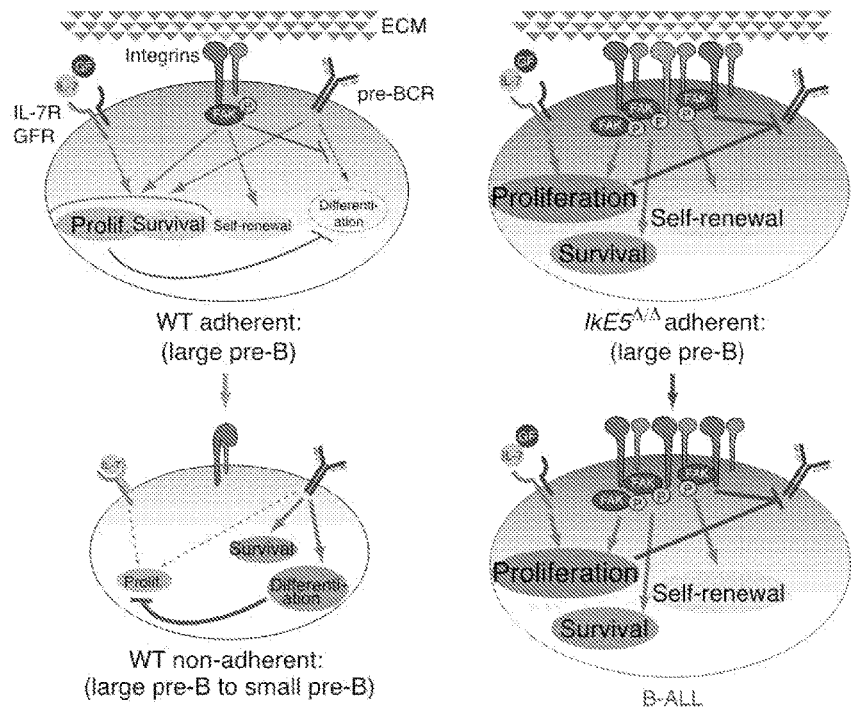
FIG. 14

FIGs. 15A-D

METHODS OF DIAGNOSING AND TREATING B CELL ACUTE LYMPHOBLASTIC LEUKEMIA

CLAIM OF PRIORITY

This application is a U.S. National Phase Application under 35 U.S.C. § 371 of International Patent Application No. PCT/US2014/059870, filed on Oct. 9, 2014, which claims the benefit of U.S. Provisional Patent Application No. 61/888,538, filed on Oct. 9, 2013, and 61/927,397, filed Jan. 14, 2014. The entire contents of the foregoing are incorporated herein by reference.

FEDERALLY SPONSORED RESEARCH OR DEVELOPMENT

This invention was made with Government support under Grant Nos. AI42254, CA162092, and CA090576 awarded by the National Institutes of Health. The Government has certain rights in the invention.

TECHNICAL FIELD

Described herein are methods for the diagnosis and treatment of B cell Acute Lymphoblastic Leukemia (B-ALL), based in part on the detection and/or inhibition of activated Focal Adhesion Kinase (FAK), e.g., phosphorylated FAK (pFAK).

BACKGROUND

Acute lymphoblastic leukemia (ALL) is a neoplasm of immature lymphoid progenitors that is most commonly of B cell lineage. B-precursor acute lymphoblastic leukemia (B-ALL) is the most common childhood malignancy and the number one cause of cancer-related mortality in children and young adults; see Mullighan, J Clin Invest. 122(10):3407-3415 (2012); Hoelzer and Gale, Semin Hematol 24 (1): 27-39 (1987). The vast majority of cases of B-ALL are associated with aneuploidy or gross chromosomal rearrangement.

B cell differentiation is characterized by stage-specific expression of cell surface markers and recombination of the immunoglobulin heavy chain (IgH) and light chain (IgL) genes. These events are responsible for the generation of a large pool of immature B cells from which selection based on antigen receptor specificity takes place[1,2]. Productive rearrangements at the Igh locus allow pairing of the expressed IgM with the surrogate light chains (SLC), VpreB and λ5, and the proximal signaling molecules Igα and Igβ to form a pre-B Cell Receptor (pre-BCR) signaling complex. Subsequent engagement of the protein tyrosine kinases (PTKs) Lyn, Fyn, Blk and Syk activates signaling cascades supporting pre-B cell proliferative expansion and differentiation[3]. Loss-of-function mutations in the pre-BCR signaling complex or in associated PTKs cause arrest at an early B cell precursor stage[4-10]. The pre-BCR, working in concert with the growth-promoting IL-7 cytokine receptor (IL-7R), activates the PI3K-Akt and Mitogen-Activated protein kinases (MAPK) Erk1 and Erk2, thereby providing pre-B cell survival and proliferation[11-14].

Pre-BCR signaling also induces differentiation through a distinct set of signaling effectors such as Btk, Slp65 (Blnk) and PLCγ2 (refs. 15-17). These inhibit the PI3K pathway while activating $Ca^{2+}$ signaling and a network of transcription factors responsible for cell cycle withdrawal and immunoglobulin light chain (IgL) gene rearrangement[18-20]. Although the importance of pre-BCR signaling in proliferation and differentiation is well established, how the transition between these two disparate phases occurs remains unclear. Loss in IL-7R signaling as well as quantitative and qualitative changes in pre-BCR signaling have been proposed as possible mechanisms underlying this pre-B cell switch.

SUMMARY

The present application provides new insight into how pre-B cells switch from proliferation to differentiation, a process that is vulnerable to leukemic transformation. Described herein is a stromal-adherent self-renewing phase in pre-B cell differentiation that expresses the pre-BCR signaling complex and shows strong activation of the Erk1 and Erk2 and PI3K-Akt proliferation and survival pathways, but which has no $Ca^{2+}$ signaling potential, normally required for differentiation. Loss in pre-B cell stromal adhesion correlates with attenuation of proliferation, and an increase in the differentiation-inducing components of the pre-BCR signaling complex and the potential for $Ca^{2+}$ signaling. Importantly, the transition of pre-B cells from a stromal-adherent proliferative to a non-adherent differentiation phase is dependent on Ikaros. Loss of Ikaros augments stromal adhesion in an integrin-dependent manner, locking pre-B cells in a highly proliferative and self-renewing phase from which B-ALL can arise. Importantly, the survival and proliferation of Ikaros-deficient pre-B cells and their malignant counterparts is strictly dependent on the cooperation between integrin and growth factor receptor signaling and is mediated in part by activated FAK, suggesting a new avenue for treatment of IKZF1 mutant, poor-prognosis B-ALL by interfering with these functionally distinct pathways.

Thus, in a first aspect, the invention provides methods for treating a subject who has B cell Acute Lymphoblastic Leukemia (B-ALL); the methods include administering a therapeutically effective amount of an inhibitor of Focal Adhesion Kinase (FAK). Also provided herein is an inhibitor of Focal Adhesion Kinase (FAK) for treating B cell Acute Lymphoblastic Leukemia (B-ALL), and for use in the manufacture of a medicament for treating B-ALL.

In some embodiments, the leukemic cells in the subject have a mutation in IKZF1 that results in haploinsufficiency or expression of a dominant negative form of IKAROS and/or in hyperactivation of FAK activity.

In another aspect, the invention provides methods for selecting a subject for treatment with an inhibitor of FAK. The methods include obtaining a sample from the subject comprising B cells, e.g., TdT+ve CD10+ve CD19+ve B cells, that are known or suspected to be leukemic; performing an assay to determine a level of FAK activity in the sample; comparing the level of FAK activity in the sample to a reference level of FAK activity; identifying a subject as having cells with a level of FAK activity that is above the reference level; and selecting the identified subject for treatment with an inhibitor of FAK. The abbreviation "+ve" means positive and has its customary meaning in the art, i.e., the cells express that protein marker, e.g., on the cell surface.

In some embodiments, performing an assay to determine a level of FAK activity in the sample comprises determining a level of phosphorylated FAK p-Y397 in the subject.

In another aspect, the invention provides methods for selecting a subject for treatment with an inhibitor of FAK. The methods include obtaining a sample from the subject comprising B cells, e.g., TdT+ve CD10+ve CD19+ve B cells, that are known or suspected to be leukemic; performing an assay to detect the presence or absence of a mutation in IKZF1 in the cells; identifying a subject as having cells with a mutation in IKZF1; and selecting the identified subject for treatment with an inhibitor of FAK.

In some embodiments, the mutation in IKZF1 results in haploinsufficiency or expression of a dominant-negative isoform of Ikaros, and/or in hyperactivation of FAK activity.

In some embodiments, the methods include administering a therapeutically effective amount of an inhibitor of FAK.

In some embodiments, the subject has been diagnosed with B-ALL.

In some embodiments, the subject has not been diagnosed with B-ALL.

In another aspect, the invention provides methods for monitoring response to a treatment for B-ALL. The methods include obtaining a sample from a subject comprising B cells, e.g., TdT+ve CD10+ve CD19+ve B cells, that are known or suspected to be leukemic; performing an assay to determine a level of FAK activity in the sample, to provide a baseline level of FAK activity; administering a treatment for B-ALL to the subject; obtaining a subsequent sample from the subject comprising B cells, e.g., TdT+ve CD10+ve CD19+ve B cells, that are known or suspected to be leukemic; performing an assay to determine a level of FAK activity in the sample to provide a treatment level of FAK activity; and comparing the baseline level to the treatment level of FAK activity. A decrease in the level of FAK activity from the baseline to the treatment level indicates that the treatment has been effective; and no change or an increase in the level of FAK activity indicates that the treatment has not been effective.

In another aspect, the invention provides methods for determining risk of relapse in a subject with B-ALL, e.g., B-ALL associated with a mutation in IZKF1. The methods include obtaining a sample from the subject comprising of B cells, e.g., TdT+ve CD10+ve CD19+ve B cells, that are known or suspected to be leukemic; performing an assay to determine a level of FAK activity in the sample; comparing the level of FAK activity in the sample to a reference level of FAK activity; identifying a subject as having cells with a level of FAK activity that is above the reference level as being at increased risk of a relapse; or identifying a subject as having cells with a level of FAK activity that is below the reference level as being at decreased risk of a relapse.

In some embodiments, the risk of relapse is risk of relapse within two weeks, one month, two months, three months, six months, or a year.

In some embodiments, the sample comprises peripheral blood B cells or bone marrow B cells.

A number of FAK inhibitors are known in the art and are suitable for use in the methods described herein, including small molecules, inhibitory nucleic acids, and dominant negative proteins. In some embodiments, the inhibitor of FAK is Compound C4 (chloropyramine hydrochloride); FAK Inhibitor 14; Masitinib; PF 562271 (N-methyl-N-(3-(((2-((2-oxoindolin-5-yl)amino)-5-(trifluoromethyl)pyrimidin-4-yl)amino)methyl)pyridin-2-yl)methanesulfonamide); PF 431396 (N-Methyl-N-[2-[[[2-[(2,3-dihydro-2-oxo-1H-indol-5-yl)amino]-5-(trifluoromethyl)-4-pyrimidinyl]amino]methyl]phenyl]methanesulfonamide); PF 573228 (3,4-Dihydro-6-[[4-[[[3-(methylsulfonyl)phenyl]methyl]amino]-5-(trifluoromethyl)-2-pyrimidinyl]amino]-2(1H)-quinolinone); PF-00562271, the benzenesulfonate salt of PF-562271; VS-4718; VS-6063 (PF-04554878, defactinib); 0ME-TAE-226; NVP-TAE-226; FRNK; PND-1186; TAC-544; 1,2,4,5-Benzenetetraamine terrahydrochloride; or 2-[(5-chloro-2-[[3-methyl-1-(1-methylethyl)-1H-pyrazol-5-yl]amino]-4-pyridinyl)amino]-N-methoxybenzamide, or a pharmaceutically acceptable salt thereof. In some embodiments, the inhibitor of FAK is an inhibitory nucleic acid selected from the group consisting of siRNA, shRNA, and antisense oligonucleotides. In some embodiments, the inhibitor of FAK is a dominant negative FAK protein.

In some embodiments, in the methods described herein the inhibitor of FAK is administered in combination with a kinase inhibitor, e.g., a BCR-ABL tyrosine kinase inhibitor or a JAK/STAT pathway inhibitor. In some embodiments, the tyrosine kinase inhibitor is an ABL1 inhibitor selected from the group consisting of dasatinib, imatinib, nilotinib, bosutinib, ponatinib, bafetinib, and 1,3,4 thiadiazole derivatives, or a JAK/STAT pathway inhibitor selected from the group consisting of INCB018424 (Ruxolitinib); SAR302503 (TG101348); CEP-701 (Lestaurtinib); CYT387; SB1518 (pacritinib); LY2784544; XL019; AZD1480; BMS-911543; and NS-018.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 1A:
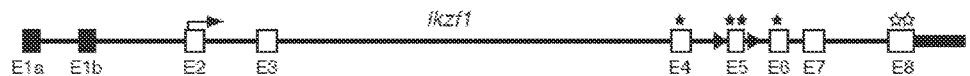
FIG. 1. Pre-B cell differentiation is dependent on the Ikaros gene family.

a, Strategy to generate a conditional Ikzf1 dominant-negative allele. Non-coding (black) and coding (white) exons, with exon 5 flanked by loxP sites (black arrowheads) for deletion are shown at the Ikzf1 locus. Stars mark zinc fingers involved in DNA binding (E4-E6) or protein dimerization (E8). b, Immunoblot analysis of Ikaros isoforms (Ik-1 and Ik-2) in WT and IkE5$^{\Delta/\Delta}$ pre-B cells. Shift in size indicates exon 5 deletion. c, Flow cytometric analysis of wild-type (WT) and IkE5$^{fl/fl}$ CD2-Cre bone marrow (BM) cells. Expression of stage-specific markers (as in FIG. 9a) identify large pre-B cells (CD19$^+$CD43$^+$BP1$^+$), small pre-B cells (CD19$^+$CD2$^+$IgM$^-$), and immature B cells (CD19$^+$IgM$^+$) in the BM. d, Absolute number of cells/(femur+tibia)×2 in various B cell subsets in WT and IkE5$^{\Delta/\Delta}$ BM are shown as a graph of means±standard deviation (s.d.). Asterisks indicate a statistically significant change between WT and mutant B cell subsets (n=10 for WT and mutant; *P<0.01, **P<0.0001, two-tailed Student's t-test). e, Representative cell cycle analysis of ex-vivo isolated large pre-B cells from WT and IkE5$^{fl/fl}$ CD2-Cre mice. Gates show relative number of cells in G0/G1 and S/G2/M phase. f, Igh and Igk rearrangements in Ikaros-deficient pre-B cells. Diagram of Igh and Igk loci depicting proximal and distal V, D and J clusters tested for recombination with primers and probes used for detection. Recombination products were amplified by PCR with decreasing amounts of pre-B cell DNA (depicted as black triangles) and with amplification of Ikzf1 non-deleted genomic fragment as loading control. g, Igk recombination fails to rescue the IkE5$^{\Delta/\Delta}$ large pre-B cell block. Analysis as described in FIG. 1c with intracellular staining for Igκ chain performed on IkE5$^{\Delta/\Delta}$ and IkE5$^{\Delta/\Delta}$: D23 large pre-B cells (CD19$^+$CD43$^+$BP1$^+$).

FIG. 2. Ikaros-deficient pre-B cells grow only on stroma.

a, Flow cytometric analysis of sorted large pre-B cells (CD19$^+$CD43$^+$BP1$^+$) cultured for 7 days stromal-free with limiting serum and IL-7. Differentiation of WT and IkE5$^{\Delta/\Delta}$ large pre-B cells is monitored by stage-specific markers. Arrows indicate the direction of pre-B cell differentiation as depicted in FIG. 9a. b, Growth of WT and IkE5$^{\Delta/\Delta}$ large pre-B cells in high, low, and no (5, 0.05, and 0 ng/ml, respectively) IL-7 concentrations under stromal-free conditions (left) or with OP9 BM stroma (right). The mean absolute number of cells obtained in stromal-free (n=5) and stromal-containing (n=4) cultures with replicates for each experiment is shown in a line graph±s.d. Asterisks denote significant differences between WT and mutant cells (*P<0.05, **P<0.01, two-tailed Student's t-test). c, Mean percentage±s.d. of apoptotic (AnnexinV$^+$) WT and IkE5$^{\Delta/\Delta}$ large pre-B cells in stromal-free cultures as in FIG. 2b, left panel. d, Cell cycle stage distribution (mean percentage±s.d. of cells in S+G2+M) of WT and IkE5$^{\Delta/\Delta}$ large pre-B stromal cultures as in FIG. 2b, right panel. Asterisks in c and d denote significant differences between WT and mutant cells (*P<0.05, **P<0.01, two-tailed Student's t-test). e, Cell cycle kinetics of WT and IkE5$^{\Delta/\Delta}$ large pre-B cells grown on stroma as measured by BrdU pulse-chase. The mean fluorescence intensity (MFI) of BrdU staining is shown at 45 min of pulse and after 48 h of chase.

FIG. 3. A stromal-dependent self-renewing phase in pre-B cell differentiation is greatly augmented by loss of Ikaros.

a, An adherent phase in pre-B cell differentiation as revealed in stromal cultures of WT and IkE5$^{\Delta/\Delta}$ large pre-B cells grown in the presence of IL-7 (5 ng/ml). Areas with adherent cells were marked with rectangles (left) and digitally magnified (right). Dotted circle marks the nucleus of OP9 stromal cells used as a stromal reference (scale bar, 30 μm). b, Ratio of adherent to non-adherent cells in WT and IkE5$^{\Delta/\Delta}$ pre-B cultures at day 2 (D2) and day 3 (D3) with 5 and 0.05 ng/ml of IL-7. The mean ratio is presented±s.d. Asterisks denote significant differences between WT and mutant pre-B cells at each culture time point (*P<0.0001, P<0.01, *P<0.05, two-tailed Student's t-test). c, Comparative expression analysis of pre-B cell differentiation genes in adherent and non-adherent pre-B cells. Hierarchical clustering of normalized gene expression values across different conditions is shown. d, Flow cytometric analysis of adherent and non-adherent cells from WT and IkE5$^{\Delta/\Delta}$ large pre-B cell stromal cultures for CD25 and intracellular Igκ and IgM. The percentages of positive cells relative to isotype control (grey curve) are indicated. e, Rates of propagation of WT adherent and non-adherent pre-B cell fractions grown with 5 ng/ml of IL-7. The mean number of cells generated by 5×10$^4$ adherent or non-adherent WT pre-B cells after replating on OP9 stroma for 3 days of culture is shown in the top panel. The mean number of adherent and non-adherent subsets recovered from plating either WT adherent or non-adherent pre-B cell stromal cultures is shown in the bottom panel. Error bars indicate s.d. Asterisks indicate a statistically significant difference in the growth (top panel) of WT adherent and non-adherent B cells (*P<0.05, **P<0.01, two-tailed Student's t-test). f, Limiting dilution colony forming assay was performed as described previously[29]. The mean frequency of colony forming cells was calculated based on Poisson distribution and is presented in a line graph±s.e. g, Re-association of WT and IkE5$^{\Delta/\Delta}$ adherent pre-B cells after replating on stroma. The mean percentage±s.d. of stromal-adherent cells, measured 3 hrs after replating is shown. Study was performed with two independent WT and mutant pre-B cell cultures (closed and open symbols), each assayed in ten grids/well. Binding to stroma was calculated per twenty grids and averaged for each cell type (*P<0.0001, two-tailed Student's t-test).

FIG. 4. Signaling pathways in WT and Ikaros-deficient pre-B cells a-b, Immunoblot analysis of proliferation and survival (a) and differentiation (b) signaling pathways activated by IL-7R and pre-BCR is shown. Representative expression and activity of pre-BCR-affiliated PTKs and downstream differentiation-inducing signaling effectors, as described in FIG. 12a, are shown from two WT and three IkE5$^{\Delta/\Delta}$ independent stromal cultures of primary cells after limited in vitro propagation. β-tubulin, T-Btk or T-p38 serve as loading controls for WT and IkE5$^{\Delta/\Delta}$ adherent pre-B cells and non-adherent WT pre-B cells. c, Intracellular Ca$^{2+}$ levels (Fura Red, left panel) at steady state and Ca$^{2+}$ flux (Green/Fura Red, right panel) measured after anti-IgM-stimulation of WT and IkE5$^{\Delta/\Delta}$ adherent and non-adherent pre-B cells. Fura Red staining and MFI shown on the left site inversely correlates with Ca$^{2+}$ levels. Data are representative of two independent WT and mutant pre-B cell cultures.

FIG. 5. Increase in integrin signaling mediates adhesion of IkE5$^{\Delta/\Delta}$ pre-B cells to a stromal niche.

a, Pathway analysis of genes upregulated in IkE5$^{\Delta/\Delta}$ relative to WT large pre-B cells. Analysis was performed with a signature of upregulated genes shared by ex vivo mutant pre-B cells prior to and after limited stromal expansion. Pathways enriched for integrins and integrin signaling effectors are highlighted in red. b, Upregulated expression of components of the integrin-actin cytoskeleton pathway in primary and cultured WT and IkE5$^{\Delta/\Delta}$ pre-B cells as defined in FIGS. 1 and 3. Hierarchical clustering of normalized gene expression values across different conditions is shown. c, Cell surface expression of integrins α5, β6, and activated β1 in ex vivo sorted and in vitro cultures of large pre-B cells. MFI for integrin staining is provided. d-f, Increase in FAK activation measured by flow cytometry, immunoblot and confocal microscopy. d, Flow cytometric analysis of p-FAK expression in ex-vivo and in vitro cultured large pre-B cells. MFI for p-FAK is indicated. e, Confocal immunofluorescence microscopy detection of activated p-FAK (red channel in original), GFP-expressing OP9 stroma (green channel in original), and nuclei (DAPI, blue channel in original). Scale bar, 25 μm. f, Immunoblot analysis of total FAK and activated p-FAK, with Btk as a loading control as in FIG. 4a. g, Adhesion of WT and IkE5$^{\Delta/\Delta}$ adherent pre-B cells to fibronectin-coated plates (left panel) in the presence of the fibronectin-derived RGD peptide or the RGE mutant variant (right panel). Asterisks denote significant differences in adhesion between mutant pre-B cells in the presence or absence of RGD or RGE peptides (n=3; *P<0.05, two-tailed Student's t-test). h, Chemotaxis of WT (circle) and IkE5$^{\Delta/\Delta}$ (square) pre-B cells measured in a transwell migration assay in the presence of SDF1. The mean percentage of cells recovered at the bottom of the well in two independent studies is shown.

FIG. 6. FAK inhibition interferes with survival of IkE5$^{\Delta/\Delta}$ pre-B cells.

a-b, In vitro effects of FAK inhibition on pre-B cell stromal adhesion and survival. The mean percentage±s.d. of adherent cells (left) and % inhibition of adhesion±s.d. (right), are shown in (a). The percentage of viable adherent and non-adherent cells recovered in the presence of FAK inhibitor is shown in (b). The data in (a) are from two independent cultures with replicate testing (n=4). For Annexin staining described in (b) replicates were pooled. c-d, In vivo effect of FAK inhibition on IkE5$^{\Delta/\Delta}$ large pre-B cells. c, The mean number±s.d. of pro-B-large pre-B cells (CD19$^+$CD43$^+$) per leg (femur+tibia) of WT (n=2) and IkE5$^{\Delta/\Delta}$ CD19-Cre (n=3) mice is shown after 3-5 doses of FAK inhibitor (WT, n=3; IkE5$^{\Delta/\Delta}$ CD19-Cre, n=6) or vehicle control (WT, n=2; IkE5$^{\Delta/\Delta}$ CD19-Cre, n=3). The effect of FAK inhibitor treatment on total BM B cells (CD19$^+$) in WT mice is also shown. d, Percent of apoptotic cells (mean±s.d.) of BM cells from panel c. Asterisks in a, c, and d denote significant changes in adhesion, cellularity or survival of WT and mutant large pre-B cells in the presence of the FAK inhibitor vs. control (*P<0.05, P<0.01, *P<0.001, two-tailed Student's t-test).

Figure 6A:
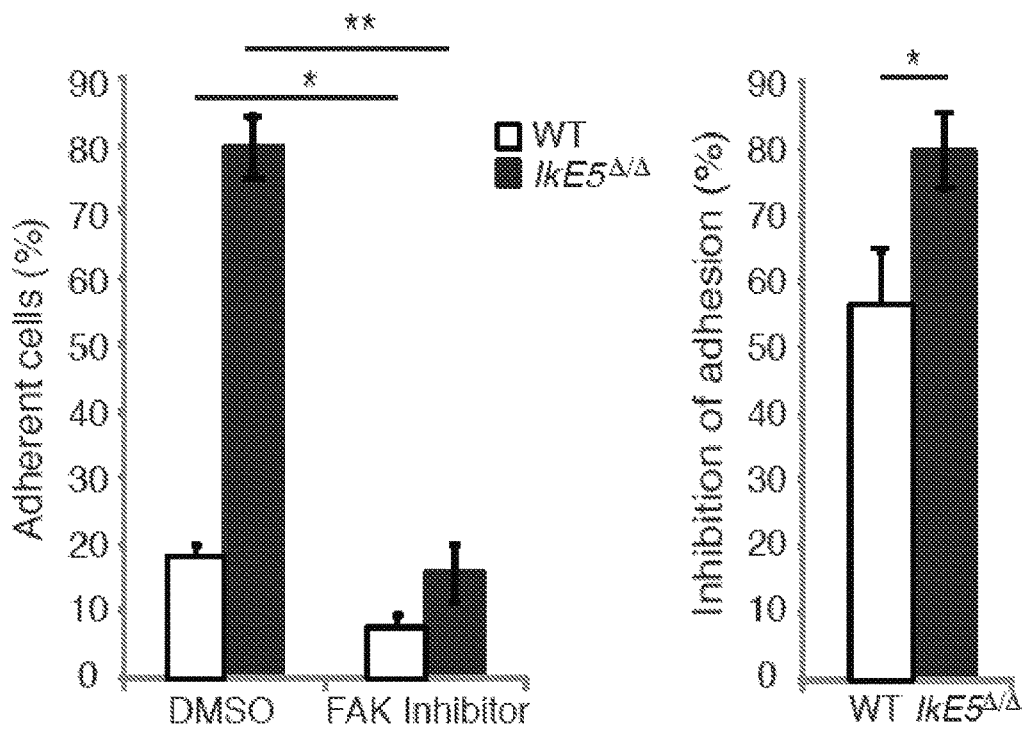
Figure 6B:
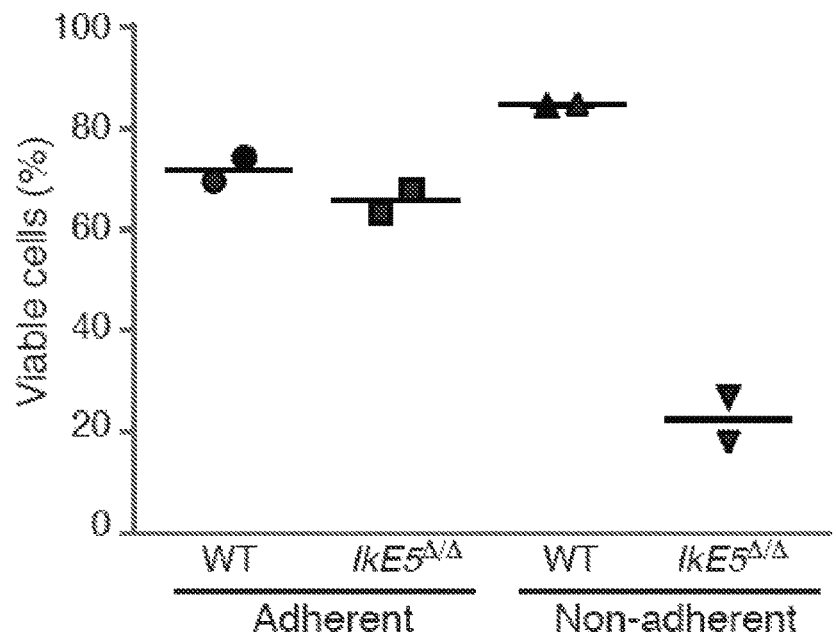

FIG. 7. Cooperation between integrin and growth factor signaling supports survival and proliferation of IkE5$^{\Delta/\Delta}$ pre-B cells.

a, Effect of integrin and cytokine signaling on WT and IkE5$^{\Delta/\Delta}$ pre-B cell survival. Mean percent recovery±s.d. of WT (left) and IkE5$^{\Delta/\Delta}$ (right) adherent pre-B cells after overnight incubation on plates coated with integrin ligands (fibronectin and collagen, FN+Col) or BSA, in the absence (None) or presence of cytokines (IL-7, SCF, or Both). Asterisks denote significant differences in the number of mutant pre-B cells recovered in the presence of cytokines with or without integrin ligand binding. The data shown is from two independent cultures with replicate testing in each (n=4; *P<0.01, two-tailed Student's t-test). b, Effect of integrin and cytokine signaling on survival of IkE5$^{\Delta/\Delta}$ pre-B cells. The mean number±s.d. of plate-bound and -unbound WT and IkE5$^{\Delta/\Delta}$ pre-B cells recovered after overnight incubation in plates coated with integrin ligands (FN+Col) in the presence of cytokines (IL-7, SCF, or Both) or without cytokines (None). The mean percent±s.d. of viable cells in the bound and unbound fractions is shown on the right. Asterisks denote significant changes in number or survival of mutant pre-B cells under the different conditions (n=3; *P<0.05, P<0.01, *P<0.001, ****P<0.0001 two-tailed Student's t-test). c, Effect of integrin and cytokine signaling on proliferation of IkE5$^{\Delta/\Delta}$ pre-B cells. The mean percent±s.d. of cycling cells (S+G2+M) in the bound and unbound fractions of IkE5$^{\Delta/\Delta}$ pre-B cells as described in FIG. 6b is shown. Asterisks denote significant differences in proliferation of mutant pre-B cells measured when bound or not bound to integrin ligands in the presence of different cytokines (n=3; *P<0.05, two-tailed Student's t-test).

FIG. 8. Leukemogenic potential of IkE5$^{\Delta/\Delta}$ pre-B cells.

a, Kaplan-Meier survival curve of NSG mice transplanted with WT or IkE5$^{\Delta/\Delta}$ pre-B cells. The survival of both cohorts of recipients of IkE5$^{\Delta/\Delta}$ pre-B cells was significantly shorter than recipients of WT pre-B cells (P=0.013, Mantel-Cox tests). b, Histopathology of precursor B-cell acute lymphoblastic leukemia/lymphoma derived from IkE5$^{\Delta/\Delta}$ pre-B cells. (i-iii): Hematoxylin & eosin-stained sections of spleen (i), liver (ii), and BM (iii) from a premorbid NSG recipient (sacrificed day 63 post-transplant) of IkE5$^{\Delta/\Delta}$ pre-B cells from a CD19-Cre donor. Note the extensive infiltration of all organs with large cells with moderate cytoplasm and prominent nucleoli, and frequent mitotic figures (arrows). Scale bars, 50 μm. (iv) Wright-Giemsa stain of cytospin of BM from this recipient (scale bar, 20 μm). Note predominant population of large lymphoblasts with immature nuclei and basophilic cytoplasm (arrows). c, Integrin expression is elevated in both IkE5$^{\Delta/\Delta}$ pre-leukemic and leukemic pre-B cells. Percentage of WT, IkE5$^{\Delta/\Delta}$ pre-leukemic and leukemic pre-B cells expressing integrins α5 (CD49e), α6 (CD49f) and β1 (CD29). d, FAK activation (pFAK) measured by flow cytometry in the presence and absence of FAK inhibitor in WT and mutant pre-B cells. e, FAK inhibition interferes with stromal adhesion of IkE5$^{\Delta/\Delta}$ pre-leukemic and leukemic pre-B cells. Inhibitor-treated, closed symbols; vehicle-treated, open symbols. (n=2 each). f, FAK inhibition induces cell death in IkE5$^{\Delta/\Delta}$ pre-leukemic and leukemic pre-B cells (n=4; *P<10$^{-6}$, **P<10$^{-7}$ two-tailed Student's t-test).

FIG. 9. Analysis of B-lymphoid differentiation in Ikaros mutant BM.

a, Schematic representation of B cell differentiation as defined by stage-specific markers. Dotted lines indicate differentiation stages with CD2- or CD19-Cre activity, grey lines the differentiation block associated with germline or conditional Ikaros gene mutations, and grey arrow shows the stage from which B-ALL (shown at the top) is derived. b-c, Representative flow cytometric analyses of wild-type (WT), IkE5$^{fl/fl}$ CD19-Cre (b) and Ikzf3$^{-/-}$ Ikzf1$^{+/-}$ (c) BM cells as described in FIG. 1d, demonstrating a consistent block at the large pre-B cell stage. IkE5$^{fl/fl}$ CD19-Cre, n=9; Ikzf3$^{-/-}$ Ikzf1$^{+/-}$, n=3. d, Deletion analysis of the Ikzf1 locus in pro-B cells (CD19$^+$CD43$^+$c-Kit$^+$BP1$^-$) and immature B cells (CD19$^+$IgM$^+$) sorted from BM of IkE5$^{fl/fl}$ CD2-Cre mice.

FIG. 10. Analysis of B-lymphoid differentiation in Igκ-reconstituted Ikaros mutant pre-B cells.

Flow cytometric analysis of BM B cells from WT, D23, IkE5$^{fl/fl}$ CD2-Cre and IkE5$^{fl/fl}$ CD2-Cre:D23 and intracellular staining for IgM and Igκ in large pre-B cells (CD19$^+$CD43$^+$BP1$^+$).

FIG. 11. Characterization of adherent and non-adherent WT pre-B cells.

a, The mean pro-apoptotic index (percentage of Annexin V$^+$ cells) of WT and IkE5$^{\Delta/\Delta}$ adherent (left panel) and non-adherent (right panel) pre-B cells propagated on OP9 stroma with 5 ng/ml of supplemental IL-7. Asterisk denotes significant changes in apoptosis between WT and mutant pre-B cells (n=2, *P<0.05). b, Representative cell cycle profiles of WT adherent and WT non-adherent pre-B cells grown as in FIG. 2a. WT non-adherent pre-B cells were further subdivided according to FSC. The ratio of small vs. large non-adherent WT pre-B in IL-7 cultures increases over time (data not shown). The progressive loss in proliferation in the WT non-adherent pre-B cell phase seen even in the presence of IL-7, suggests a need for stromal contact for maintenance of pre-B cell proliferation. Withdrawal of IL-7 accelerates this process with the ratio of small-non-cycling/large-cycling non-adherent pre-B cells increasing dramatically within 24 hrs (data not shown).

FIG. 12. Signaling pathways in WT and IKAROS-deficient pre-B cells.

a. Schematic representation of signaling pathways operating downstream of pre-BCR and IL-7R and supporting pre-B cell proliferation, survival and differentiation. Signaling effectors assayed for expression and activity in FIG. 4a, b are shown. b, Ca$^{2+}$ flux (Ca$^{2+}$ Green/Fura Red) after ionomycin treatment of WT and IkE5$^{\Delta/\Delta}$ adherent and WT non-adherent pre-B cells, n=2. c, Total Blk expression is shown for WT and IkE5$^{\Delta/\Delta}$ adherent and non-adherent pre-B cells, with total Akt (T-Akt) as loading control.

FIG. 13. Lack of circulating IkE5$^{\Delta/\Delta}$ pre-B cells and reduction of p-FAK by FAK inhibitor.

a, Flow cytometric analysis of peripheral blood from wild-type (WT) and IkE5$^{fl/fl}$ CD19-Cre mice for large pre-B (CD19$^+$CD43$^+$) and small pre-B cells (CD19$^+$CD43$^-$); n=2 for each genotype. b, FAK inhibitor treatment reduces p-FAK staining in BM IkE5$^{\Delta/\Delta}$ pre-B cells, as described in FIG. 6b.

FIG. 14. Model of pre-BCR, growth factor, and integrin signaling interactions operating during pre-B cell differentiation. Augmentation of integrin signaling by IkE5$^{\Delta/\Delta}$ mutation blocks cells in a stromal-dependent, self-renewing and highly proliferative state where they are unable to differentiate, from which B-ALL arises.

Figure 1B:
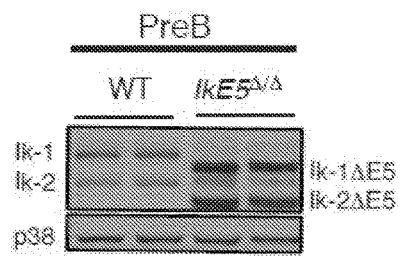
Figure 1C:
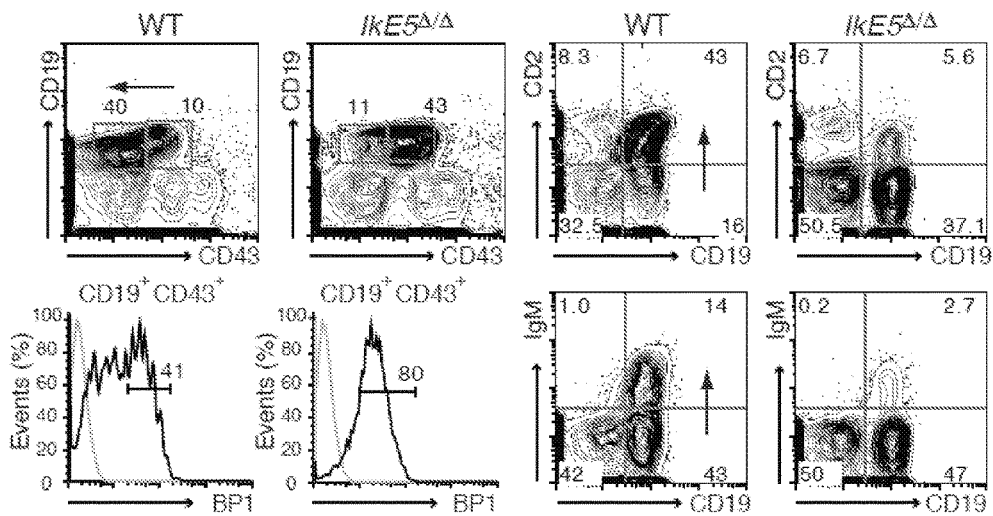
Figure 1D:
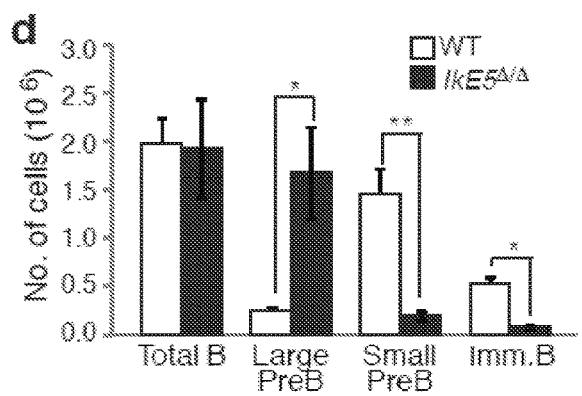
Figure 1E:
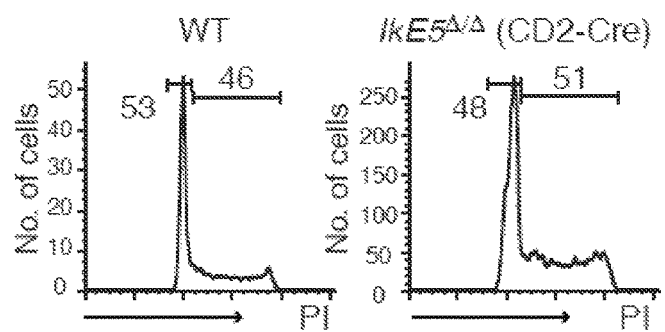
Figure 1F:
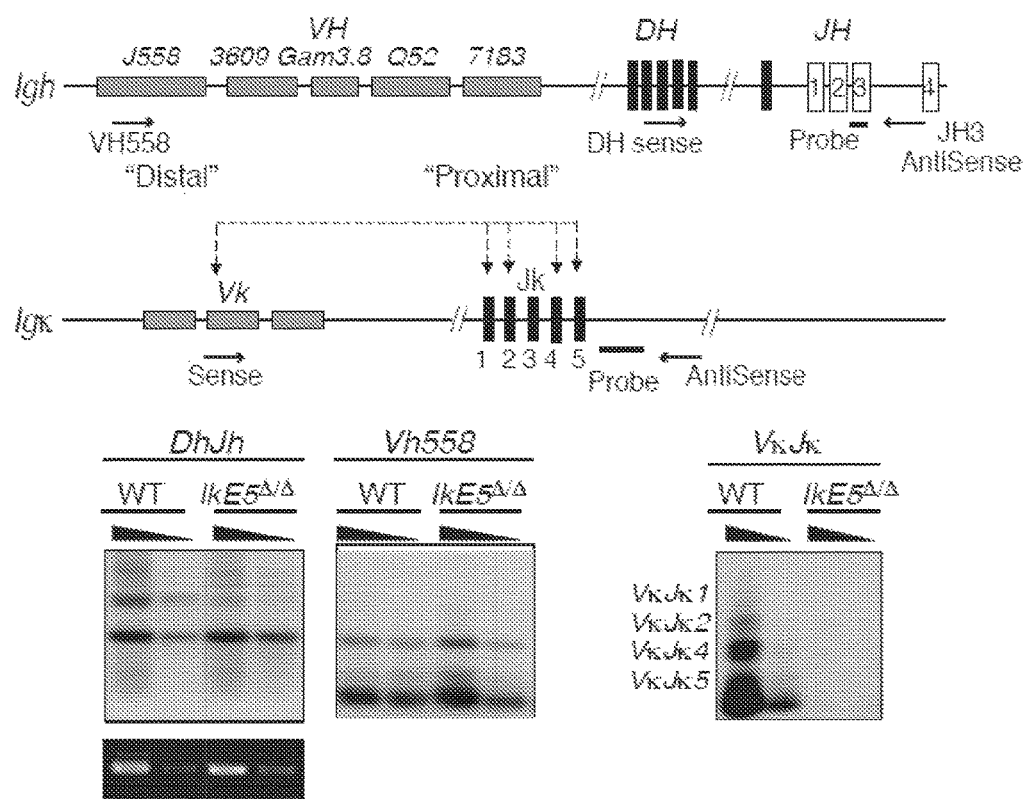
Figure 1G:
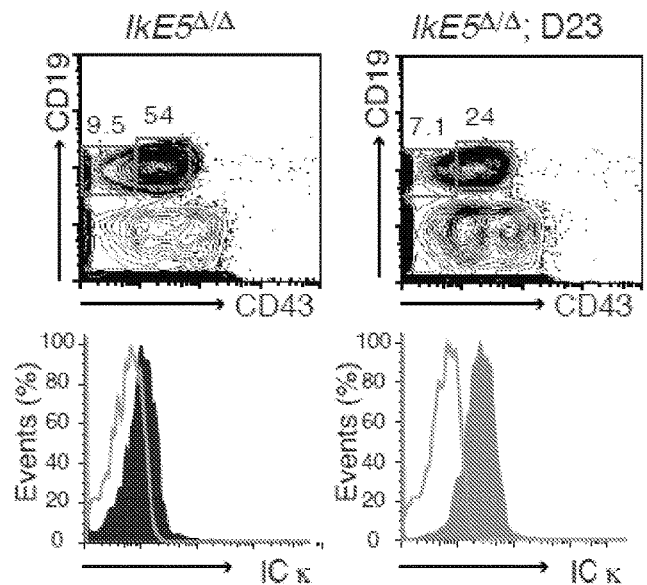
Figure 15:
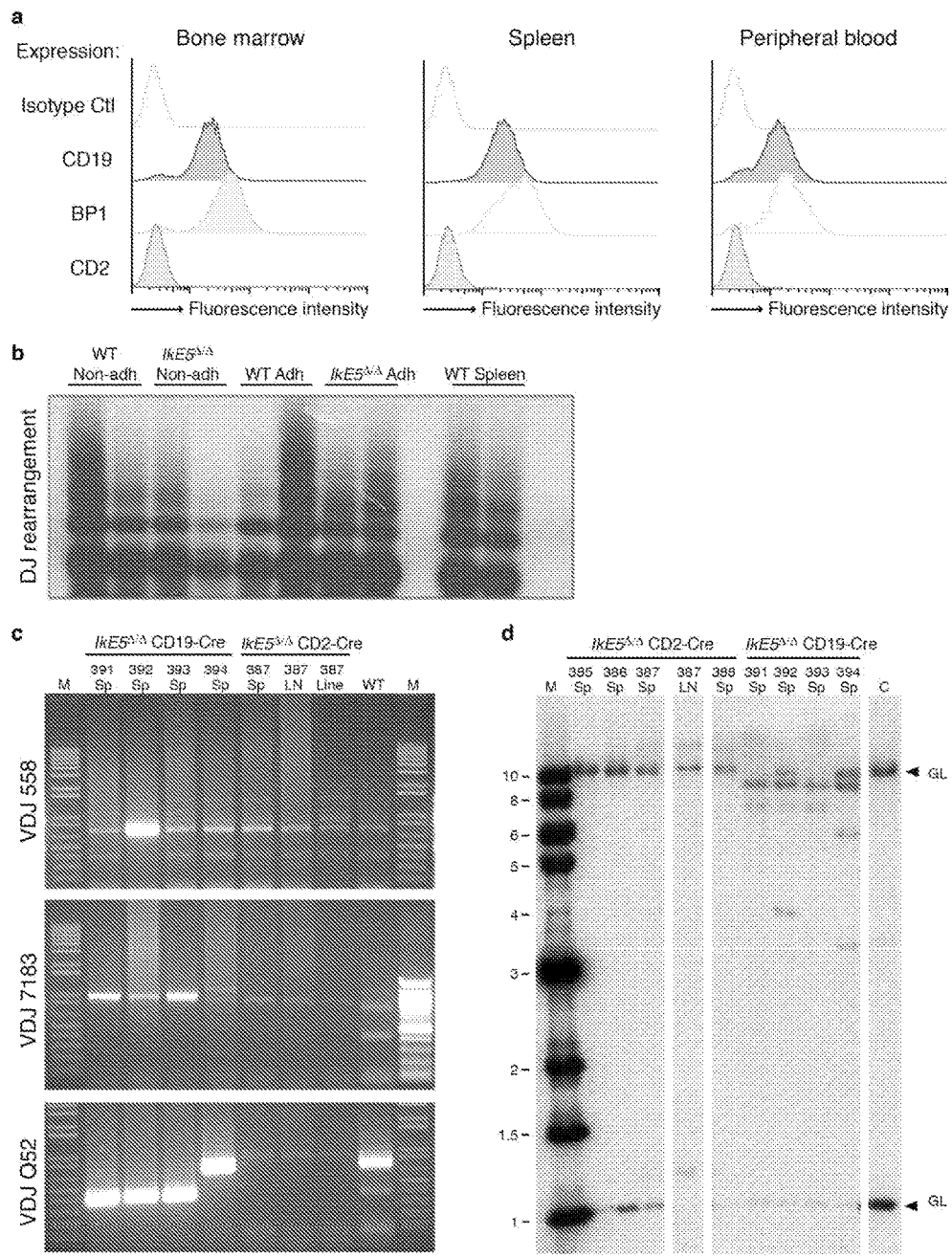

FIG. 15. Clinicopathological characterization of lymphoid tumors from recipients of IkE5$^{\Delta/\Delta}$ pre-B cells. a, Immunophenotypic analysis of precursor B-cell acute lymphoblastic leukemia/lymphoma derived from IkE5$^{\Delta/\Delta}$ pre-B cells demonstrates a similar large pre-B cell surface phenotype (CD19$^+$CD43$^+$BP1$^+$CD2$^-$) to the original transplanted population. b, Analysis of parental WT and IkE5$^{\Delta/\Delta}$ pre-B cell populations (non-adherent and adherent), showing polyclonal Igh rearrangements similar to that observed in WT splenocytes. The PCR-based D-J rearrangement assay described in FIG. 1f was used to determine clonality. PCR products were probed with a JH-specific probe. c, PCR analysis of V-D-J rearrangements in lymphoid tumors from NSG recipients of IkE5$^{\Delta/\Delta}$ pre-B cells, as described in FIG. 1f. Forward primers from specific VH regions (558, Q52, 7183) were used in conjunction with a common reverse primer from JH3 (FIG. 1f). Note that lymphoid tumors from mice #391, 393, and 394 (from IkE5$^{\Delta/\Delta}$ CD19-Cre donor) had monoclonal Igh rearrangement while #392 tumor had clonal rearrangement of both Igh alleles. d, Southern blot analysis of Igh gene rearrangements in tissues of leukemic NSG recipients of IkE5$^{\Delta/\Delta}$ pre-B cells, as in panel c. The position of two germline (GL) Igh bands (present in control BM myeloid cells, "C") is denoted by arrowheads. The tissue origin of the sample is indicated (Sp, spleen; LN, lymph node). Common rearrangements between tumors from IkE5$^{\Delta/\Delta}$ CD19-Cre recipients are indicated by asterisks. Rearrangements in IkE5$^{\Delta/\Delta}$ CD2-Cre recipients #385 and 386 may not be detected by this probe.

Figure 16:
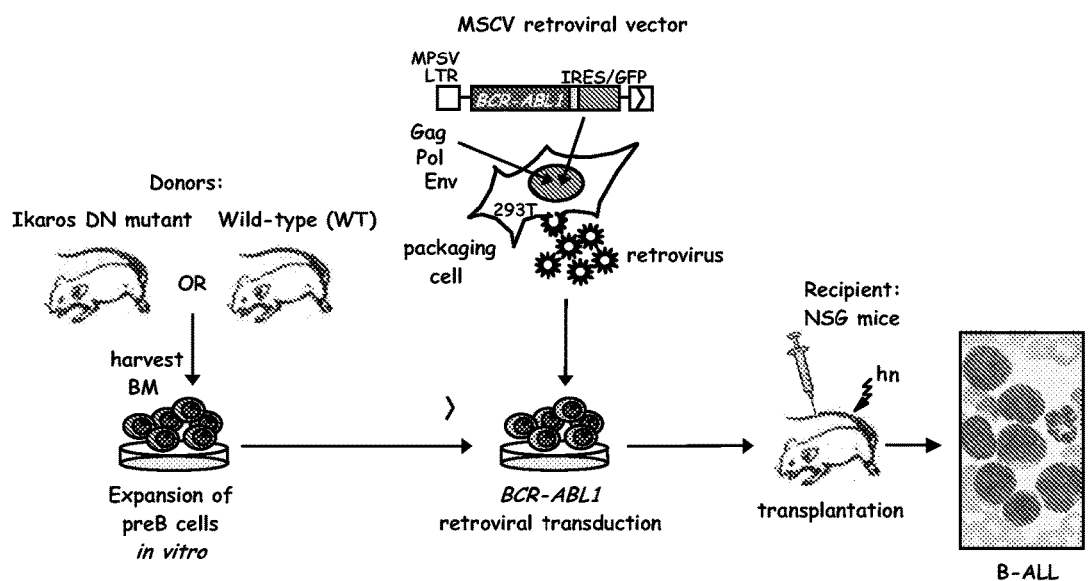
Figure 17A:
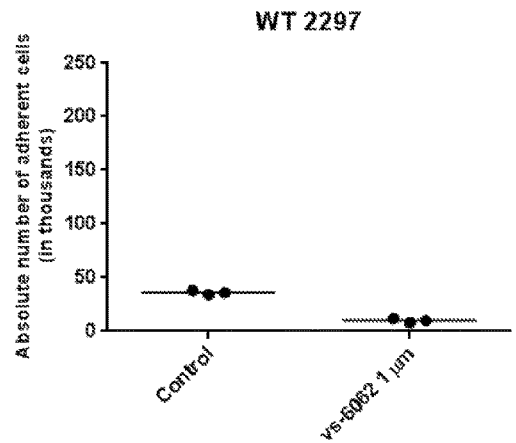
Figure 17B:
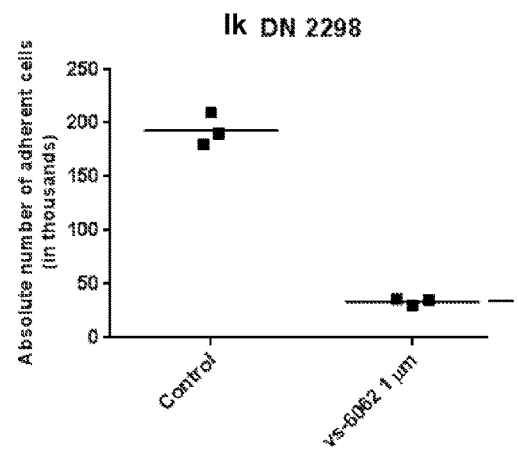
Figure 17C:
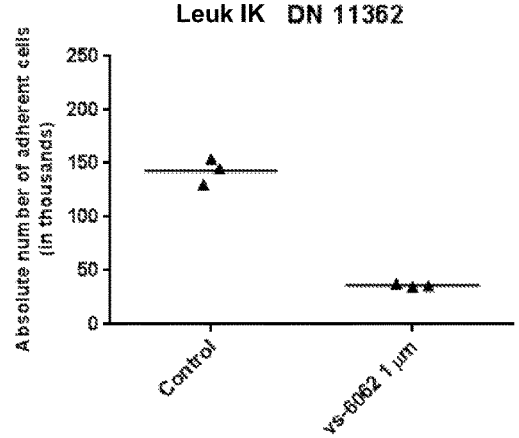
Figure 17D:
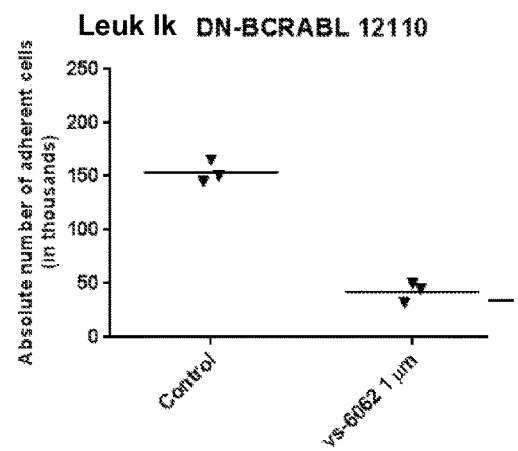
Figure 18A:
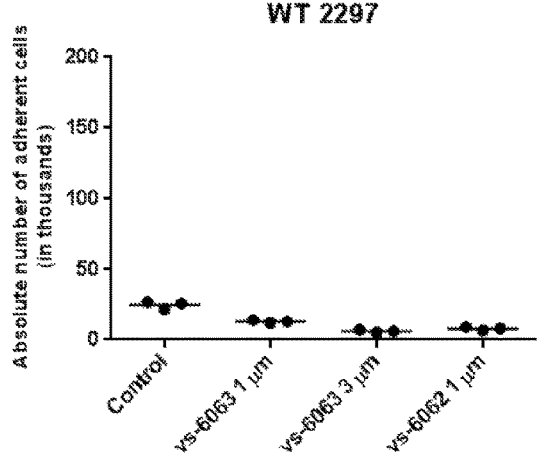
Figure 18B:
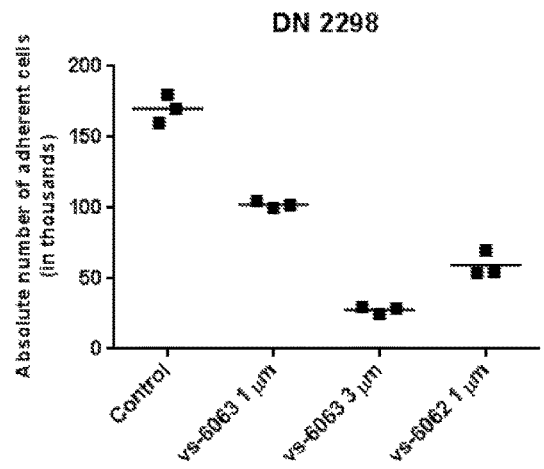
Figure 18C:
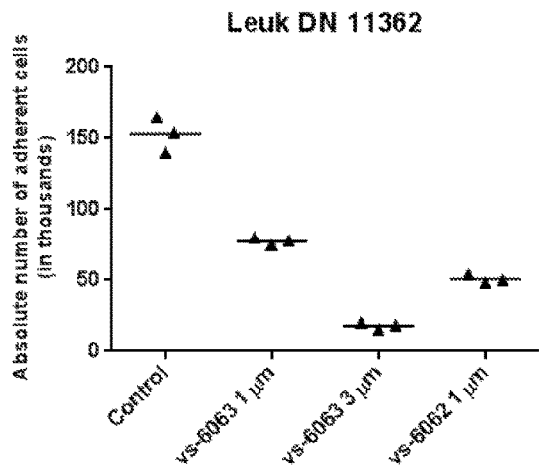
Figure 18D:
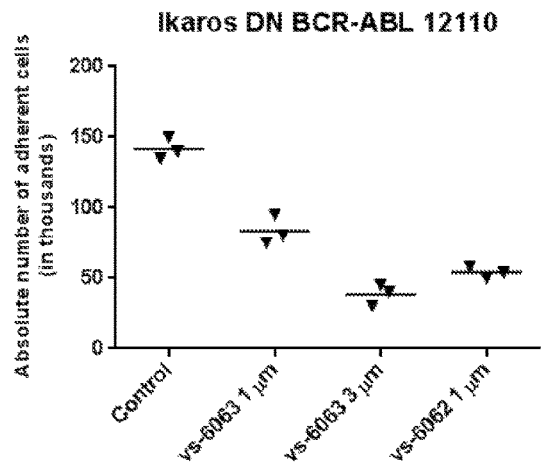
Figure 19A:
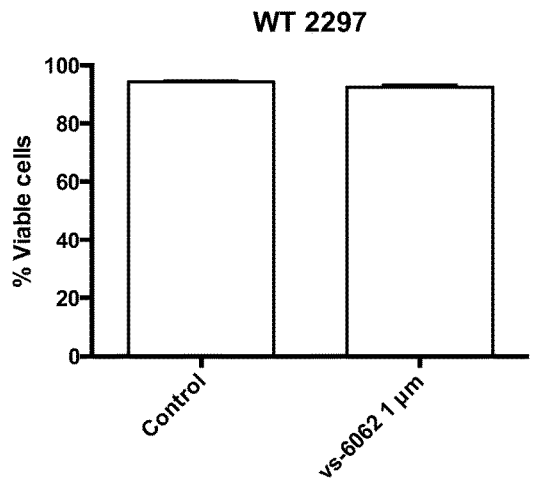
Figure 19B:
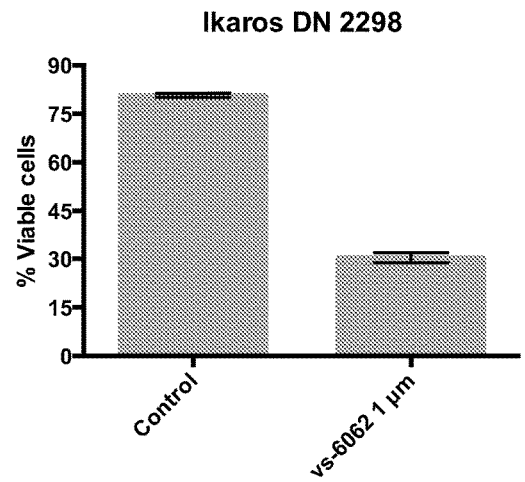
Figure 19C:
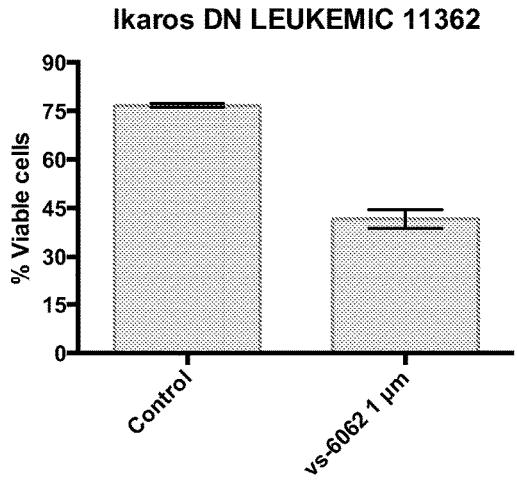
Figure 19D:
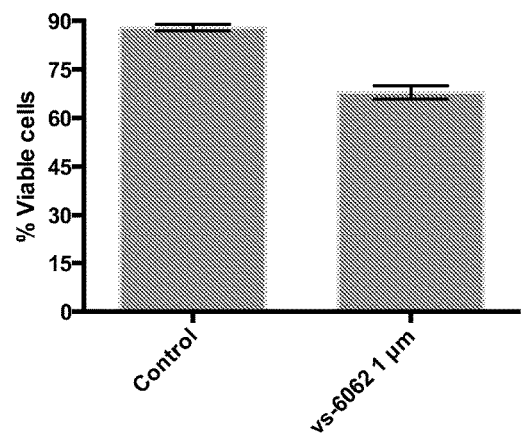
Figure 19E:
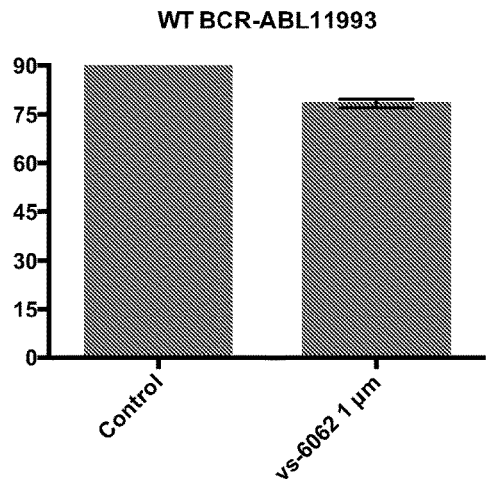
Figure 20A:
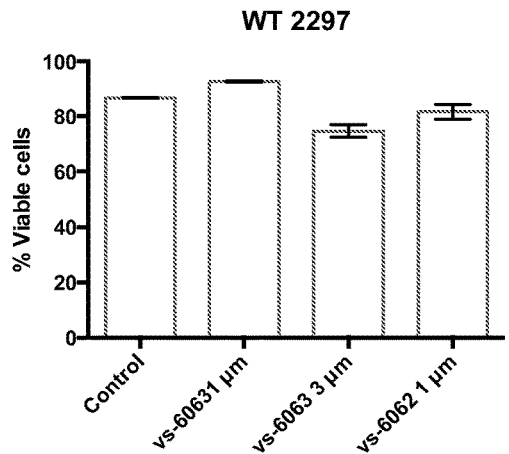
Figure 20B:
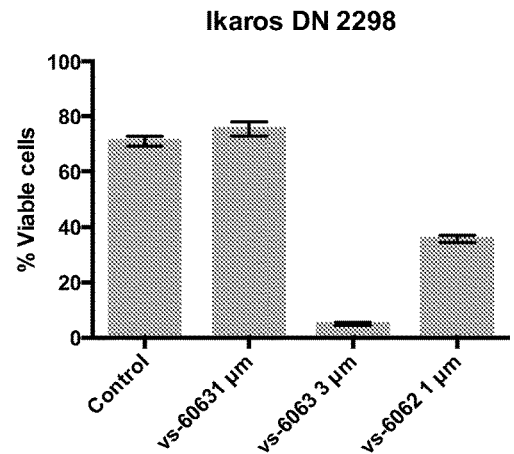
Figure 20C:
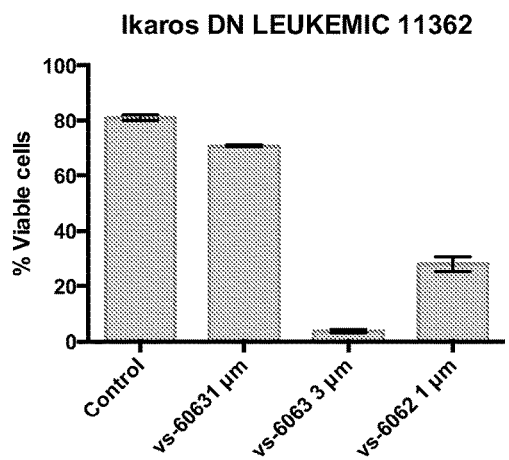
Figure 20D:
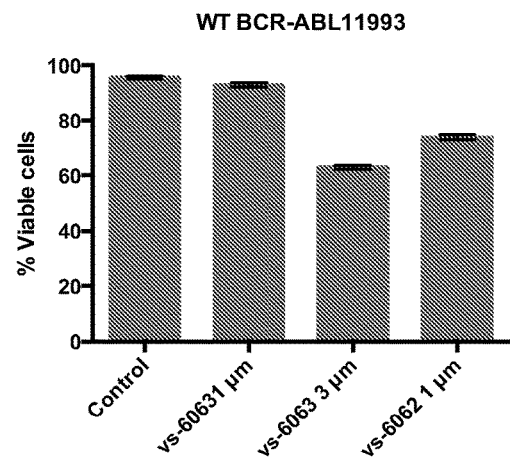
Figure 20E:
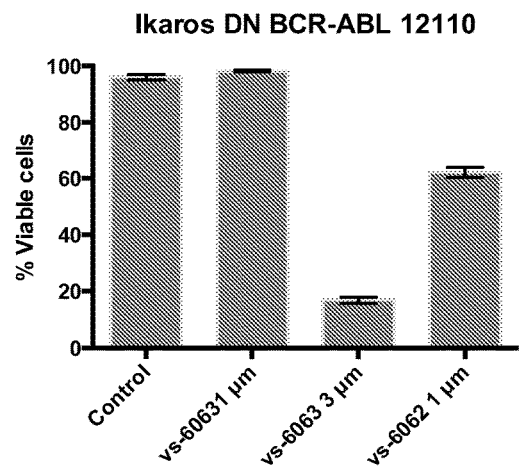

FIG. 16. A schematic illustration of an exemplary experimental approach for generating Ikaros mutant BCR-ABL1 or BCR-ABL1 leukemic preB cells. The BCR-ABL1 oncogene was cloned in the MSCV retroviral vector, which co-expressed green fluorescent protein (GFP) from an internal ribosome entry site (IRES). Bone marrow preB cells were harvested from mice with Ikaros mutation or from normal (Wild-type) mice, expanded briefly in culture, then infected (transduced) with the retrovirus. The donors were not treated with 5-FU and transduction took place without cytokines. Transduced BM cells were plated directly on stroma in vitro or injected into irradiated recipients to induce B-ALL.

FIG. 17. FAK inhibitors reduce adhesion of pre-leukemic and leukemic preB cells. Absolute numbers of adherent wild type (WT, 17A), pre-leukemic IkE5$^{\Delta/\Delta}$ (2298, 17B), Leukemic IkE5$^{\Delta/\Delta}$ (11362, 17C) and BCR-ABL1$^+$ IkE5$^{\Delta/\Delta}$ (12110, 17D) cells untreated (control) and treated with FAK inhibitor vs-6062 (1 µM) for 24 hours.

FIG. 18. FAK inhibitors reduce adhesion of pre-leukemic and leukemic preB cells. Absolute numbers of adherent wild type (WT, 18A), pre-leukemic IkE5$^{\Delta/\Delta}$ (2298, 18B), Leukemic IkE5$^{\Delta/\Delta}$ (11362, 18C) and BCR-ABL1$^+$ IkE5$^{\Delta/\Delta}$ (12110, 18D) cells untreated (control) and treated with FAK inhibitors vs-6063 (1 µm, 3 µM) and vs-6062 (1 µM) for 24 hours.

FIG. 19. FAK inhibitors reduce viability of pre-leukemic and leukemic preB cells. Percentage of viable non-adherent wild type (WT, 19A), pre-leukemic IkE5$^{\Delta/\Delta}$ (2298, 19B), Leukemic IkE5$^{\Delta/\Delta}$ (11362, 19C), BCR-ABL1$^+$ IkE5$^{\Delta/\Delta}$ (12110, 19D) and WT BCR-ABL1$^+$ cells untreated (control, 19E) and treated with FAK inhibitor vs-6062 (1 µM) for 24 hours.

FIG. 20. FAK inhibitors reduce viability of pre-leukemic and leukemic preB cells. Percentage of viable non-adherent wild type (WT, 20A), pre-leukemic IkE5$^{\Delta/\Delta}$ (2298, 20B), Leukemic IkE5$^{\Delta/\Delta}$ (11362, 20C), BCR-ABL1$^+$ IkE5$^{\Delta/\Delta}$ (12110, 20D) and WT BCR-ABL1$^+$ cells untreated (control, 20E) and treated with FAK inhibitors vs-6063 (1 µM, 3 µM) and vs-6062 (1 µM) for 24 hours.

Figure 21:
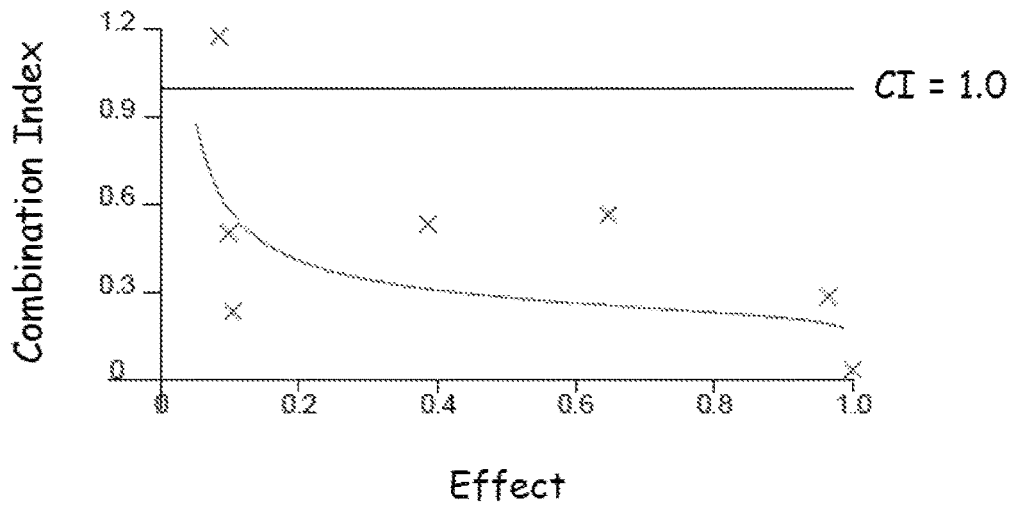

FIG. 21. FAK inhibitor and the ABL1 kinase inhibitor dasatinib synergize against Ikaros-mutant BCR-ABL1+ leukemia. This is a Combination-Index or Chou-Talalay plot of the Fraction Affected (Fa) of various combinations of dasatinib and FAK inhibitor (red x symbols) and their respective CI values. CI values less than 1.0 (below line) are indicative of synergy of the combination.

FIG. 22. Treatment of primary human B-ALL samples with FAK inhibitor. 14171-WT BCR-ABL1 (Ph+); 19309-Ik6 BCR-AB1L (Ph+) Fold change in viability depicted with Annexin V staining of human WT BCR-ABL1$^+$ (14171) and BCR-ABL1$^+$ IkE5$^{\Delta/\Delta}$ (19309) cells treated with FAK inhibitors vs-6062 (1 µM) relative to untreated controls for 24 (22A) and 48 (22B) hours.

FIG. 23. Treatment of human Ph-negative Ik6+ B-ALL sample #128(E.P) with FAK inhibitor for 48 hours (performed in triplicate). Absolute numbers for total cellularities (23A), non-adherent (23B) and adherent (23C) BCR-ABL1$^{neg}$ IkE5$^{\Delta/\Delta}$ (#128) cells treated with FAK inhibitors vs-6062 (1 µM) relative to untreated controls at 48 hours.

Figure 24:
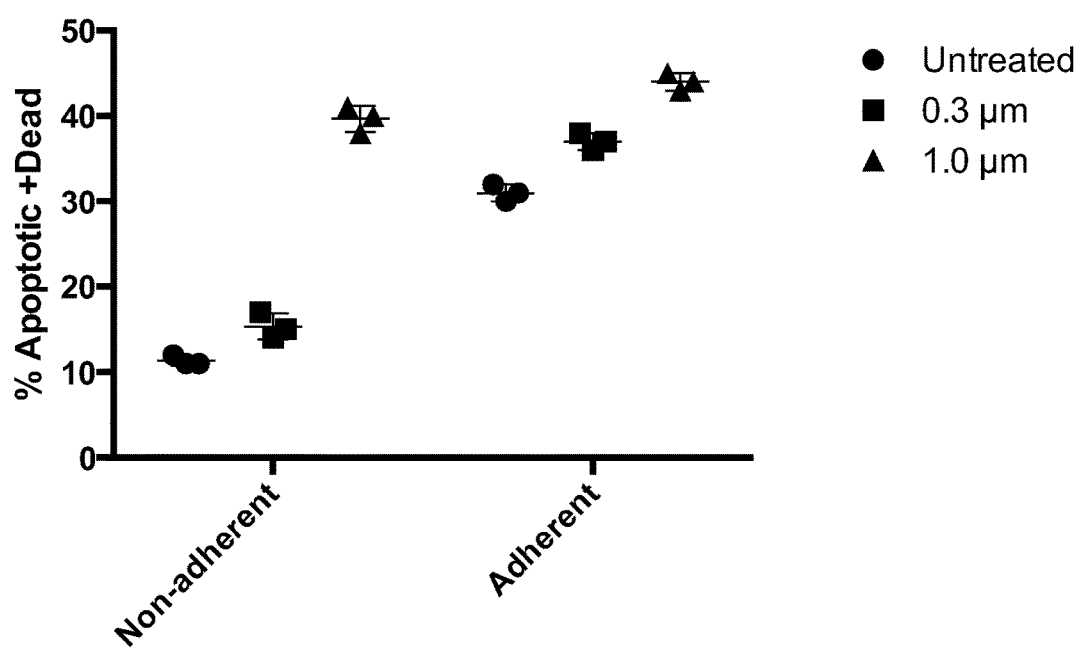

FIG. 24. Treatment of human Ph-negative Ik6+ B-ALL sample #128(E.P) with FAK inhibitor for 48 hours (performed in triplicate). Percentage of Annexin V positive cells are shown in untreated and FAK inhibitor vs-6062 (0.3 µM and 1 µM) treated non-adherent and adherent fraction in the BCR-ABL1$^{neg}$ IkE5$^{\Delta/\Delta}$ (#128) cells.

Figure 25:
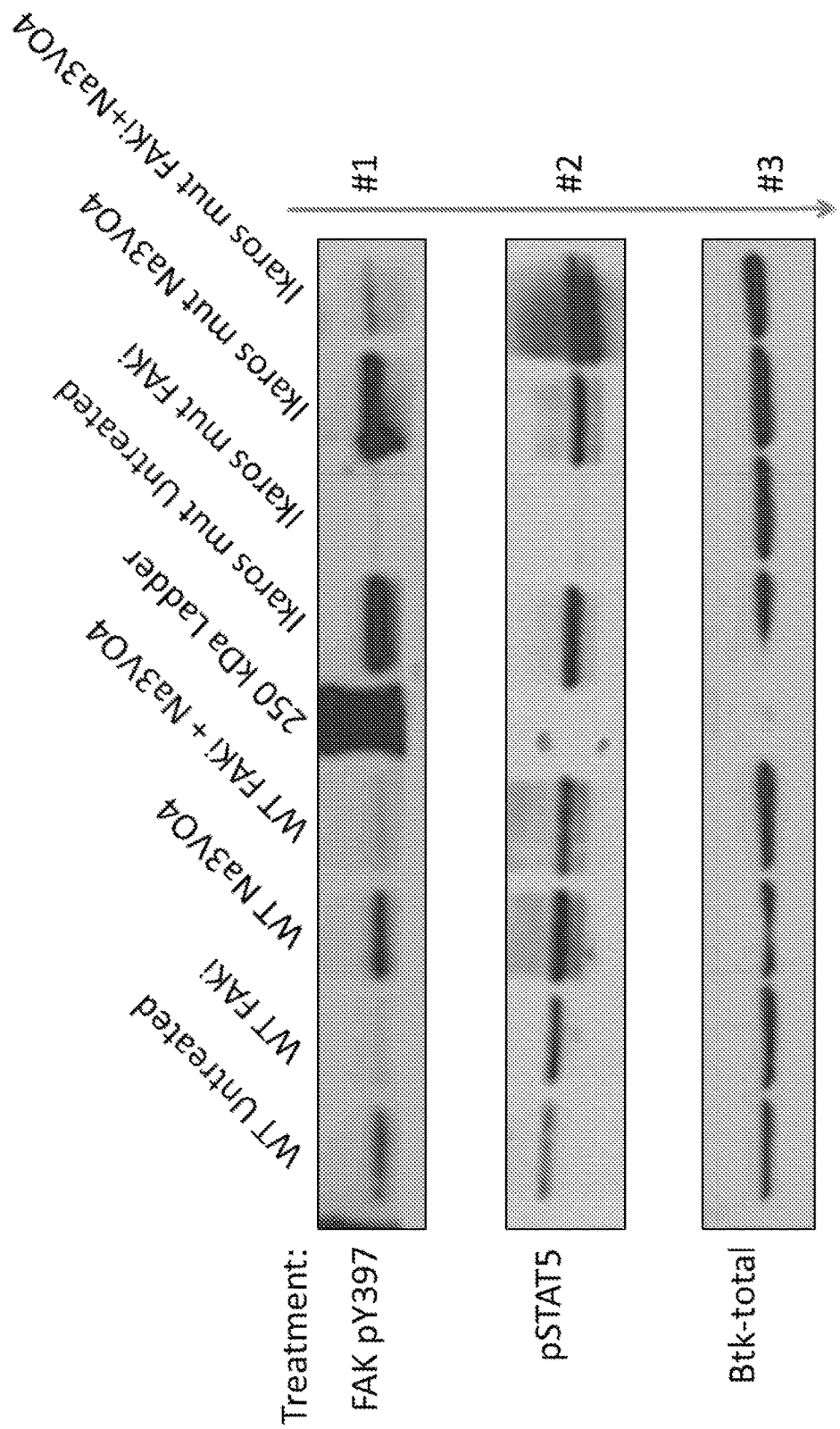

FIG. 25. Effect of FAK inhibitor on WT and Ikaros mutant Pre-leukemic preB cell signaling. Whole cell extracts were prepared using RIPA buffer for western blot analysis of WT and pre-leukemic IkE5$^{\Delta/\Delta}$ (Ikaros mut). Status of FAK activity (FAK pY397) and STAT5 signaling (pSTAT5) was examined in untreated, FAK ihibitor treated (1 µm vs-6062, FAKi), phosphatase inhibitor treated (Na3VO4) and combination of both (Faki+Na3VO4).

Figure 26:
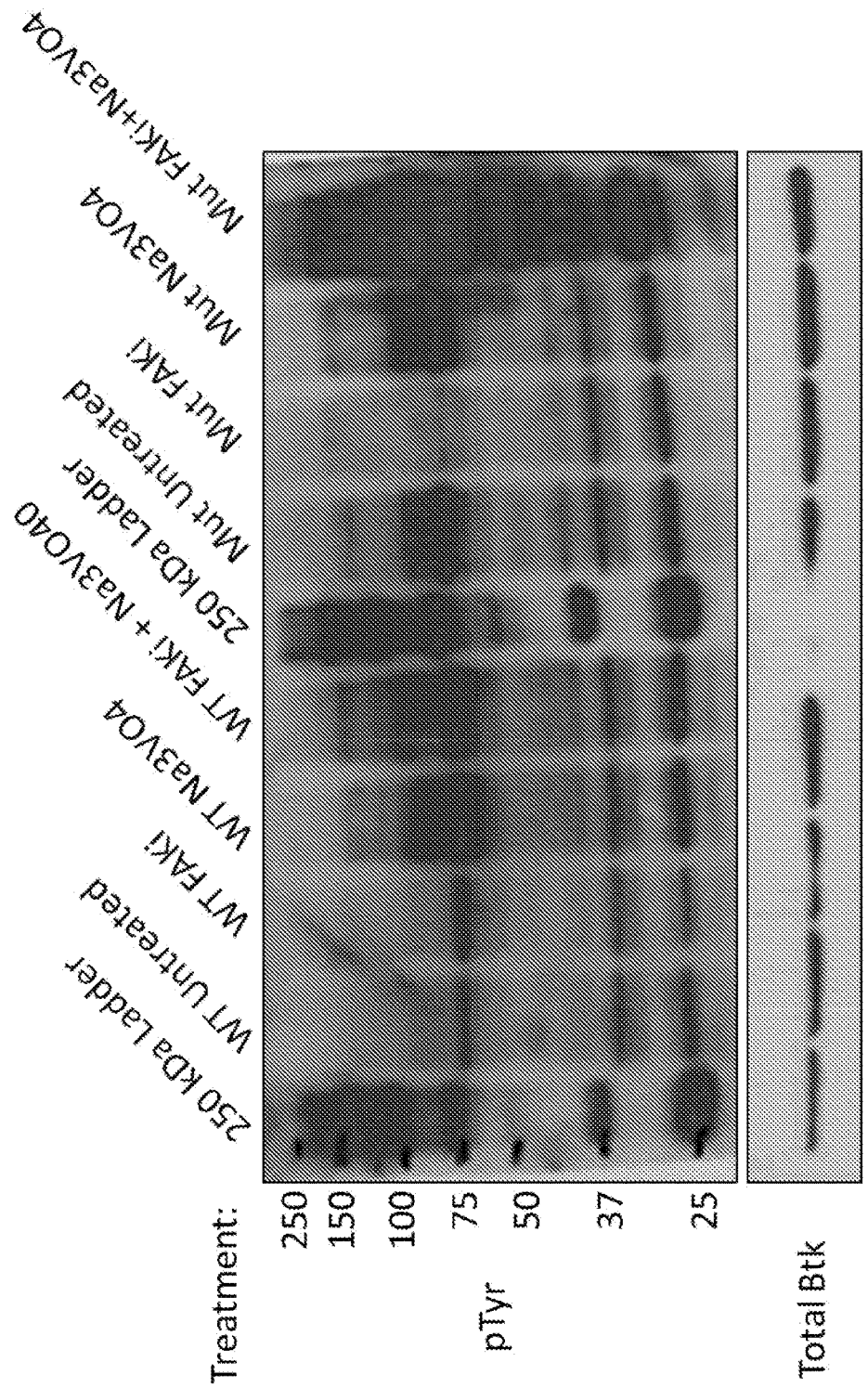

FIG. 26. Effects of FAKi on tyrosine kinome in WT and IKDN preB cells. Whole cell extracts were prepared using RIPA buffer for western blot analysis of WT and pre-leukemic IkE5$^{\Delta/\Delta}$ (Mut) cells. Status of tyrosine kinase activity was examined using p-Tyr antibody in untreated, FAK inhibitor treated (1 µm vs-6062, FAKi), phosphatase inhibitor treated (Na3VO4) and combination of both (Faki+Na3VO4).

Figure 27:
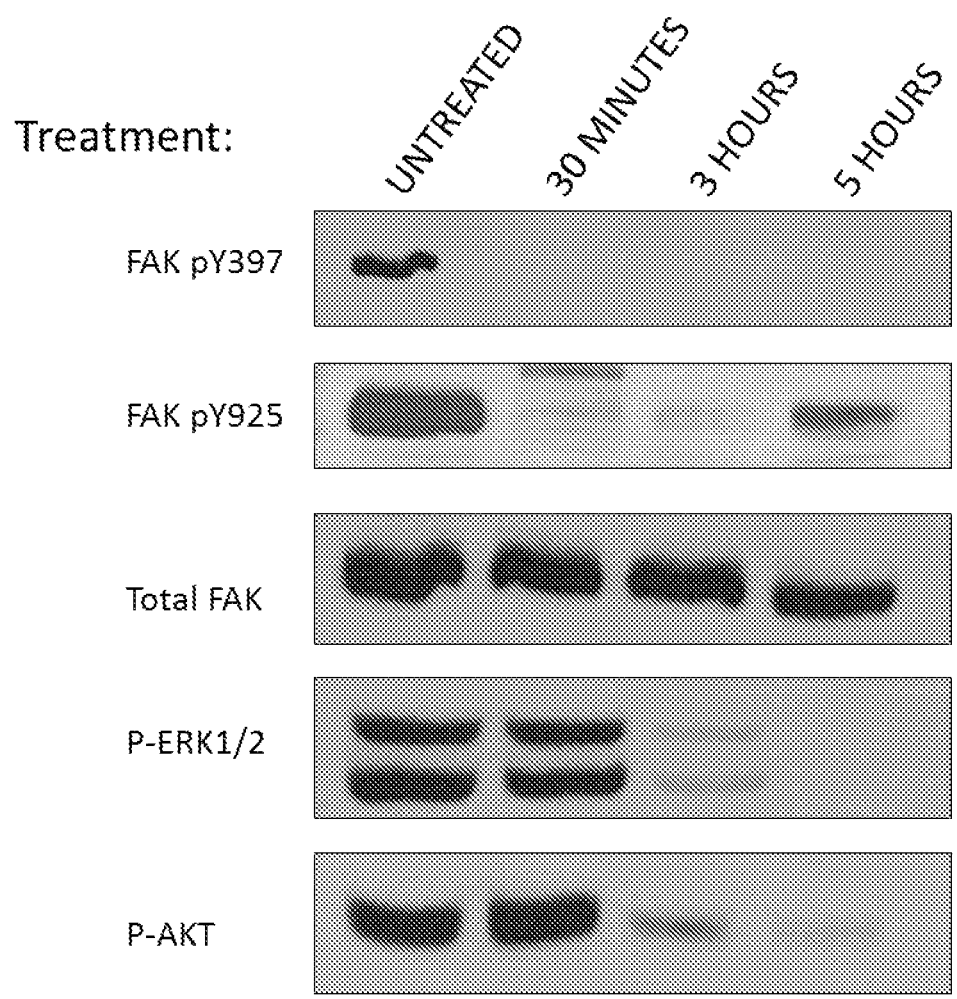

FIG. 27. FAK inhibitor effects on MAPK and PI3K pathways. Whole cell extracts were prepared using RIPA buffer for western blot in pre-leukemic IkE5$^{\Delta/\Delta}$ (Ikaros mut) cells. Status of MAPK signaling (p-ERK1/2) and PI3K signaling (pAKT) was examined in untreated and after treatment with FAK inhibitor (vs-6062 1 µm) for 30 minutes, 3 hours and 5 hours.

Figure 28:
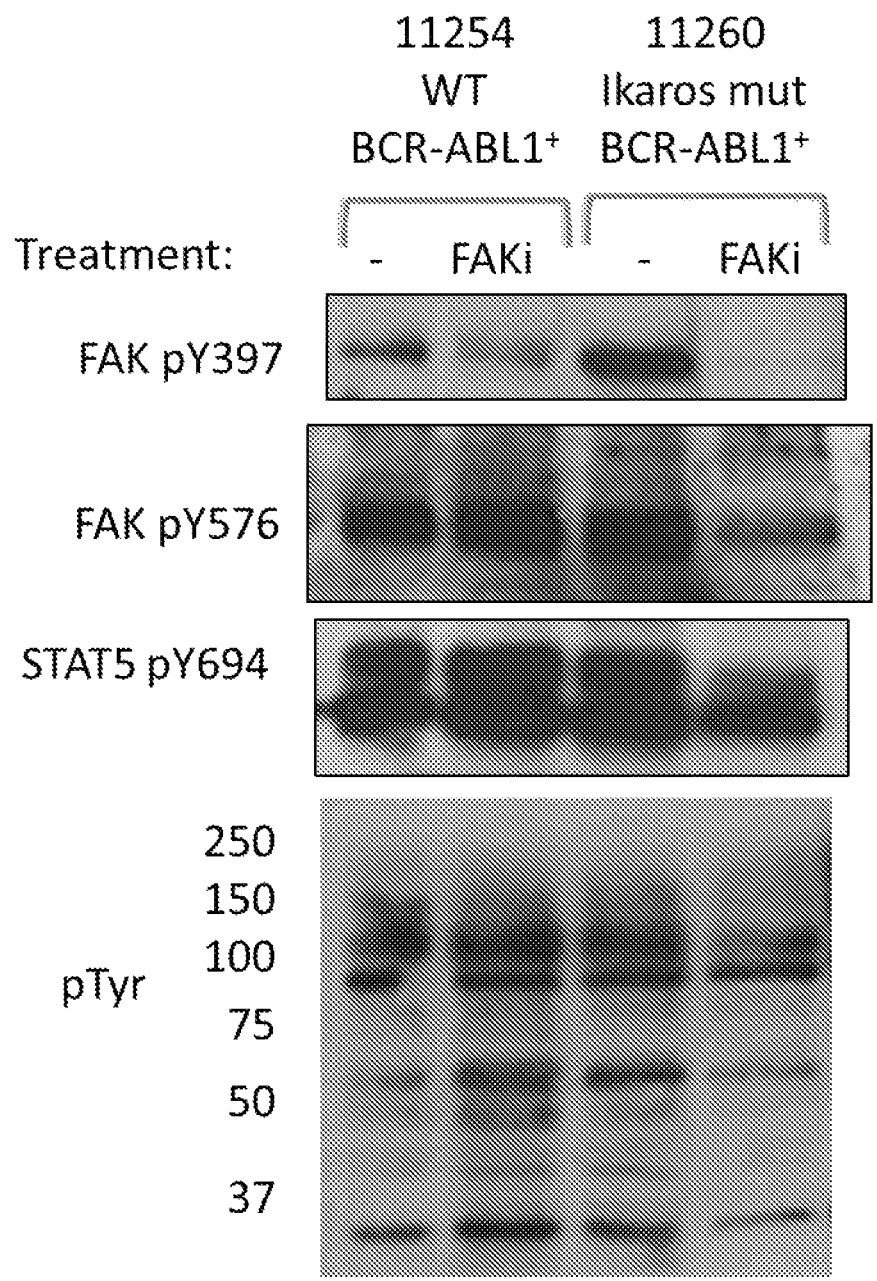

FIG. 28. Whole cell extracts were prepared using RIPA buffer for western blot in WT BCR-ABL1$^+$ (11254) and BCR-ABL1$^+$ IkE5$^{\Delta/\Delta}$ (11260) cells. Status of FAK signaling (p-Y397 and p-Y576), STAT5 signaling (pAKT) and Tyrosine kinase profile (pTyr) was examined in untreated and after treatment with FAK inhibitor (vs-6062 1 µM, FAKi).

DETAILED DESCRIPTION

The studies described herein define a key step in pre-B cell differentiation that is characterized by adherence to bone marrow stroma, self-renewal and proliferative expansion[36]. Normal pre-B cells transit rapidly through this stromal adherent phase and enter into a non-adherent phase in which self-renewal is lost, proliferation is diminished and differentiation into an Igκ-expressing cell is induced. Loss of Ikaros activity arrests pre-B cells in the adherent, self-renewing, pro-proliferative phase and promotes their transformation to a malignant state.

Figure 3A:
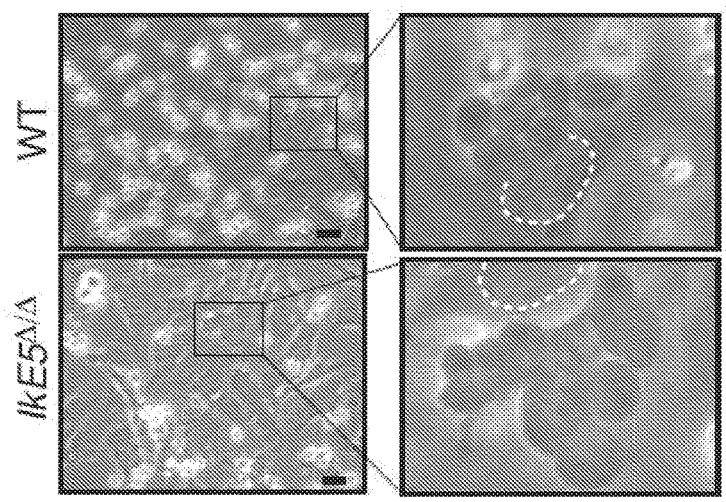
Figure 3B:
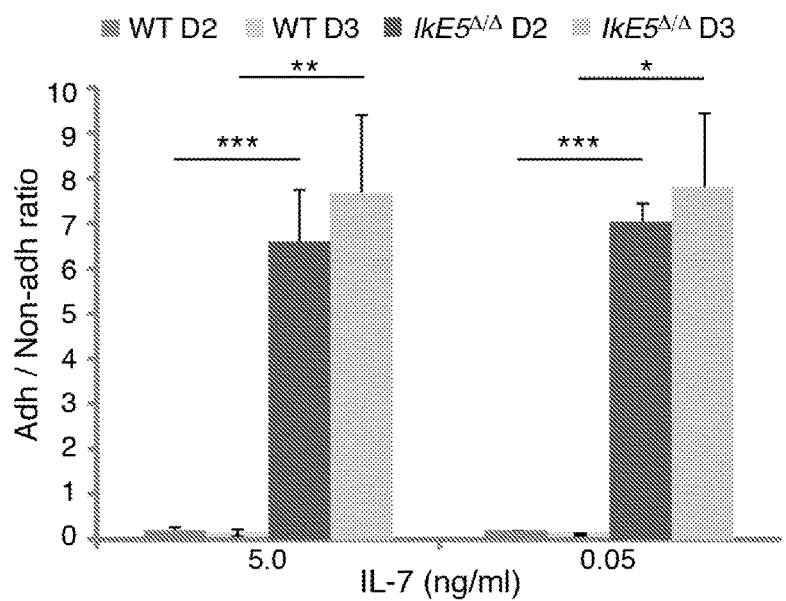
Figure 4A:
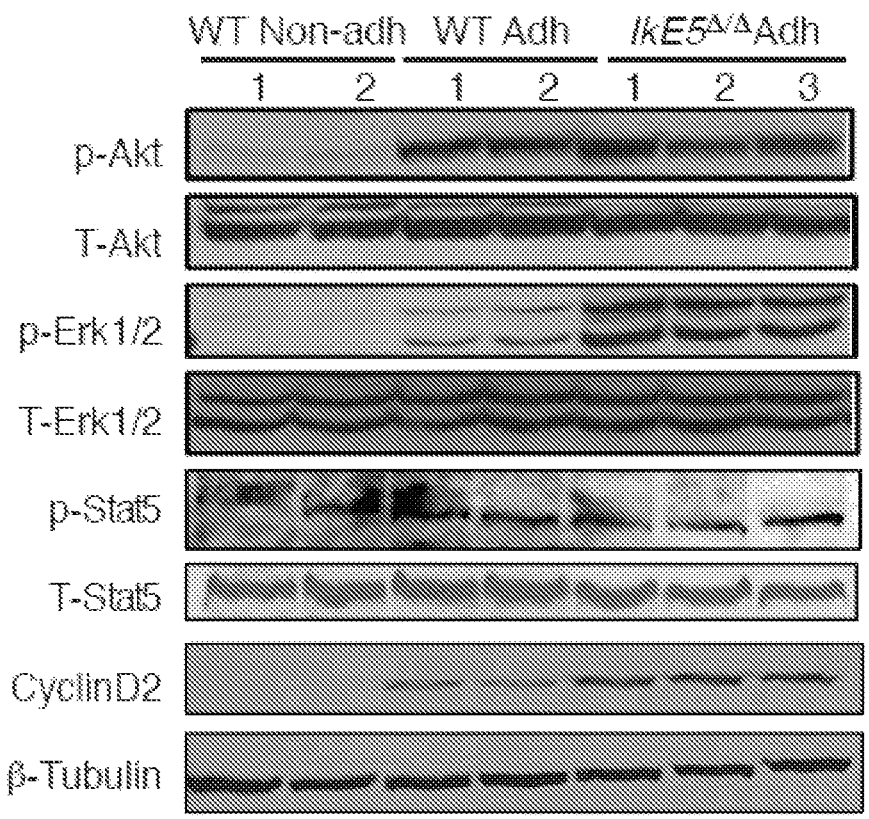
Figure 5A:
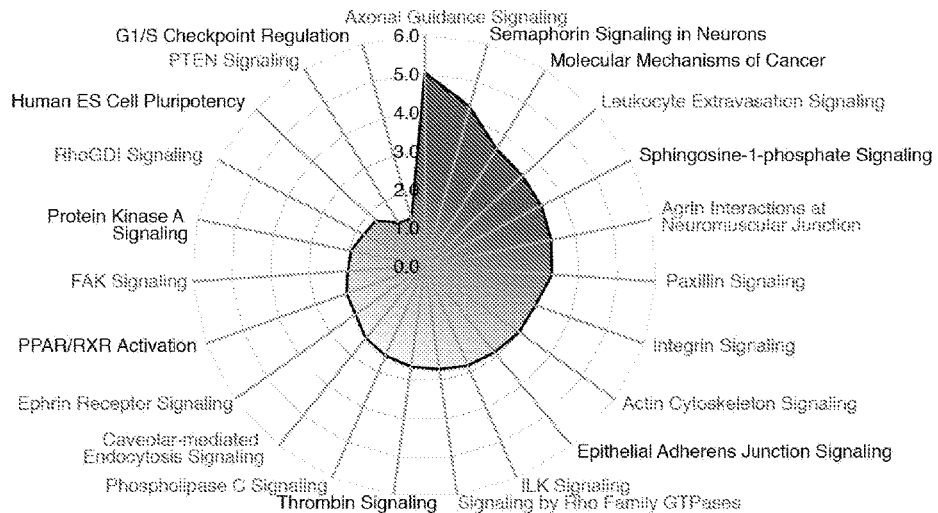

Ikaros-deficient large pre-B cells show increased expression of structural and signaling components of the focal adhesion and actin cytoskeleton pathways at both the transcription and protein level (FIG. 4A, B and FIG. 5A, B). Integrins (Itgb1, Itgb3, Itga9, Itga5), vinculin (Vcl), α-actinin (Actn1), myosins (Myo1b, Myl12b), FAK (Ptk2), and the Rac activating GEFRho guanine exchange factors (Arhgef12, Arhgef5), Rho GTPase activating protein 5 (Arhgap5), and Dedicator of cytokinesis (Dock1) were such examples. Extracellular matrix (ECM) components such as laminin (Lamb1), secreted phospho protein (Spp1) and matrix metallopeptidase 14 (Mmp14) were also induced in mutant pre-B cells. These transcriptional changes underscore a strong integrin-signaling environment that is demarcated by high levels of activated FAK (FIG. 5D-E), and a stable adhesion and re-adhesion phenotype to both stroma and integrin ligands (FIG. 3B, G). WT pre-B cells also demonstrate integrin-dependent adhesion; however, this is transient as the majority of adherent cells rapidly switch to a non-adherent phase and fail to re-adhere upon replating.

Integrins, engaged by the ECM, serve as signaling centers that control actin filament polymerization required for the formation and maturation of focal adhesions[42,43]. Recent studies suggest that actin also plays a role in organizing adhesion sites and the actin-integrin linkage composition can determine adhesion stability[44,45]. Cells that lack highly bundled actin structures, such as lymphocytes, have less prominent adhesions[46]. The actin cross-linker α-actinin, required for the formation of actin filaments[47], is upregulated in Ikaros deficient pre-B cells. Actin polymerization and disassembly are regulated by the opposing activities of the Rho and Rac small GTPases[48]. A potential increase in the Rac activating GEF Dock1 in Ikaros-deficient pre-B cells may contribute to the establishment of an actin environment that is conducive to integrin signaling. Given the low levels of $Ca^{2+}$ in adherent pre-B cells (FIG. 4C), recycling of adhesion structures, for example through calpain cleavage of talin, may be ineffective. Consistent with a stable focal adhesion environment, Ikaros-deficient pre-B cells failed to undergo SDF1-mediated chemotaxis in spite of normal or elevated expression of CXCR4 (Figure and do not exit the BM microenvironment. In this regard, a recent study reported increased chemotaxis of FAK-deficient pre-B cell precursors from the BM to the periphery[49] that is consistent with the observations herein of increased FAK activity in Ikaros-deficient pre-B cells and their inability to migrate from the BM to the periphery.

Figure 3C:
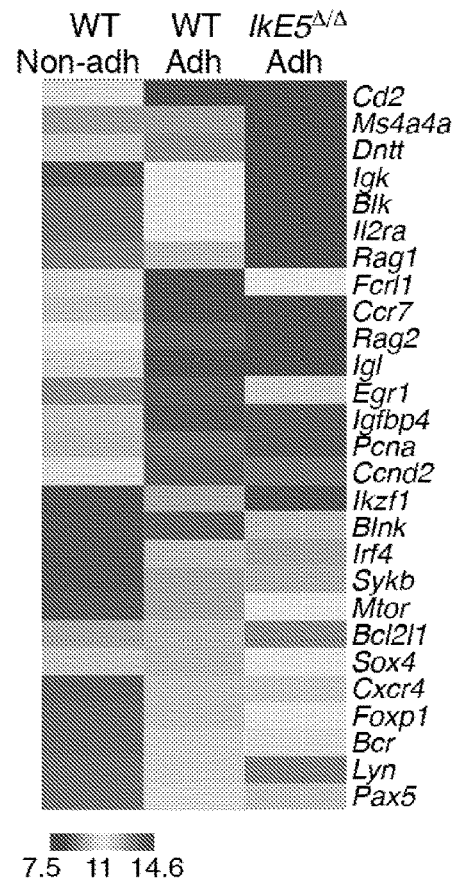

Notably, in WT pre-B cells, the pro-proliferative and differentiation-inducing arms of pre-BCR signaling are segregated away from one other and into the stromal-adherent and non-adherent phases of pre-B cell differentiation (FIG. 4A, B). The presence of IL-7R and pre-BCR together with active Erk1-2 MAPK and PI3K-Akt pathways in WT adherent pre-B cells indicates that receptor signaling is actively contributing to survival and proliferation. As WT pre-B cells detach from stroma, they rapidly turn off Erk1-2 and Akt signaling although expression of pre-BCR and IL-7R persists. An increase in p38 MAPK, Blnk and intracellular $Ca^{2+}$ is observed (FIG. 12B, C), together with a transcriptional induction of pre-B cell differentiation markers (FIG. 3C). A working model supported by these findings is that in addition to pre-BCR and IL-7R signaling, integrin-mediated adhesion and FAK signaling contribute to the proliferative expansion of early pre-B cells and provide limited self-renewal by keeping them engaged on stroma (FIG. 12A and FIG. 14). Another important effect of integrin signaling is to shut down the differentiation-inducing pathways in pre-B cells either directly or indirectly by promoting proliferation. As adhesion is lost, possibly due to recycling of focal adhesions, the negative effects on differentiation signaling are reduced. Increase in FAK activity has been implicated in the pathogenesis of a variety of cancers by engaging pro-proliferative signaling. Increased integrin and FAK signaling, as in Ikaros-deficient pre-B cells, may be responsible for augmenting self-renewal and proliferation and for further repressing differentiation at this critical developmental stage. A recent study has shown that loss of FAK during B cell differentiation causes a reduction in pre-B and immature B cells[49] and is consistent with the above-proposed model of integrin signaling in pre-B cell differentiation.

Figure 4B:
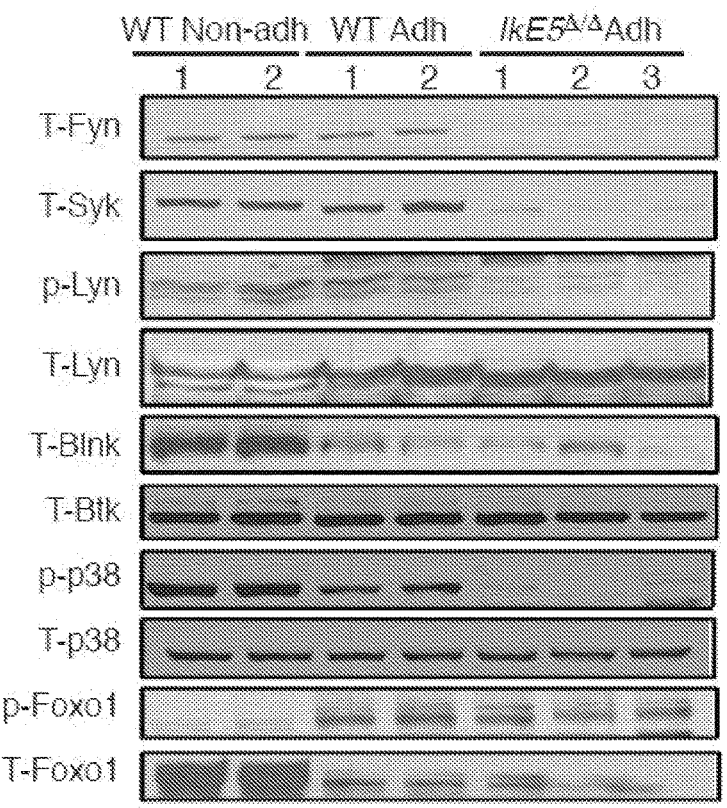

While integrin-mediated adhesion and activation of the downstream signaling effector FAK are augmented in Ikaros-deficient pre-B cells, all pre-BCR-affiliated PTKs are reduced (FIG. 4B). As transcription of these PTKs is relatively unperturbed, this effect is probably a consequence of altered protein stability. Feedback mechanisms originating from hyperactive FAK or MAPKs may stimulate degradation of these pre-BCR signaling effectors, thereby limiting the number of pro-proliferative signaling pathways operating in mutant pre-B cells. Loss in proximal pre-BCR signaling does not affect proliferation as this is also supported by other receptor signaling pathways such as growth factor receptors and integrins, but inhibits differentiation, which is solely dependent on the pre-BCR complex.

The switch from the pre-BCR-IL-7R signaling axis in normal pre-B cells to a more 'progenitor-like' integrin-growth factor signaling paradigm supports the survival and proliferative expansion of Ikaros-deficient pre-B cells. In fact, mutant pre-B cells cycle more rapidly, possibly due to a niche-mediated increase in MAPK and its downstream targets Cyclin D2 and CDK6. The ability of Ikaros-deficient pre-B cells to respond to different growth factors also highlights a potential to survive in different micro-environments. Aberrant expansion of mutant pre-B cells to non-physiological numbers represents the first step in a leukemic transformation process that evolves rapidly when the Ikaros-deficient pre-B cells are adoptively transferred to an immune-compromised bone marrow environment. However, the fact that the malignant precursor B-ALLs that develop are oligoclonal with respect to Igh gene rearrangement suggests that additional events are necessary for full malignant transformation. Whereas a subset of Igh rearrangements appears to be shared between leukemias arising in different recipients, this further suggests that some steps toward malignant transformation have occurred in the primary mice. Nonetheless, the Ikaros-deficient leukemic pre-B cell clones retain stromal-adherent properties and are still dependent for their survival on FAK activation.

The insights into the mechanisms that support normal pre-B cell differentiation and its aberrant manifestations described herein illuminate new strategies for the therapy of B-ALL that are linked to the underlying biology of the pre-B cell. Humans with IKZF1 mutant B-ALL have an inferior prognosis despite intensive treatment, which correlates with persistent residual disease following induction chemotherapy[23, 50]. Whereas inhibiting FAK causes detachment and death of Ikaros-deficient pre-B cells by depriving them from anchorage-dependent survival, it has little effect on WT pre-B cells. Hence, these and other pathways activated in Ikaros-deficient pre-B cells provide additional targets for therapeutic intervention in poor-prognosis B-ALL.

Ikaros (IKZF1) Mutations Associated with B-ALL

Human precursor B cell acute lymphoblastic leukemias (B-ALL) frequently display a pre-B cell phenotype, suggesting that a block at the pre-B cell proliferative stage may contribute to leukemogenesis[21]. Genome-wide studies in human leukemias have identified loss-of-function mutations in genes encoding regulators of B cell differentiation such as PAX5, TCF3, EBF1, and IKZF1 (IKAROS gene) in ~40% of samples from patients with precursor B-ALL[22]. Notably, IKZF1 mutations, including deletions in the Ikaros DNA-binding domain, were singled out as genetic lesions associated with B-ALL with poor prognosis[23-27]. Ikaros is a zinc-finger transcription factor that is required to induce transcription of lymphoid-specific genes in multi-potent progenitors, and its loss leads to developmental arrest prior to B cell lineage specification[28,29]. Ikaros, together with its family member Aiolos, which is induced after B cell lineage specification[30], have been implicated in promoting pre-BCR-mediated differentiation by repressing expression of the SLC of the pre-BCR complex[31]. IKZF1 deletions are present in about 15% of B-ALL cases, and typically result either in haploinsufficiency or expression of dominant-negative isoforms. These alterations have been shown to cooperate with Breakpoint cluster region-ABL1 (BCR-ABL1), which is generated by the der(22) of the t(9;22) (q34;q11) translocation, or Philadelphia (Ph) chromosome, in the induction of lymphoblastic leukemia and to promote resistance to therapy in experimental models of BCR-ABL1 ALL (Virely et al., Leukemia. 24(6):1200-1204 (2010)), though IKZF1 alterations are associated with poor prognosis in both BCR-ABL1-positive and negative ALL cases (Mullighan et al., Nature. 453(7191):110-114 (2008); Iacobucci et al., Blood. 114(10):2159-2167 (2009); Martinelli et al., J Clin Oncol. 27(31):5202-5207 (2009); Mullighan et al., J Clin Invest. 122(10):3407-3415 (2012)). IKZF1 alterations are present in up to one-third of high-risk B-ALL cases and triple the risk of treatment failure (Mullighan et al., N Engl J Med. 360(5):470-480 (2009); Kuiper et al., Leukemia 24(7):1258-1264 (2010)). Mutations in IKZF1 are associated with increased risk of childhood ALL; see Papaemmanuil et al., Nat Genet. 41(9):1006-1010 (2009). The sequence of the IKZF1 gene is available in GenBank at NC_000007.13 (Reference GRCh37.p13 Primary Assembly); differences from this reference sequence that are associated with B-ALL, e.g., with the presence or increased risk of B-ALL, include those described in the foregoing references. Methods of detecting mutations in IKZF1 are known in the art and described, e.g., in US 20130345091, which is incorporated herein in its entirety. For example, mutations in IKZF1 can be detected by detecting in blood samples from a subject a change in an Ikaros isoform pattern (i.e., a different isoform from normal Ikaros1 and Ikaros2, e.g., an increase in levels or the presence of shorter isoforms lacking DNA binding and therefore lacking activity of Ikaros). This can be detected by detecting the presence of shortened forms of the transcript (e.g., using sequencing, PCR, RNAseq, whole exome sequencing (WES), whole genome sequencing (WGS), exon-scanning PCR, or Fluorescence in situ hybridization (FISH)) or shortened forms of the Ikaros protein (e.g., using antibody-based methods such as Western blot or immunostaining). In addition, subcellular localization can be used, as shorter Ikaros isoforms stay in the cytoplasm when overexpressed; thus, immunofluorescence or other methods that can detect subcellular localization can be used. The methods described herein can include identifying subjects who have germline or tumor cell mutations in IKZF1 that result in haploinsufficiency or expression of dominant-negative isoforms.

Focal Adhesion Kinase (FAK)

FAK, also known as PTK2 protein tyrosine kinase 2 (PTK2), is encoded by the PTK2 gene in humans (sequences below). FAK is concentrated in the focal adhesions that form between cells growing in the presence of extracellular matrix constituents. FAK activation relies upon autophosphorylation of Y-397 in the N-terminal domain; thus, detection of the phosphorylated Y-397 form of FAK (referred to herein as pFAK) is a reasonable proxy for detection of FAK activity. FAK has been shown to be upregulated in several types of cancer including brain, thyroid, head and neck, lung, kidney, hepatocellular, pancreatic, colorectal, breast, cervical, ovarian, and prostate cancers, as well as melanoma, neuroblastoma, osteosarcoma, and sarcoma (see Dunn et al., Anticancer Agents Med Chem. 10(10): 722-734 (2010)).

FAK Gene Sequences

Although several transcript variants encoding different isoforms have been found for the PTK2 gene, the full length sequences of only three of them have been determined, as shown in Table 1; notes in Table 1 are from NCBI GenBank.

TABLE 1

| Name | GenBank Accession No. | |
|---|---|---|
| | cDNA | Protein |
| focal adhesion kinase 1 isoform a | NM_005607.4 variant (1) differs in the 5' UTR and coding sequence compared to variant (2) | NP_005598.3 isoform (a) is shorter at the N-terminus compared to isoform b. |
| focal adhesion kinase 1 isoform b | NM_153831.3 Variant (2) encodes the longest isoform (b) | NP_722560.1 Isoform (b) is the longest |
| focal adhesion kinase 1 isoform c | NM_001199649.1 Variant (3) differs in the 5' UTR and coding sequence, and contains two additional in-frame segments near the 3' end of the coding sequence, compared to variant 2 | NP_001186578.1 Isoform (c) is shorter at the N-terminus and contains two additional segments in the C-terminus compared to isoform b. |

Anti-FAK Antibodies

The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, Making and Using *Antibodies: A Practical Handbook* (CRC Press; 1st edition, Dec. 13, 2006); Kontermann and Dübel, *Antibody Engineering Volume* 1 (*Springer Protocols*) (Springer; 2nd ed., May 21, 2010); Lo, *Antibody Engineering: Methods and Protocols* (*Methods in Molecular Biology*) (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010).

Antibodies that bind selectively to FAK, or to the activated pFAK, are known in the art and are commercially available, e.g., from EMD Millipore, R&D Systems, OriGene, QIAGEN, GenScript, Cell Signaling Technology, SABiosciences, Novus Biologicals, Sino Biological, Enzo Life Sciences, Abcam, ProSpec, Cloud-Clone Corp., Thermo Fisher Scientific, and LSBio.

The antibody can be coupled to a detectable or imaging agent. Such agents are well known in the art and include bioluminescent or fluorescent labels (e.g., GFP, FITC, rhodamine, or Texas Red), radioactive isotopes, and colorimetric/enzymatic agents (e.g., HRP, B-galactosidase).

Assays for FAK Activity

A number of assays known in the art can be used to detect FAK activity; as noted above, FAK activation relies upon autophosphorylation of residue Y-397; thus, detection of pFAK is a reasonable proxy for detection of FAK activity. pFAK can be detected, e.g., using an antibody that binds specifically to the phosphorylated Y-397 form of FAK; such antibodies can be used in Western blot, ELISA, immunoprecipitation, immunofluorescence, or immunohistochemical assays. Other methods known in the art, e.g., radiolabeling of the phosphorylated form using $^{32}P$, can also be used. Kits for detecting FAK activity are commercially available, e.g., from Life Technologies, TebuBIO, AbCam, and others.

Methods of Diagnosis

Included herein are methods for diagnosing leukemias, e.g., B-ALL, that are associated with hyperactivation of the Ikaros-FAK pathway. The methods include obtaining a sample containing B cells from a subject, evaluating the presence and/or level of FAK activity in the sample, and comparing the presence and/or level with one or more references, e.g., a control reference that represents a level of FAK activity in a normal B cell, e.g., a level in a B cell from an unaffected subject (e.g., in normal mature peripheral blood B cells), and/or a disease reference that represents a level of FAK activity associated with leukemia, e.g., a level in a B cell harboring a mutation in IKZF1 that results in hyperactivation of the Ikaros-FAK pathway. In some embodiments, the level is considered a threshold level, and the presence of a level of FAK activity above the threshold indicates that the subject has leukemia. In some embodiments, the threshold is the same as the level of detectability of the assay used, and the presence of detectable activity indicates that the subject has, or is at risk of developing, leukemia.

The sample can be, e.g., a biological fluid or tissue such as blood or a bone aspirate or biopsy specimen, samples of other tissues including lymph nodes, cerebrospinal fluid, and effusions (body fluid collections).

B cells can be identified using methods known in the art, e.g., based on the presence of cell surface markers such as TdT+ve CD10+ve CD19+ve (TdT is terminal deoxynucleotide transferase) for humans (and optionally CD22+ve and/or CD79a+ve), or CD19+ve B220+ve BP1+ve for mice; cell surface markers for other species are known in the art. Cell sorting methods such as FACS or microfluidics can be used to select, identify, or enrich B cells in a sample.

In some embodiments, the presence and/or level of FAK activity is comparable to the presence and/or level of the protein(s) in the disease reference, and the subject has one or more symptoms associated with leukemia, then the subject is diagnosed with leukemia, e.g., B-ALL. In some embodiments, the subject has no overt signs or symptoms of leukemia, but the presence and/or level of FAK activity is comparable to the presence and/or level of the protein(s) in the disease reference, then the subject has an increased risk of developing leukemia.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein (e.g., leukemia, e.g., B-ALL).

A disease reference subject is one who has (or has an increased risk of developing) leukemia, e.g., B-ALL. An increased risk is defined as a risk above the risk of subjects in the general population.

Thus, in some cases the level of FAK activity (or of pFAK) in a subject being less than a reference level of FAK activity is indicative of a clinical status (e.g., indicative of the absence of leukemia, e.g., the absence of B-ALL, or a low risk of developing B-ALL as compared to a subject who has a level of FAK activity above the reference level). In some cases the level of FAK activity (or pFAK) in a subject being greater than or equal to the reference level of FAK activity (or pFAK) is indicative of the presence of leukemia, e.g., the presence of B-ALL, or an increased risk of developing B-ALL as compared to a subject who has a level of FAK activity below the reference level; these subjects might be considered to have "smouldering" B-ALL and have a high likelihood of developing the disease within weeks to months, even if at present they do not have full-blown leukemia (e.g., >5% blasts in the bone marrow).

In some embodiments, the subject has had B-ALL associated with hyperactivation of the Ikaros-FAK pathway but has achieved remission after therapy (e.g., after chemotherapy), and the presence of a level of FAK activity below a reference level indicates that remission continues or that the subject has a low risk of relapse in the near term (e.g., within the next two weeks, month, six months, year, or two years); in these subjects, the presence of a level of FAK activity above a reference level can indicate that the subject has had or is about to have a relapse, e.g., the subject has a high risk of relapse in the near term (e.g., within the next two weeks, month, six months, year, or two years).

In some embodiments, the amount by which the level in the subject is greater than the reference level is sufficient to distinguish a subject from a control subject, and optionally is statistically significantly greater than the level in a control subject. In cases where the level of FAK activity in a subject being equal to the reference level of FAK activity, the "being equal" refers to being approximately equal (e.g., not statistically different).

The predetermined value can depend upon the particular population of subjects (e.g., human subjects) selected. For example, an apparently healthy population will have a different 'normal' range of levels of FAK activity (or pFAK) than will a population of subjects that have, or are likely to have, leukemia. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

In some embodiments, as an alternative to or in addition to detecting FAK activation, the methods include detecting the presence of one or more Ikaros (IZKF1) mutations that are associated with the presence of or increased risk of developing B-ALL, as are known in the art (see above).

Methods of Treatment

In some embodiments, once it has been determined that a person has leukemia, e.g., B-ALL, or has an increased risk of developing leukemia, e.g., B-ALL, then a treatment as described herein can be administered.

A diagnosis can be made, e.g., using methods known in the art, e.g., based on morphologic, immunophenotypic, and genetic features that allow the differentiation of normal B-cell progenitors from hematopoietic and non-hematopoietic neoplasms; see, e.g., Margolin et al., "Acute lymphoblastic leukemia." In: Pizzo P A, Poplack D G, eds.: Principles and Practice of Pediatric Oncology. 6th ed. Philadelphia, Pa.: Lippincott Williams and Wilkins, 2011, pp 518-65; Chessells, Br J Haematol 114 (3): 506-11, 2001; Onciu, Hematol Oncol Clin North Am 23 (4): 655-74, 2009; Heerema-McKenney et al., "Pathology and molecular diagnosis of leukemias and lymphomas." In: Pizzo P A, Poplack D G, eds.: Principles and Practice of Pediatric Oncology. 6th ed. Philadelphia, Pa.: Lippincott Williams and Wilkins, 2011, pp 138-63.

In some embodiments, e.g., as an alternative or in addition, the determination that a subject has, or has an increased risk of developing, leukemia (e.g., B-ALL) is made using a method described herein, e.g., based on the presence of levels of FAK activity above a threshold, or based on the presence of a mutation in IKZF1 that results in hyperactivation of the Ikaros-FAK pathway, or loss of wild-type Ikaros expression.

Once a subject has been identified as having (or being at increased risk of developing) leukemia e.g., B-ALL, then a treatment as known in the art or described herein can be administered.

Conventional Treatments

In some embodiments, once the presence of FAK activity above a reference levels in a subject is determined, a conventional treatment for B-ALL is administered to the subject. Generally, the treatment will include induction, consolidation and maintenance therapy along with CNS prophylaxis (see, e.g., Seiter et al., "Acute Lymphoblastic Leukemia Treatment Protocol," Medline, 2013 available at emedicine.medscape.com/article/2004705-overview; Larson et al., Blood. Apr. 15, 1995; 85(8):2025-37; Rowe et al., Blood. Dec. 1, 2005; 106(12):3760-7; Thomas et al., J Clin Oncol. Oct. 15, 2004; 22(20):4075-86; Cortes et al., Blood. Sep. 15, 1995; 86(6):2091-7; and Kantarjian et al., Cancer. Dec. 15, 2004; 101(12):2788-801.

Induction therapy typically includes administration of combinations of drugs, e.g., vincristine, prednisone or dexamethasone, cyclophosphamide, doxorubicin, and L-asparaginase, given over 4-6 weeks. After that, consolidation (intensification) multiagent therapy additionally, including cytarabine and methotrexate is given; radiation or surgical treatment is typically not given to patients in the induction phase. Maintenance therapy includes 6-mercaptopurine, methotrexate, steroids, and vincristine. Intrathecal (IT) methotrexate is often administered as a CNS prophylaxis, given the high risk of CNS involvement. Treatment regimens include CALGB [Cancer and Leukemia Group B]-8811 and hyper-CVAD (hyperfractionated cyclophosphamide, vincristine, doxorubicin, and dexamethasone) regimens and the ALL-2 regimen) plus the addition of tyrosine kinase inhibitors for Philadelphia chromosome-positive ALL and rituximab for CD20-positive ALL; pediatric regimens include GRAALL-2003; COG AALL-0434; CCG-1961; CALGB 10403; and the DFCI regimen.

In some embodiments, the treatment can include allogeneic hematopoietic stem cell transplantation, which is indicated as post-remission treatment for eligible high-risk B-ALL patients, including those with Ph+ or IKZF1-mutant disease.

FAK Inhibitors

In some embodiments, the methods described herein include administering one or more FAK inhibitors or any pharmaceutically acceptable salt thereof, alone or in combination with a conventional treatment as described herein or known in the art; useful inhibitors include small molecules, inhibitory nucleic acids that reduce expression of FAK, and dominant negative FAK proteins. A number of FAK inhibitors are known in the art and include Compound C4 (chloropyramine hydrochloride; see Kurenova et al., Oncotarget. 2013 October; 4(10): 1632-1646; Ma, Anticancer Agents Med Chem. 2011 September; 11(7):638-42; FAK Inhibitor 14; Masitinib; PF 562271 (N-methyl-N-(3-(((2-((2-oxoindolin-5-yl)amino)-5-(trifluoromethyl)pyrimidin-4-yl)amino)methyl)pyridin-2-yl)methanesulfonamide; Roberts et al., Cancer Res., 68: 1935-44, 2008); PF 431396 (N-Methyl-N-[2-[[[2-[(2,3-dihydro-2-oxo-1H-indol-5-yl)amino]-5-(trifluoromethyl)-4-pyrimidinyl]amino]methyl]phenyl]methanesulfonamide); PF 573228 (3,4-Dihydro-6-[[4-[[[3-(methylsulfonyl)phenyl]methyl]amino]-5-(trifluoromethyl)-2-pyrimidinyl]amino]-2(1H)-quinolinone); PF-00562271, the benzenesulfonate salt of PF-562271; VS-4718; PF-04554878 (also known as VS-6063 and defactinib, CAS#1345713-71-4); AG82; a 7H-pyrrolo[2,3-d]pyrimidine; GSK2256098; BI1853520;

TAE-226 (Shi et al., Mol Carcinog 2007, 46:488-96); ME-TAE-226; NVP-TAE-226; FRNK; PND-1186 (US20120196858 and WO 2008115369); TAC-544; 1,2,4,5-Benzenetetraamine terrahydrochloride (Golubovskaya et al., J Med Chem 2008, 51:7405-16); 2-[(5-chloro-2-[[3-methyl-1-(1-methylethyl)-1H-pyrazol-5-yl]amino]-4-pyridinyl)amino]-N-methoxybenzamide; and the 2,4,5-substituted pyrimidines described in US 20130324532.

See also, e.g., WO 2008115369; WO2010062578; WO 2011133668; WO 2012110774; US20130296312; US20130324546; US20130017194; EP 2190834; US20130158005; WO2012045194; Stokes et al., Mol Cancer Ther. 2011 November; 10(11):2135-45 (describing use of PF-562271); Schultze and Fiedler, Anticancer Agents Med Chem. 2011 September; 11(7):593-9 (describing clinical trials of orally available selective small molecule inhibitors PF-562-271, PF-04554878 and GSK2256098); Ma et al., Drugs Fut 2009, 34(6): 477; Slack-Davis et al., J Biol Chem 2007, 282:14845-52. Additional FAK inhibitors can be identified, e.g., using assays known in the art, e.g., as described in EP1546372.

Dominant negative forms of FAK are known in the art and can also be used in the methods described herein. For example, a dominant-negative, C-terminal domain of FAK (FAK-CD) (677-1052 amino acids) is described in Golubovskaya et al., BMC Cancer. 2009 Aug. 12; 9:280. Alternatively or in addition, a dominant-negative FAK-related nonkinase (FRNK) or Hsp90 inhibitor (e.g., 17-DMAG) can also be used to inhibit FAK; see, e.g., WO2005014835 and Schwock et al., Cancer Res. 2009 Jun. 1; 69(11):4750-9. See also Beviglia et al 2003, Biochem J. 373:201-210; Smith et al 2005, Melanoma Res. 15:357-362; and Haider et al 2005, Clin. Cancer Res. 11:8829-8836).

Small inhibitory nucleic acid inhibitors of FAK can also be used. Inhibitory nucleic acids for use in practicing the methods described herein can be antisense oligonucleotides or those which inhibit post-transcriptional processing of FAK, such as an interfering RNA, including but not limited siRNA or shRNA. See, e.g., Bryant et al., Biol Open. 2012 Aug. 15; 1(8):723-30, which showed abolition of FAK expression using stable (shRNA) or transient (siRNA) approaches. One of skill in the art would readily be able to design and use such small inhibitory nucleic acids.

Antisense

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to FAK (PTK2). Thus, oligonucleotides are chosen that are sufficiently complementary to the target, i.e., that hybridize sufficiently well and with sufficient specificity to give the desired effect, while striving to avoid significant off-target effects.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridisable. A complementary nucleic acid sequence of the invention is specifically hybridisable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The antisense oligonucleotides useful in the methods described herein have at least 80% sequence complementarity to a target region within the target nucleic acid, e.g., 90%, 95%, or 100% sequence complementarity to the target region within miR-33a/b (e.g., a target region comprising the seed sequence). For example, an antisense compound in which 18 of 20 nucleobases of the antisense oligonucleotide are complementary, and would therefore specifically hybridize, to a target region would represent 90 percent complementarity. Percent complementarity of an antisense compound with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention, which hybridize to FAK (PTK2) mRNA, are identified through experimentation, and representative sequences of these compounds are hereinbelow identified as preferred embodiments of the invention. In general the antisense oligonucleotides must retain specificity for their target, i.e., must not directly bind to, or directly significantly affect expression levels of, transcripts other than the intended target.

siRNA

In some embodiments, the nucleic acid sequence that is complementary to FAK (PTK2) mRNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sci. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid (i.e., a target region comprising the seed sequence of miR-33 a and/or b) are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Combination Therapy

In some embodiments, the methods include administration of a combination therapy, e.g., comprising administering a FAK inhibitor with one or more of the conventional treatments listed above, and/or one or more glucocorticoids (e.g., prednisone or dexamethasone) and/or kinase inhibitors, e.g., BCR-ABL1 inhibitors in Ph+, and/or inhibitors of other tyrosine kinases, e.g., that are activated in Ph– human B-ALL disease such as inhibitors of JAK-STAT (Janus associated kinase-signal transducer and activator of transcription) pathway, e.g., Janus kinase 2 (JAK2).

ABL1 inhibitors include tyrosine kinase inhibitors such as dasatinib, imatinib, nilotinib, bosutinib, ponatinib, bafetinib, and 1,3,4 thiadiazole derivatives (e.g., having the following structure:

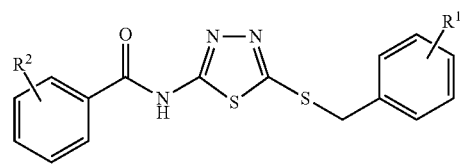

6a-u as described in Radi et al., Bioorg Med Chem Lett 2008, 18(3):1207-1211), or in US20100249152).

JAK/STAT inhibitors include INCB018424 (Ruxolitinib); SAR302503 (TG101348); CEP-701 (Lestaurtinib); CYT387; SB1518 (pacritinib); LY2784544; XL019; AZD1480; BMS-911543; and NS-018. See, e.g., Furqan et al., Biomarker Research 2013, 1:5 doi:10.1186/2050-7771-1-5.

Aurora Kinase Inhibitors can also be used and include PHA-739358 (Danusertib), MLN8054, and AZD1152.

Asparaginase can also be used, e.g., L-ASP, PEG-ASP, or Asparaginase *Erwinia Chrysanthemi*, or L-asparaginase-loaded red blood cells (GRASPA®).

Monoclonal antibodies (MoAbs) can also be used, e.g., anti-CD20 (rituximab), or anti-CD22 (e.g., epratuzumab or inotuzumab, e.g., inotuzumab ozogamicin), or bi-specific MoAbs, e.g., blinatumomab, a CD3/CD19 bi-specific MoAb.

Other combination treatments can include mammalian target of rapamycin (mTOR) inhibitors (e.g., rapamycin and rapalogs such as temsirolimus (CCI-779), everolimus (RAD001), and ridaforolimus (AP-23573); or ATP-competitive mTOR kinase inhibitors such as NVP-BEZ235, BGT226, SF1126, PKI-587, INK128, AZD8055, and AZD2014); and purine analogs, e.g., clofarabine, forodesine, and nelarabine.

In some embodiments, the methods also include administration of canertinib (Irwin et al., PLoS One. 2013; 8(8): e70608); BMS-214662; and/or KW-2449 (Shiotsu et al., Blood. 2009 Aug. 20; 114(8):1607-17).

In some embodiments, the methods include administration of a standard multiagent chemotherapy regimen (e.g., CALGB 8811 (daunorubicin, vincristine, prednisone, pegaspargase, and cyclophosphamide))

In some embodiments, the methods further include allogeneic hematopoietic stem cell transplantation, e.g., as post-remission treatment, e.g., for eligible high-risk B-ALL patients, including those with Ph+ or IKZF1-mutant disease.

EXAMPLES

The invention is further described in the following examples, which do not limit the scope of the invention described in the claims.

Materials and Methods

The following materials and methods were used in the Examples set forth below.

Mice. The IkE5$^{fl/fl}$ mouse line was generated by inserting loxP sites flanking the Ikzf1 exon 5 by a standard gene targeting method. CD2-Cre and CD19-Cre transgenic lines were obtained from Drs. D. Kioussis and K. Rajewsky, respectively. All mice were bred and maintained under pathogen-free conditions in the animal facility at Massachusetts General Hospital, Bldg. 149-8. At the time of analysis, mice were 5-9 wk of age. All animal experiments were done according to protocols approved by the Subcommittee on Research Animal Care at Massachusetts General Hospital (Charlestown, Mass.) and in accordance with the guidelines set forth by the National Institutes of Health.

Antibodies. Antibodies for bone marrow lineage depletion and flow cytometry were purchased from BD Pharmingen, Southern Biotech and eBiosciences. In some cases, hybridoma supernatant containing antibodies against Mac-1, Gr-1, TER119, c-Kit and CD3ε were used. Antibodies and the specific clones used were: CD3 (17A2), CD8α (53-6.7), TCRβ (H57-597), Mac-1 (M1/70), DX5, Gr-1 (RB6-8C5), Ter119 and IgM (R6.60-2 or 11/41), FcγRII/III (2.4G2), CD19 (1D3), c-Kit (ACK2 or 2B8) BP1 (FG35.4), CD43 (S7), CD2 (RM2-5), Ig kappa (187.D), Integrin α5 (HMa5-1), Integrin α6-PE (GoH3) and Integrin β1 (9EG7). For immunoblotting and immunofluorescence, antibodies from Cell signaling technologies raised against the phosphorylated and total protein for Akt (4060/4685), Erk (4377/4695), p38 (4511/8690), Stat5 (9351), Lyn (2731/2796), Syk (12358), FAK (3283/8556/3285), Foxo1 (2880/9454), Fyn (4023), Blnk (12168), Btk (8547), and Cyclin D2 (3741) were utilized. Antibodies against total Stat5 (sc-835X), β-tubulin (sc-9104) and Blk (K-23) were purchased from Santa Cruz Biotechnology.

Flow Cytometry and Cell Sorting. Bone marrow (BM) cells were isolated as previously described[51]. Briefly, BM cells were harvested from femurs and tibias and subjected to red blood cell (RBC) lysis using ACK buffer (0.15 M ammonium chloride, 10 mM potassium bicarbonate, 0.1 mM EDTA). For large pre-B cell isolation, bone marrow cells were depleted with antibodies against Ter119, Mac-1, Gr-1, IgM, CD3, CD8a, TCRβ, DX5 and positive cells removed with magnetic beads conjugated to goat anti-rat IgG (QIAGEN). Remaining cells after depletion were labeled with various fluorochrome-conjugated mAbs against B-cell markers for phenotypic analysis, and CD19$^+$CD43$^+$ BP1$^+$ cells were sorted as large-preB cells, for in vitro cultures and RNA-seq analysis and CD19$^+$CD43– CD25$^+$ as small pre-B cells for RNA-seq analysis. The BP1$^+$ fraction of the CD19$^+$CD43$^+$ population expressed lower levels of c-Kit in both WT and IkE5$^{Δ/Δ}$ pre-B cells. For analysis of immature IgM$^+$ cells, undepleted BM cells were stained with mAbs against CD19 and IgM and analyzed within the lymphoid population by electronic gating based on size and granularity. For flow cytometry of integrins, cells were stained with either phycoerythrin (PE) conjugates or primary antibody followed by PE-conjugated secondary antibody. Antibody to P-FAK 925 was used for flow cytometry (Cell Signaling, 3284). Flow cytometric analysis was performed using a two-laser FACSCanto™ (BD) or a three-laser MoFlo® (Dako Cytomation). Cell sorting was performed using a three-laser MoFlo®. The resulting files were uploaded to FlowJo (Tree Star) for further analysis.

Intracellular Staining. Large Pre B cells were fixed with 2% paraformaldehyde (Electron Microscopy Sciences, PA, USA) in PBS at room temperature for 20 min. After two washes with PBS, the cells were subsequently permeabilized with 0.5% saponinin 2% FCS/PBS for 20 minutes at 4° C. The cells were stained with FITC-conjugated anti-μ or anti-κ antibody for additional 30 min at 4° C., then washed twice in 2% FCS-PBS before analysis on a FACSCanto™ (BD). For intracellular staining for p-FAK, fixed cells were permeablized with 90% methanol for 2 hours and washed. The cells were then incubated with primary antibody for 30 minutes. Cells were washed and incubated with FITC-conjugated secondary antibody for an additional 30 minutes at 4° C. washed and analyzed by flow cytometry.

Immunoglobulin Gene Rearrangement Analysis. DNA was isolated from sorted large pre-B cells and analyzed for immunoglobulin heavy and light chain gene rearrangements by PCR approach using primers specific for D-J and V-DJ or V-J rearrangements as described before[52, 53]. Briefly, For D-J$_H$ rearrangement, the DH sense primer was used with a JH3 antisense primer. V-DJ rearrangements were evaluated using a mixture of three different degenerate (at three positions) oligonucleotides homologous to sequences in the conserved framework region 3 (FR3) of the indicated VH gene families and the JH3 antisense primer. For PCR, serial dilutions (1× and 1:3) of the samples were heated to 94° C. for 5 min and then subjected to amplification for 35 cycles of 1 min at 94° C., 1 min at 60° C., and 1 min 30 sec at 72° C. After the last cycle, a final extension step at 72° C. for 10 min was carried out. PCR products were run on 1% agarose gels, transferred and hybridized with probe upstream of the JH3 primer region. For analysis of the Igκ V-J rearrangement, PCR amplification was performed with Vκ sense primer mixture that is degenerate at four positions and Jκ5 antisense oligo. Southern hybridization of PCR-products for V-J rearrangement was performed with probes binding upstream of the Jκ5 region.

Stromal-Free Cultures. Differentiation in stromal-free cultures was performed as previously described[54]. Briefly, 2×10$^3$ sorted large pre-B cells were plated in opti-MEM media (Gibco) for 4 days (d4) supplemented with 10% FCS, 50 μM 2-ME, 2.4 g/L NaHCO3, 100 μg/ml penicillin, 100 μg/ml streptomycin and 5 ng/ml of IL-7 (Peprotech). At day 4, cells were washed and re-plated in opti-MEM with 2% FCS and 0.05 ng/ml IL-7. After 3 days, cells were harvested, counted and stained for cell surface expression of CD19, BP1, IgM and CD2. For addressing survival and proliferation, large pre-B cells were cultured without stroma for 1-3 days in 0.05-5 ng/ml of IL-7. Cells were harvested and analyzed for counts, cell cycle and apoptosis.

Stromal Cultures. WT and IkE5$^{Δ/Δ}$ sorted large pre-B cells were co-cultured with OP9 stroma in DMEM media (Sigma, D-5671) supplemented with 10% FBS (Sigma, 2442), 50 μM 2-M, 100 μg/ml penicillin, 100 μg/ml streptomycin, 1× Glutamax (Gibco 35050-062), 10 mM HEPES (Gibco, #156-30-80) and 1× Sodium Pyruvate (Gibco, 11360-070) in the presence of indicated amounts of IL-7 as previously described[51]. Equal number of WT and IkE5$^{Δ/Δ}$ pre-B cells plated in presence of IL-7 were harvested for counts, cell cycle, proliferation and apoptosis at indicated time points. All analysis on cultured large pre-B cells was performed after removal of the OP9-GFP by flow cytometry. Exclusion by electronic gating based on size and granularity was performed.

For calculation of adherent/non-adherent ratios, $5 \times 10^4$ cells were plated on stroma in 0.05-5 ng/ml of IL-7 for 1-3 days. The non-adherent cells were harvested followed by PBS wash. The adherent cells were detached with limited trypsinization treatment. Cells from each fraction were counted under a bright-field microscope and ratios were calculated. For re-adhesion assay, equal number of adherent WT and IkE5$^{\Delta/\Delta}$ cells were allowed to re-attach onto stroma and at 3 hours cells were enumerated as described above.

Limiting Dilution Analysis. Adherent WT and IkE5$^{\Delta/\Delta}$ adherent large pre-B cells were sorted on stroma in a 96 well plate in step-wise three-fold serial limiting dilution (10 replicates per dilution) from 300 to 1 cells with 0-5 ng/ml of IL-7. Colonies were scored visually after 6 days. The mean frequency of colony forming cells was calculated by L-Calc software (Stem Cell Technologies) based on Poisson distribution of the probability of wells scoring positive.

Intracellular Calcium and Flux Measurements. For measurement of intracellular calcium, non-adherent and adherent WT and IkE5$^{\Delta/\Delta}$ pre-B cells were stained with Fura-red (Life technologies) as per manufacturer's protocol. For calcium flux, cells were harvested into staining buffer that contained 25 mM Hepes (pH 7.2), 125 mM NaCl, 5 mM KCl, 1 mM Na$_2$HPO4, 0.1% glucose and 0.5 mM MgCl$_2$, 1 mM CaCl$_2$ and 0.1 g BSA just prior to use. Calcium green (Life technologies) and Fura-red were added for 30 minutes at 37° C. Cells were washed twice and re-suspended in staining buffer and placed on ice. Just prior to analysis on FACSCanto™ (BD), the cells were equilibrated to 37° C. Data was acquired for 30 seconds and then pulsed with anti-IgM antibody or ionomycin and acquired for additional indicated time points. Data was analyzed using kinetics platform on FlowJo software (Tree Star).

Apoptosis Assay. Cells were stained for apoptosis using Annexin V: Apoptosis detection kit I (BD) according to manufacturer's protocol.

Cell Cycle Analysis. Cells were harvested at the indicated time points and fixed in 70% cold ethanol overnight at 4° C. Fixed cells were stained with propidium iodide (PI) staining buffer (250 μg/ml RNaseA, 50 μg/ml PI) for 30 min at 37° C. and the DNA content was detected by FACS canto. The resulting files were analyzed with FlowJo (Tree Star).

BrdU Pulse-Chase Assay. Cells were labeled for 45 min with BrdU washed and then incubated in growth media for up to 48 hrs. Cells were harvested at the indicated time points for proliferation analysis using the BrdU flow Kit (BD) per the manufacturer's protocol.

Phase Contrast Microscopy. Phase-contrast pictures of large-preB cells were taken with a Zeiss Axiovert 200M microscope. Prior to microscopy, cells were cultured on OP9-GFP for 24 hours in 5 ng/ml of IL-7.

Immuno-Blotting. Cells were harvested and whole cell extracts were prepared using RIPA buffer containing 10 mM Tris-HCl (pH 8.0), 1 mM EDTA, 1% Triton X-100, 0.1% sodium deoxycholate, 0.1% SDS and 140 mM NaCl. Protease and phosphatase inhibitors (Roche) were added to extraction buffer just prior to use. Equal amounts of protein lysates were separated by SDS-PAGE and transferred to PVDF membranes (Millipore) and probed with indicated antibodies as per manufacturer's protocol.

Immunofluorescence. Cells grown on stroma on Lab-Tek® Chamber Slide (Electron Microscopy Sciences) were fixed with 3% paraformaldehyde for 20 min at room temperature and then permeabilized with phosphate-buffered saline (PBS) plus 0.1% Tween-20 for 45 min. After blocking with PBS containing 2% bovine serum albumin (BSA) for 10 min, the cells were stained with anti-phospho FAK antibody for 45 min, followed by TRITC-conjugated secondary antibody for 30 min. The slides were treated with Vectashield containing DAPI (Vector Laboratories) and mounted. Images were collected using Nikon A1SiR Confocal Microscope and processed using NIS element confocal imaging software.

Adhesion to Integrin Ligands and In Vitro FAK Inhibition Assay. Adhesion assay were performed in non-TC treated plates (BD). The plates were coated with 10 ug/ml fibronectin (FN), collagen (Col.) (Invitrogen) or BSA alone overnight at 4° C. After blocking the plates with 2% BSA for 1 h, equal number of cells were plated and incubated for the indicated time points. At the end of the assay, unbound and bound cells were harvested and enumerated. Percent adhesion was calculated by taking ratio of bound cells over total cells used in each assay.

For inhibition assay, 1 μm FAK inhibitor (PF-431396 or PF-562271, Sigma) or DMSO control was used for treatment and cells were harvested as bound and unbound fractions at 4 or 24 hour post-treatment for calculation of percent adhesion and inhibition of adhesion, apoptosis and cell cycle assays. For peptide mediated blocking of adhesion[55], equal number of cells were pretreated for 45 minutes with either 400 μg/ml G-R-G-D-S-P (SEQ ID NO:1) or the control peptide G-R-G-E-S (SEQ ID NO:2) (American Peptide Company) and plated on FN-coated TC dishes. Cells were enumerated for calculation of percent adhesion and percent inhibition.

The effect of growth factors and adhesion was evaluated by plating $2 \times 10^5$ adherent pre-B cells on FN and Col. or BSA coated plates in the presence of 5 ng/ml IL-7, 100 ng/ml SCF, both (IL-7+SCF) or no cytokines for 24 hours. At 24 hours, cells were counted and analyzed for cell cycle and apoptosis. For integrin and growth factor signaling assay, equal number ($2 \times 10^5$) cells were plated in FN and Col. or BSA coated plates in presence of 5 ng/ml IL-7, 100 ng/ml SCF, both (IL-7+SCF) or no cytokines for 24 hours. At 24 hours, cells were harvested and counted. Mutant cells were analyzed for cell cycle and apoptosis.

In Vivo FAK Inhibition Assay. WT and IkE5$^{fl/fl}$ CD19cre mice were used for treatment with FAK inhibitor PF-562271 or vehicle (50% DMSO/50% PEG-400). Both cohorts were given a dosage of 25 mg/kg/mouse of inhibitor or equal volume of vehicle by oral gavage. Dosage regimens of either 3 or 5 doses were given at ~12 hours apart. At 3 hours after the final dose, mice were sacrificed by CO2 asphyxiation. Bones were flushed and cells were collected and total bone marrow cellularities were estimated. Cells were stained for pre-B cell cell surface markers and PI/Annexin V staining was performed to estimate apoptotic cell frequency.

Transwell Migration Assay. Transwell plates with (Corning, 3422) were coated with fibronectin (10 μg/ml). The wells were washed and blocked with BSA. Serum-free medium with 1% BSA containing the CXCL12/SDF-1α, (100 ng/ml) was added to the bottom well of the transwell plate. Equal number of cells in 100 μl of serum-free media were added to the upper chambers and incubated for 2 hours at 37° C. At the end of the time point, inserts were removed and migrated cells in bottom wells were counted. Percent migration was calculated by taking ratios of migrated cells over total cells plated in inserts.

RNA-Seq, Gene Expression and Pathway Analysis. RNA isolated with Trizol was purified using the PureLink RNA mini kit (Ambion). The Truseq RNA sample prep kit was used for construction of cDNA libraries for RNA-sequencing (Illumina). The cDNA libraries were ligated with indexed primers and amplified by 15 cycles of PCR. The amplified libraries were multiplexed and sequenced by the Genome Analyzer at Systems Biology Lab, Harvard University. Read alignment on mouse mm9 assembly was conducted by the BWA algorithm implemented by the DNA Nexus suite. The Deseq algorithm implemented by the R platform was used to determine differential gene expression in freshly sorted WT and IkE5$^{\Delta/\Delta}$ large pre-B, WT small pre-B as well as in adherent and non-adherent fractions of sorted large pre-B cells after limited propagation on OP9 stroma. Pathway analysis of upregulated genes in IkE5$^{\Delta/\Delta}$ relative to WT large pre-B was conducted using the Ingenuity software. Heatmaps of normalized tags for gene subsets across WT and IkE5$^{\Delta/\Delta}$ pre-B cell populations were generated with the Avadis software.

Adoptive Transfer of Purified Pre-B Cell Populations to NSG Mice. NOD/SCID/Il2rg$^{-/-}$ (NSG) mice (Jackson Laboratory) were conditioned by 300 cGy gamma irradiation and injected via lateral tail vein with $3 \times 10^6$ sorted large pre-B (CD19$^+$CD43 BP1$^+$) cells. Diseased mice were characterized by histopathological analysis as previously described[56]

Example 1

The Ikaros Family is Required for Pre-B Cell Differentiation

To determine the role of the Ikaros family during B cell differentiation, exon 5 of the Ikzf1 gene (defined hereafter as IkE5), encoding two Ikaros DNA binding zinc fingers, was floxed (IkE5$^{fl/fl}$; FIG. 1a) and deleted from either the common lymphoid progenitor or the downstream definitive pro-B cell precursor using CD2-Cre or CD19-Cre transgenes, respectively (FIG. 9a). Deletion of IkE5 generates Ikaros protein isoforms that lack DNA binding activity and are structurally similar to those encountered in human B-ALL (Ik6)[24] (FIG. 1b, pre-B IkE5$^{\Delta/\Delta}$). These mutant Ikaros isoforms act in a dominant-negative fashion by dimerizing with co-expressed family members, including Aiolos, and interfering with their DNA binding activity[30,32]. The dominant-negative phenotype was confirmed by combining the Ikzf3 (Aiolos gene) homozygous null and the Ikzf1 heterozygous null mutations (Ikzf3$^{-/-}$ Ikzf1$^{+/-}$). Deletion of IkE5 or the combined Ikzf3$^{-/-}$ Ikzf1$^{+/-}$ mutations caused a similar block and expansion of large pre-B cells (CD19$^+$CD43$^+$BP1$^+$; FIG. 1c, d and FIG. 9b, c). These normally represent a minor population but were now found in numbers that were similar to those of all bone marrow (BM) B cells in wild type (WT) mice (FIG. 1d). As in WT, the majority of mutant large pre-B cells were in cell cycle (FIG. 1e). The few immature B (CD19$^+$IgM$^+$) cells detected in the IkE5$^{fl/fl}$ CD2-Cre mice (FIG. 1d) had not deleted IkE5$^{fl/fl}$ (FIG. 9d), indicating that transition from the large to the small pre-B cell is absolutely dependent on the DNA binding activities of Ikaros gene family members expressed at this stage of differentiation.

A hallmark of B cell differentiation is the successful recombination of the Igh locus, a prerequisite for transition to the pre-B cell stage. Both D-J and V-DJ proximal and distal recombination events at the Igh locus were detected at similar frequencies in WT and IkE5$^{\Delta/\Delta}$ pre-B cells (FIG. 1f and data not shown). However, the low-level Igk rearrangements detected in WT were not seen in mutant pre-B cells (FIG. 1f), indicating either inability to undergo light chain recombination or a block in differentiation prior to Igk recombination. Consistent with recombination only at the Igh locus, the majority of mutant pre-B cells expressed intracellular IgM but not Igκ (FIG. 10).

Since Igk recombination is required for B cell maturation, an attempt to rescue the pre-B cell arrest was made by crossing the IkE5$^{\Delta/\Delta}$ mice to the D23 transgenic line that expresses a pre-rearranged Igκ chain[33]. IkE5$^{\Delta/\Delta}$ D23 pre-B cells were unable to differentiate past the large pre-B (CD19$^+$CD43$^+$ BP1$^+$) stage (FIG. 1g and FIG. 10), although both IgM and Igκ chains were expressed intracellularly. This indicates that lack of Igk recombination was not the cause of the maturation defect in Ikaros-deficient pre-B cells. Hence, the transition from large to small pre-B cell is regulated by the Ikaros gene family through a mechanism that is independent of recombination at the IgH or IgL gene loci.

Example 2

Growth of IkE5$^{\Delta/\Delta}$ Pre-B Cells Requires Adhesion to Stroma

Figure 2A:
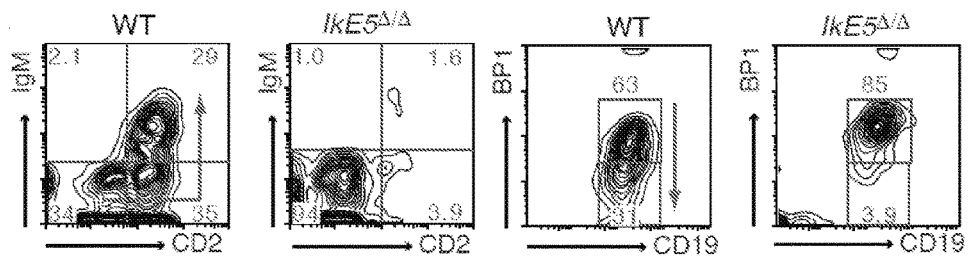
Figure 2B:
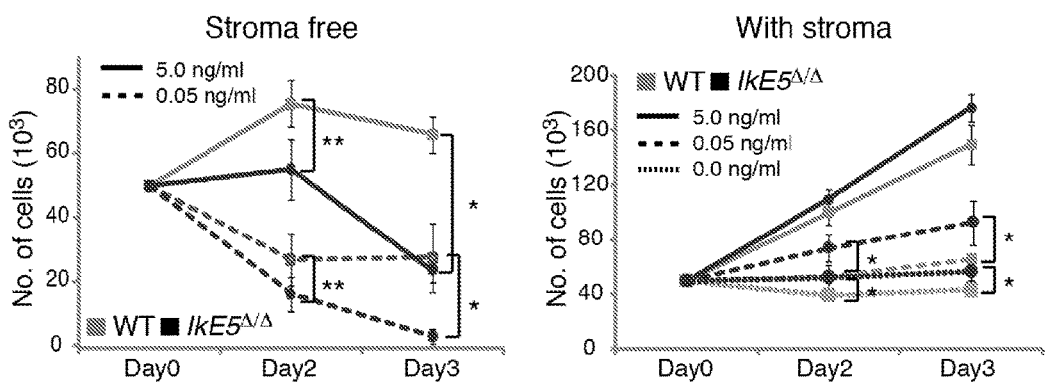
Figure 2C:
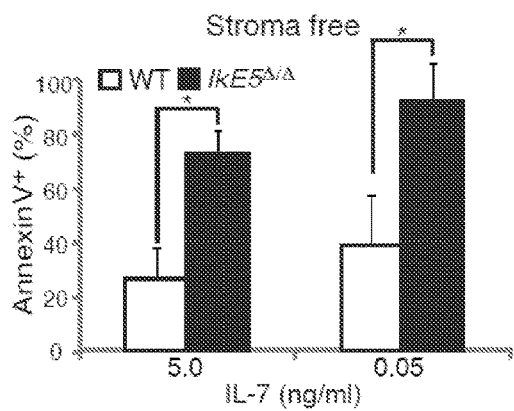

The developmental defect in IkE5$^{\Delta/\Delta}$ large pre-B cells was further evaluated in in vitro cultures[11,34]. Under differentiation-inducing conditions (i.e. seven days of stromal-free culture in low concentrations of serum and IL-7), the majority of WT large pre-B cells exited the cell cycle and differentiated into small pre-B (CD19$^+$CD2$^+$IgM$^-$) and immature B (CD19$^+$IgM$^+$CD2$^+$) cells, whereas mutant large pre-B cells (CD19$^+$CD43$^+$BP1$^+$) remained undifferentiated (FIG. 2a). An increase in the concentration of IL-7 promoted the proliferative expansion of WT large pre-B cells but had little effect on their mutant counterparts. In the absence of stroma, survival of IkE5$^{\Delta/\Delta}$ pre-B cells was greatly compromised compared to WT pre-B cells even in the presence of high concentrations of IL-7, with high levels of apoptosis detected from early time points of culture (FIG. 2b, left panel, and FIG. 2c).

Figure 2D:
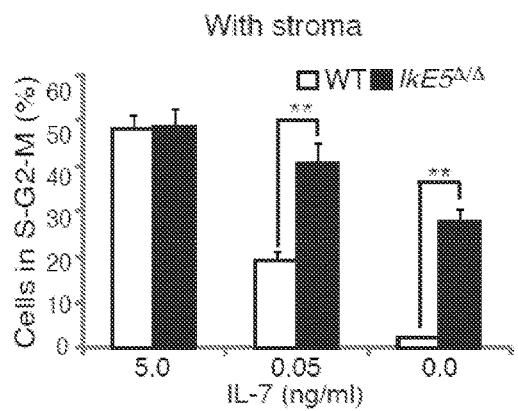
Figure 2E:
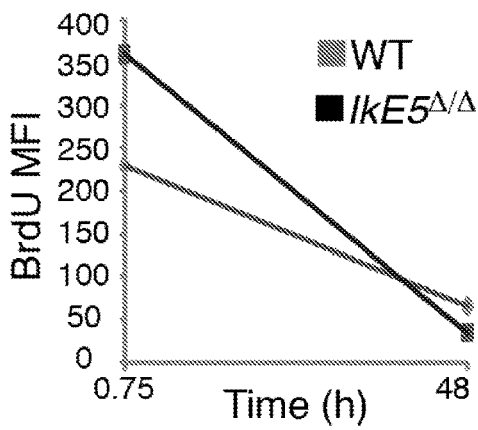

Although pre-B cell precursors can proliferate and differentiate in the absence of stromal contact, they can only self-renew and undergo greater expansion on stroma[34-36]. Since IkE5$^{\Delta/\Delta}$ large pre-B cells proliferated and expanded in vivo in the BM, whether they could grow in vitro on OP9 BM-derived stroma was tested. Under these conditions, IkE5$^{\Delta/\Delta}$ large pre-B cells grew better than WT especially under limiting concentrations of IL-7 (FIG. 2b, right panel), with ~2 to 10-fold more cells in cycle (FIG. 2d). IkE5$^{\Delta/\Delta}$ pre-B cells also displayed an increase in cell cycle kinetics compared to WT. Labeling with BrdU showed increased incorporation by IkE5$^{\Delta/\Delta}$ pre-B cells during pulse and a faster decline during chase (FIG. 2e), indicating shorter cell cycle transitions compared to WT pre-B cells. IkE5$^{\Delta/\Delta}$ pre-B cells are therefore dependent on stroma for survival and growth, with enhanced proliferation and more rapid cell cycling relative to WT pre-B cells.

Example 3

Loss of Ikaros Arrests Pre-B Cells in a Self-Renewing Adherent Phase

A striking morphological difference was apparent between IkE5$^{\Delta/\Delta}$ and WT large pre-B cell OP9 stromal cultures. The majority of WT pre-B cells were round, light-refracting cells loosely attached to stroma, but the majority of mutant cells had a dark, flat morphology and appeared incorporated into the stromal layer (FIG. 3a, b). Dark, stromal-adherent pre-B cells were also present in WT cultures, but at a much lower frequency (FIG. 3a, b). The few IkE5$^{\Delta/\Delta}$ non-adherent cells displayed increased apoptosis (FIG. 11a), indicating that in the absence of stromal contact, their survival was greatly compromised.

Figure 3D:
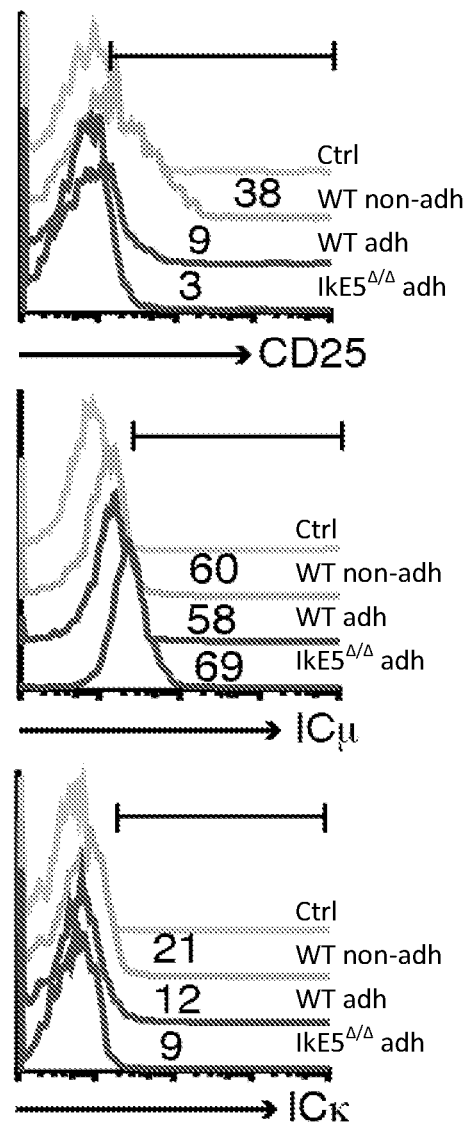

A progenitor-progeny relationship between adherent and non-adherent pre-B cells was next established in WT cultures. Comparison of transcriptional profiles revealed that small pre-B cell markers (e.g. Igκ, Rag1, Rag2, Irf4, Cd2, and Cd25) expressed at low levels in adherent pre-B cells were induced in the non-adherent fraction, whereas cell cycle-promoting genes, such as Ccnd2, Egr1, Pcna, Igfbp4 and Myc, displayed the opposite expression pattern (FIG. 3c). The overall gene expression of mutant adherent pre-B cells was similar to that of their WT adherent counterparts, although a further reduction in small pre-B cell markers was seen in the mutant cells. The differential expression of small pre-B cell markers, such as CD25 and intracellular Igκ, between WT adherent and non-adherent pre-B cells, was also detected by flow cytometry. Intracellular IgM, a pan pre-B cell marker, was similarly expressed in both WT pre-B cell subsets (FIG. 3d). In the mutant cultures, adherent pre-B cells expressed IgM but no Igκ or CD25, protein consistent with the ex vivo analysis of IkE5$^{\Delta/\Delta}$ pre-B cells (FIG. 1f, g).

Figure 3E:
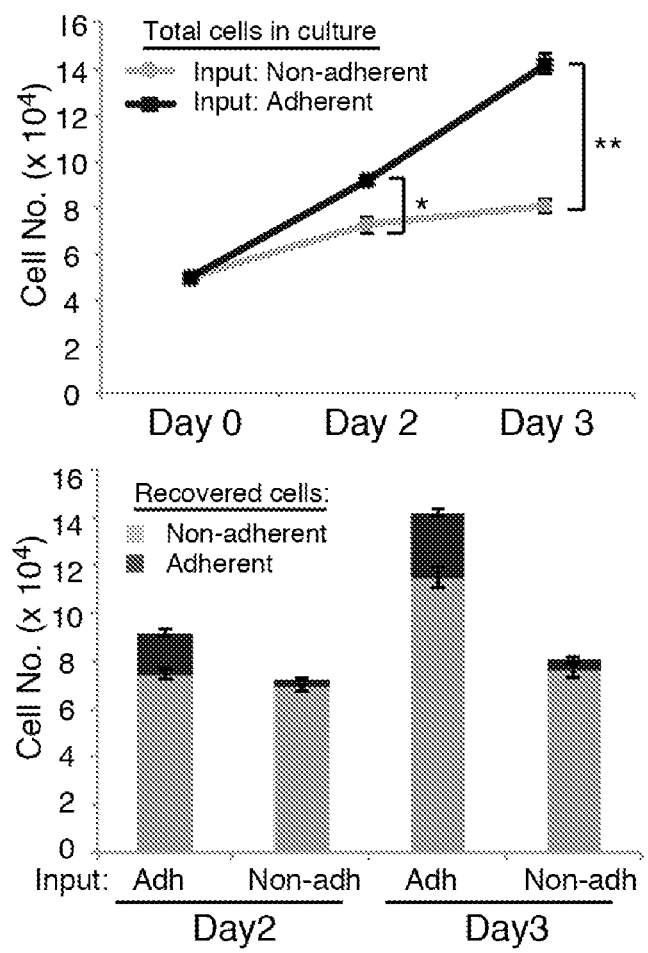

The cell cycle properties of WT adherent and non-adherent pre-B cells were evaluated. Whereas most WT adherent pre-B cells were in cycle, non-adherent WT pre-B cells consisted of large cycling and smaller non-cycling cells at a ratio that decreased with time in culture (FIG. 11b and data not shown). WT adherent pre-B cells could be serially passaged on stroma and gave rise to both adherent and non-adherent cells, whereas WT non-adherent pre-B cells gave rise to mostly non-adherent cells with limited proliferative expansion (FIG. 3e).

Figure 3F:
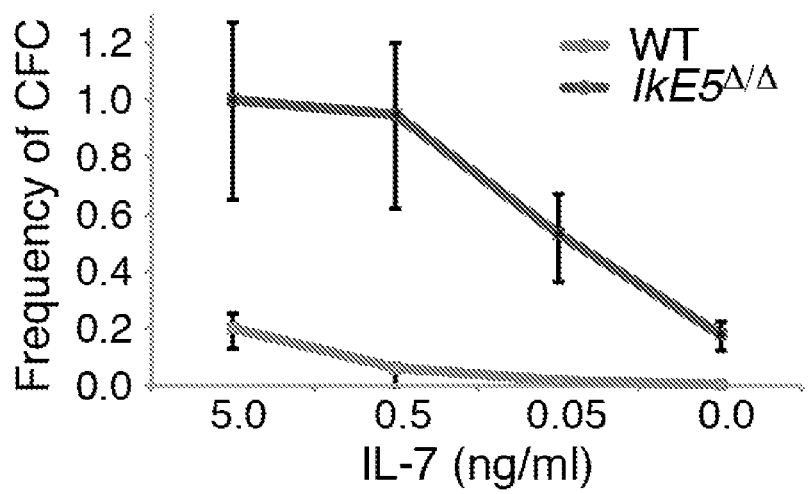
Figure 3G:
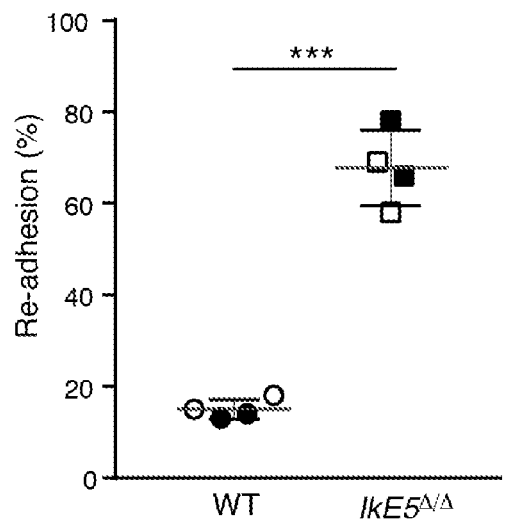

Given the self-renewing potential of adherent pre-B cells, the clonogenic properties of WT and mutant adherent pre-B cells were compared in a limiting dilution colony-forming assay on stroma (FIG. 3f). Even in the absence of IL-7, the colony-forming potential of IkE5$^{\Delta/\Delta}$ pre-B cells was high (~20%) and orders of magnitude greater than WT. Although addition of IL-7 had little effect on the ability of IkE5$^{\Delta/\Delta}$ adherent pre-B cells to form colonies on stroma, it did increase their size by increasing proliferation (FIG. 2d and data not shown). Evaluation of the ability of WT and IkE5$^{\Delta/\Delta}$ adherent pre-B cells to re-associate with stroma revealed another important difference. Within 3 hrs of replating, 68% of IkE5$^{\Delta/\Delta}$ pre-B cells rapidly re-bound to stroma, whereas only 15% of WT adherent cells did so even after overnight incubation (FIG. 3g).

Together, these studies provide insight into pre-B cell differentiation by describing the transition from a stromal-adherent to a non-adherent phase. Stromal-adherent pre-B cells express pre-BCR are highly proliferative and have limited self-renewing potential. They are highly dependent on Ikaros for transition to a non-adherent phase where they exit the cell cycle, lose self-renewal capacity, and acquire expression of genes supporting B cell maturation. Loss of Ikaros augments stromal adhesion, self-renewal, and proliferation, pathways that most likely antagonize activation of the pre-B cell differentiation program.

Example 4

Ikaros Loss Augments Stromal-Dependent Proliferative Signaling

The survival and proliferative expansion of pre-B cells are supported by a combination of pre-BCR and IL-7R signaling that activates the PI3K-Akt and Erk1-2 MAPK pathways (FIG. 12a and FIG. 4a, b). Both PI3K-Akt and Erk1-2 were active in WT adherent but not in non-adherent pre-B cells (FIG. 4a), which are in the process of exiting the cell cycle (FIG. 11b) and upregulating expression of small pre-B cell markers (FIG. 3c, d). Activation of Akt was similar in IkE5$^{\Delta/\Delta}$ adherent pre-B cells compared to WT, but activation of Erk1 and Erk2 was greatly increased (FIG. 4a). Consistent with a higher Erk1-2 MAPK activity, an increase in Cyclin D2 (FIG. 4a) and cell cycle (FIG. 2d, e) was observed in IkE5$^{\Delta/\Delta}$ compared to WT large pre-B cells.

Figure 4C:
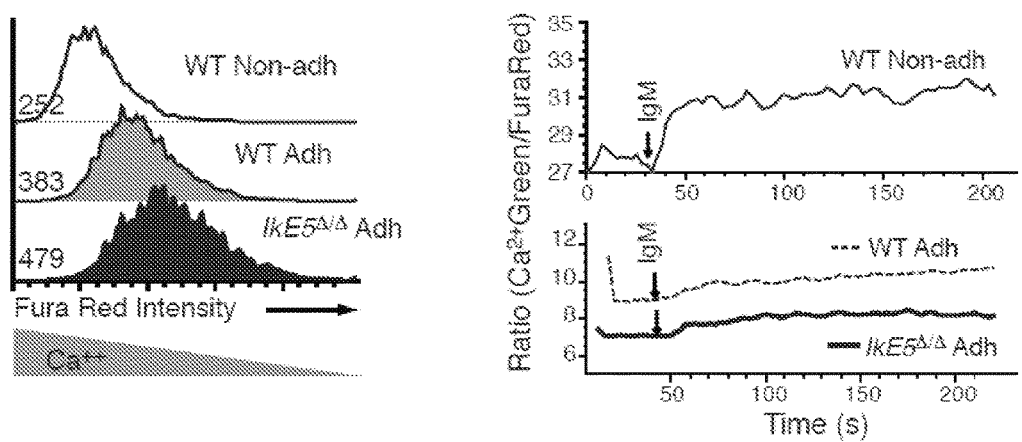

Pre-BCR signaling also supports differentiation to the small pre-B cell stage by activating PLCγ and Ca$^{2+}$ signaling (FIG. 12a). These signaling events are required to switch cells from a proliferative to a quiescent state by inducing transcriptional responses that rely in part on the transcription factor Foxo1 (refs. 18,20). Notably, the baseline level of intracellular Ca$^{2+}$ was low in both WT and IkE5$^{\Delta/\Delta}$ adherent pre-B cells but elevated in WT non-adherent pre-B cells, which were the only cells capable of fluxing Ca$^{2+}$ either upon pre-BCR engagement or ionomycin treatment (FIG. 4c and FIG. 12b). Upstream and downstream effectors of Ca$^{2+}$ signaling such as Blnk and Foxo1 proteins were expressed at low levels in both WT and IkE5$^{\Delta/\Delta}$ adherent pre-B cells and were greatly induced in WT non-adherent cells, consistent with small pre-B cell differentiation (FIG. 4b). The low amounts of Foxo1 expressed in adherent pre-B cells were phosphorylated, correlating with active PI3K-Akt in these cells. As previously reported for small pre-B cell differentiation[20], p38 MAPK activity was induced from WT adherent to non-adherent pre-B cells but was nearly undetectable in IkE5$^{\Delta/\Delta}$ adherent pre-B cells (FIG. 4b).

Both the proliferation- and differentiation-inducing arms of pre-BCR signaling are dependent on activation of Fyn, Lyn, Blk and Syk. These PTKs were expressed at similar protein amounts in WT adherent and non-adherent pre-B cells (FIG. 4a). In IkE5$^{\Delta/\Delta}$ compared to WT adherent pre-B cells, the protein amounts of these key proximal components of pre-BCR signaling (Fyn, Syk, Blk) were greatly reduced, while the amounts of activated (phosphorylated) Lyn were also diminished (FIG. 4b and FIG. 12c). The reduced protein expression or activation of these PTKs was unexpected, as it predicts not only a defect in differentiation but also in proliferation of IkE5$^{\Delta/\Delta}$ pre-B cells, contrary to what was observed both in vivo and in vitro (FIGS. 1-2).

IL-7R signaling was examined as a possible mechanism of compensation for the loss in pre-BCR signaling. Phosphorylation of Stat5 (p-Stat5), a measure of IL-7R signaling, was comparable in WT and IkE5$^{\Delta/\Delta}$ adherent pre-B cells (FIG. 4a). Furthermore and in contrast to WT pre-B cells, IL-7R signaling was unable to support the growth of mutant pre-B cells under stromal-free conditions, and the mutant pre-B cells were only partly dependent on IL-7 for growth on stroma (FIG. 2b and FIG. 3f). Thus, receptors other than IL-7R and pre-BCR must be responsible for activation of survival and proliferation signaling pathways in IkE5$^{\Delta/\Delta}$ large pre-B cells. Engagement of such receptors is likely to be mediated by interaction of the mutant pre-B cells with stroma.

Example 5

Increased Integrin Signaling in IkE5$^{\Delta/\Delta}$ Pre-B Cells

Figure 5B:
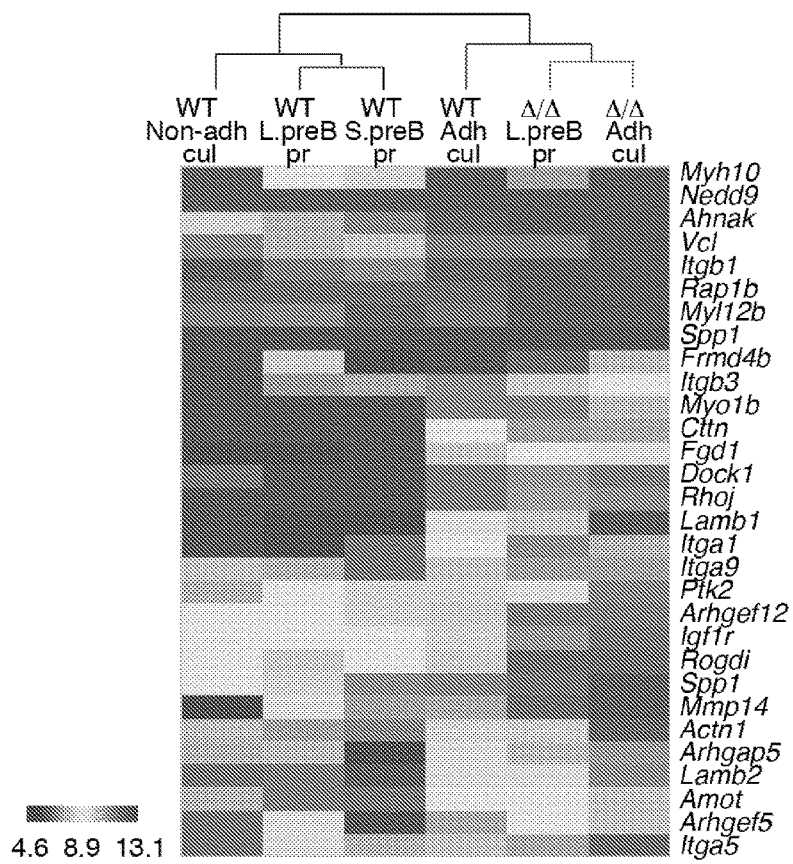
Figure 5C:
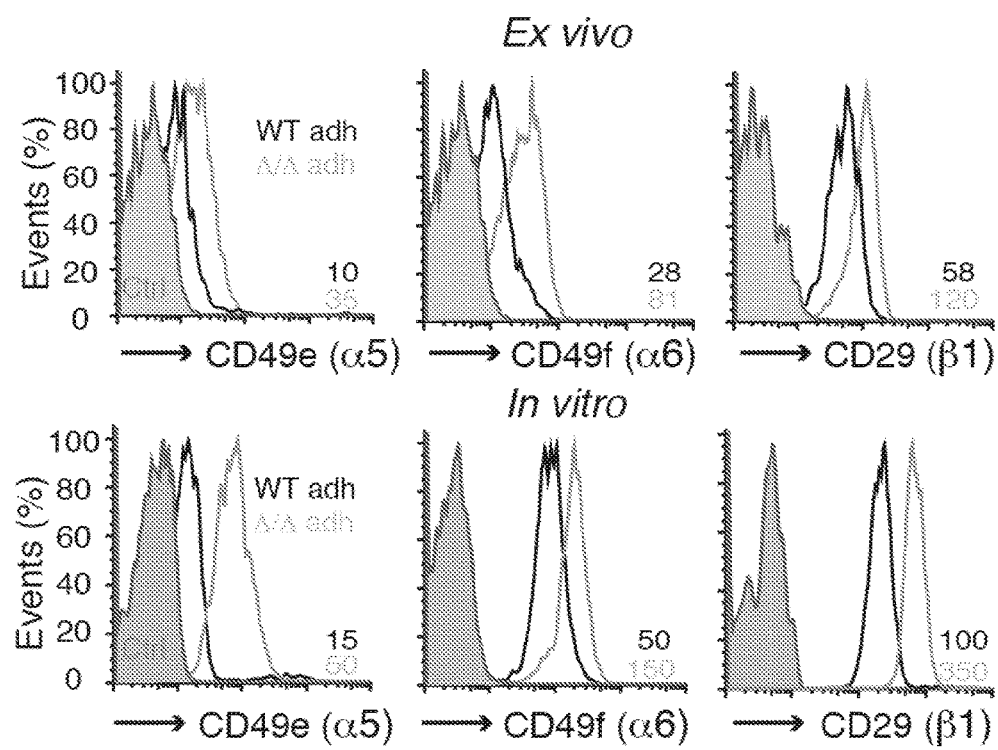
Figure 5D:
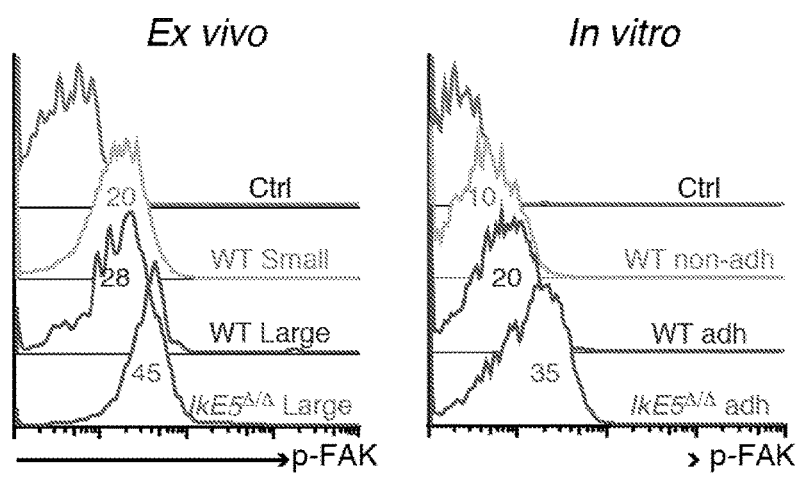
Figure 5E:
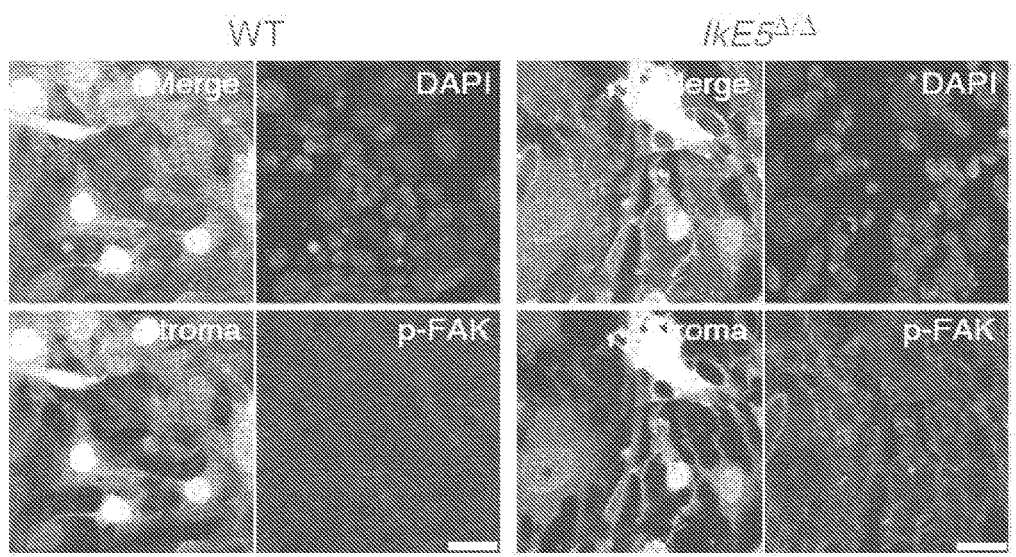
Figure 5F:
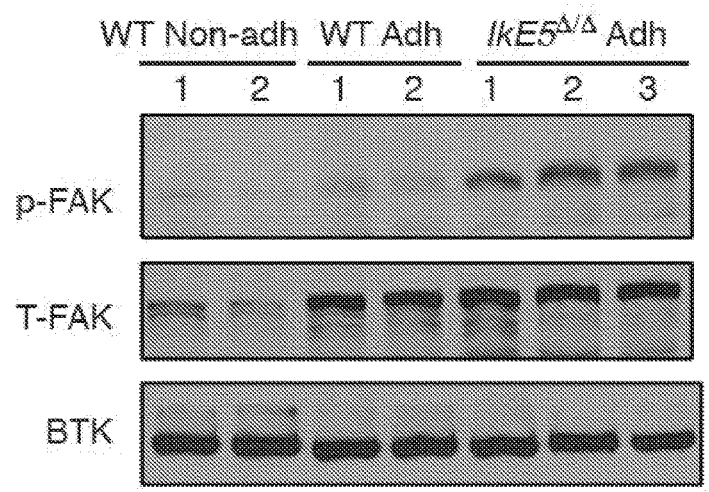

A comparative genome-wide transcriptional analysis of primary and cultured WT and IkE5$^{\Delta/\Delta}$ pre-B cells was performed to reveal potential pathways that might support the aberrant adhesion and growth properties of the mutant population. A signature of genes was deduced that was differentially expressed between both freshly isolated IkE5$^{\Delta/\Delta}$ and WT large pre-B cells and between IkE5$^{\Delta/\Delta}$ and WT adherent pre-B cells cultured in vitro (FIG. 5a, b). Up-regulated genes in IkE5$^{\Delta/\Delta}$ pre-B cells were highly enriched in pathways involved in focal adhesion and remodeling of the actin cytoskeleton (FIG. 5a). Integrins (e.g. Itga1, Itga5, Itgb1) as well as other structural and signaling components of focal adhesions (e.g. Ptk2, Vcl, Actn1, Cttn, Dock1, Rogdi) were shared by many of these pathways (FIG. 5b). The increase in integrin expression was validated at the protein level in both primary and cultured cells. Furthermore, expression of the active isoform of integrin β1 (detected with an activation-specific anti-integrin β1 antibody and elevated levels of phosphorylated focal adhesion kinase (p-FAK), a key downstream effector of integrin signaling, indicated that not only expression but also activation of integrin signaling were elevated in IkE5$^{\Delta/\Delta}$ pre-B cells (FIG. 5c-f). Although not as pronounced as in IkE5$^{\Delta/\Delta}$ pre-B cells, significantly higher amounts of FAK and p-FAK were also observed in WT adherent relative to non-adherent pre-B cells, indicating that integrin signaling is also active in WT adherent pre-B cells (FIG. 5d-f).

Figure 5G:
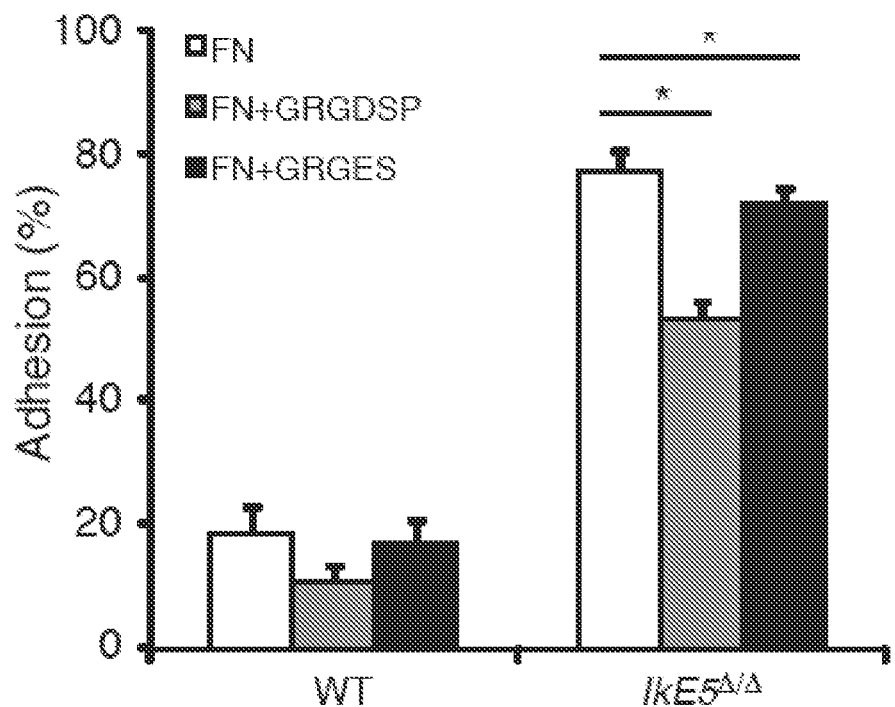
Figure 5H:
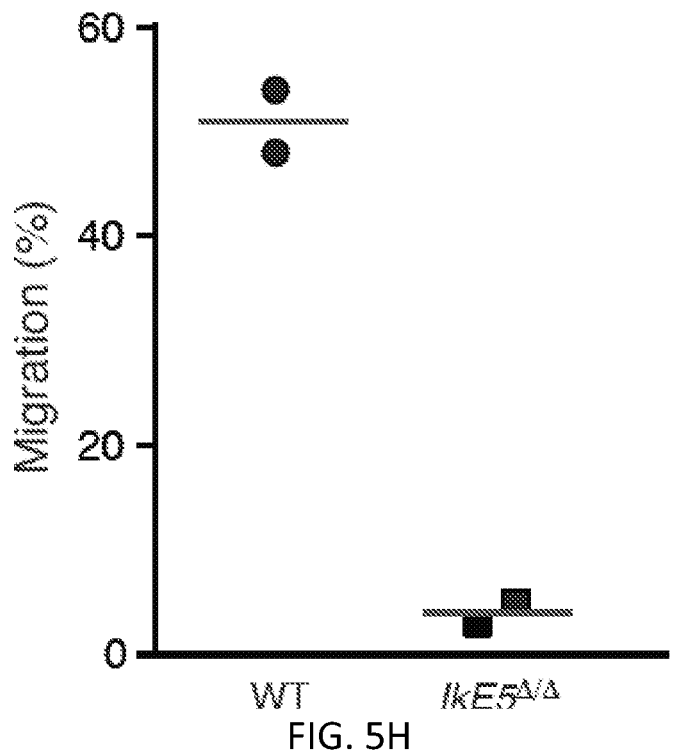

Further evidence for integrin-mediated adhesion was provided by measuring binding of adherent pre-B cells to integrin ligands in vitro. Notably, the frequency by which IkE5$^{\Delta/\Delta}$ (~80%) or WT (~20%) pre-B cells bound to fibronectin (FIG. 5g) was similar to that with which they bound to stroma (FIG. 3g). A fibronectin peptide (RGD) that binds to integrin α4β1 significantly inhibited the binding of both WT and IkE5$^{\Delta/\Delta}$ pre-B cells, implicating VLA-4 as one of the integrins participating in pre-B cell adhesion (FIG. 5g).

Integrin signaling is involved in pre-B cell chemotaxis in response to CXCL12 (stromal cell-derived factor 1; SDF1)-CXCR4 receptor interactions[37]. Whether elevated integrin signaling in IkE5$^{\Delta/\Delta}$ pre-B cells affected their chemotactic properties. In sharp contrast to wild-type adherent pre-B cells, their mutant counterparts were unable to migrate in a transwell assay in response to SDF1 (FIG. 5h), indicating that increased integrin signaling reduced chemokine-mediated chemotaxis of the mutant pre-B cells. Consistent with these in vitro data, circulating pre-B cells were not detected in IkE5$^{fl/fl}$ CD19-Cre mice although they were readily seen in WT mice (FIG. 13a). Thus, the increase in integrin signaling manifested upon loss of Ikaros in pre-B cells is likely responsible for their stable adhesion to stroma, survival, and proliferative expansion.

Example 6

Survival of IkE5$^{\Delta/\Delta}$ Pre-B Cells is Dependent on FAK Activation

The role of integrin signaling in supporting stromal adhesion and survival of IkE5$^{\Delta/\Delta}$ pre-B cells was validated by treatment with a small molecule inhibitor (PF-431396) that blocks the kinase activity of FAK (Ptk2) and the related kinase Ptk2b (ref. 38), which together serve as major signaling effectors of the integrin pathway. FAK-Ptk2b inhibitor treatment greatly reduced stromal adhesion not only in IkE5$^{\Delta/\Delta}$ but also in WT pre-B cells (FIG. 6a). However, the loss in adhesion preceded an increase in apoptosis only in IkE5$^{\Delta/\Delta}$ pre-B cell and not in WT pre-B cells (FIG. 6b).

The dependence of IkE5$^{\Delta/\Delta}$ pre-B cells on integrin signaling was also tested in vivo. IkE5$^{fl/fl}$ CD19-Cre mice and WT littermates were given 3-5 doses of an orally bioavailable FAK-Ptk2b inhibitor (PF-562271) or vehicle control and the number of BM pre-B/B cells and apoptotic index was quantified shortly afterwards (FIG. 6c, d). IkE5$^{\Delta/\Delta}$ large pre-B cells constituted the great majority of BM B cells in vehicle-treated IkE5$^{fl/fl}$ CD19-Cre mice and showed rapid reduction following FAK inhibitor treatment (FIG. 6c). This decrease correlated with an increase in apoptosis that was specific for large pre-B cells and correlated with a specific reduction in activated FAK (p-FAK) in IkE5$^{\Delta/\Delta}$ large pre-B cells (FIG. 6d and FIG. 13b). FAK inhibitor treatment had little effect on the cellularity of WT BM B cells that were mainly comprised of small pre-B and immature B cells. Given the small number of WT large pre-B cells present in the WT BM, it was difficult to discern the effect of the FAK inhibitor treatment on the WT large pre-B cell population.

Taken together, these studies indicate that increased integrin signaling mediated by FAK is responsible for increased stromal adhesion, survival, and accumulation of Ikaros-mutant large pre-B cells under both in vitro and in vivo settings.

Example 7

Integrin and Growth Factor Signaling Cooperate in Pre-B Cells

Whether integrin-mediated adhesion was sufficient to support stromal-dependent survival and proliferation of IkE5$^{\Delta/\Delta}$ pre-B cells was then tested. The majority of IkE5$^{\Delta/\Delta}$ pre-B cells plated on fibronectin and collagen died after overnight incubation, indicating that integrin signaling alone could not support their survival (FIG. 7a). In sharp contrast, the majority of WT pre-B cells survived under these conditions.

Figure 7C:
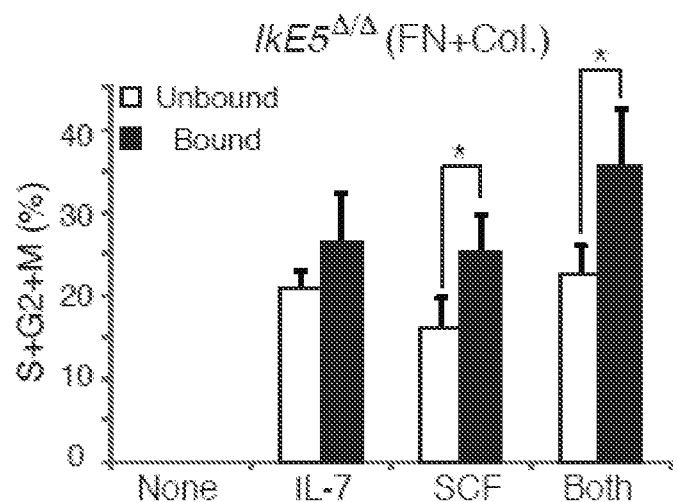

Stromal niches provide adhesion and growth factor support. Growth factors such as the c-Kit ligand (Stem Cell Factor; SCF) and IL-7 are required for the growth of both early hematopoietic progenitors and lymphoid precursors[39,40]. In the absence of integrin ligand binding, IL-7 and/or SCF had little or no effect on the survival of IkE5$^{\Delta/\Delta}$ pre-B cells. However, the combination of integrin engagement and IL-7 or SCF greatly increased IkE5$^{\Delta/\Delta}$ pre-B cell survival (FIG. 7a, b), and had a smaller but still significant stimulatory effect on the proliferation of IkE5$^{\Delta/\Delta}$ pre-B cells (FIG. 7c). Thus, augmentation of integrin signaling in IkE5$^{\Delta/\Delta}$ compared to WT pre-B cells is not only important for maintaining cells in proximity to a stromal niche, but also for cooperating with growth factor signaling to support survival and proliferation, acting in lieu of pre-BCR signaling (FIG. 14).

Example 8

High Leukemogenic Potential of IkE5$^{\Delta/\Delta}$ Pre-B Cells

Figure 8A:
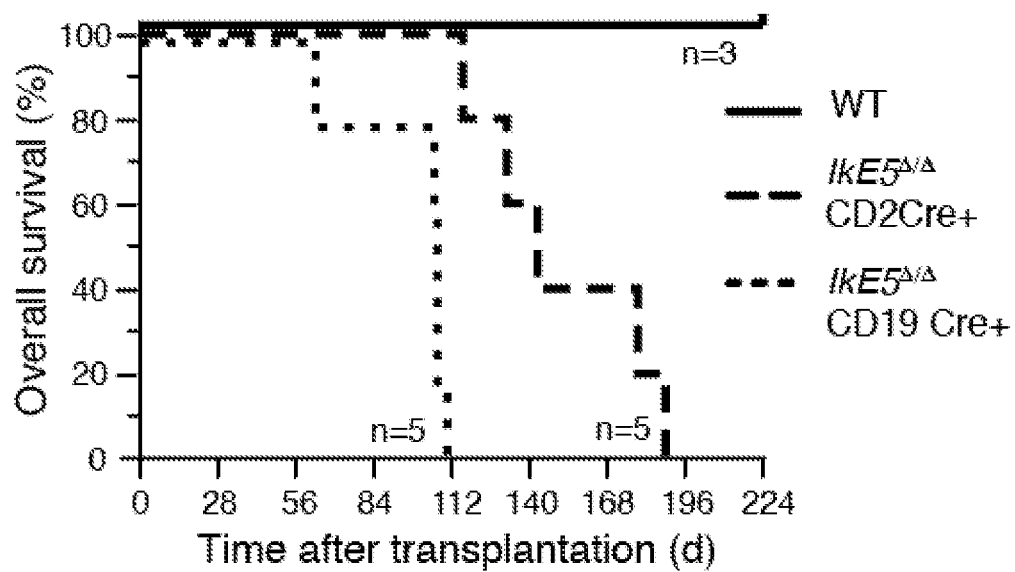

The rapid development of precursor T-lymphoid neoplasms in IkE5$^{\Delta/\Delta}$ mice (data not shown and ref. 41)

precludes the assessment of B-lymphoid leukemogenesis in these mutant mice. The leukemogenic potential of IkE5$^{\Delta/\Delta}$ pre-B cells was therefore evaluated by transplantation of this population into immunodeficient NOD/SCID/Il2rg$^{-/-}$ (NSG) recipient mice. Following transplantation with IkE5$^{\Delta/\Delta}$ pre-B cells isolated from either Cd19-Cre or Cd2-Cre donors, recipient NSG mice uniformly exhibited circulating immature CD19$^+$BP1$^+$CD2$^-$ B-lymphoid cells within 7 weeks (data not shown), and developed signs of disseminated leukemia/lymphoma by 3-4 months post-transplant, with weight loss, hyperventilation, and hepatosplenomegaly (mean spleen weight 668±188 mg), whereas recipients of WT pre-B cells remained healthy (FIG. 8a). The disease in recipients of IkE5$^{\Delta/\Delta}$ Cd19-Cre pre-B cells was somewhat more aggressive than in IkE5$^{\Delta/\Delta}$ Cd2-Cre recipients (FIG. 8a; median survival 107 d vs. 143 d; P=0.0021, Mantel-Cox test). At necropsy, recipients of IkE5/a Cd19-Cre pre-B cells had pancytopenia with severe anemia (blood hemoglobin 4.8±0.7 g/dL) that likely contributed to morbidity or death, while IkE5$^{\Delta/\Delta}$ Cd2-Cre recipients tended to develop hindlimb paralysis and malignant pleural effusions.

Figure 8B:
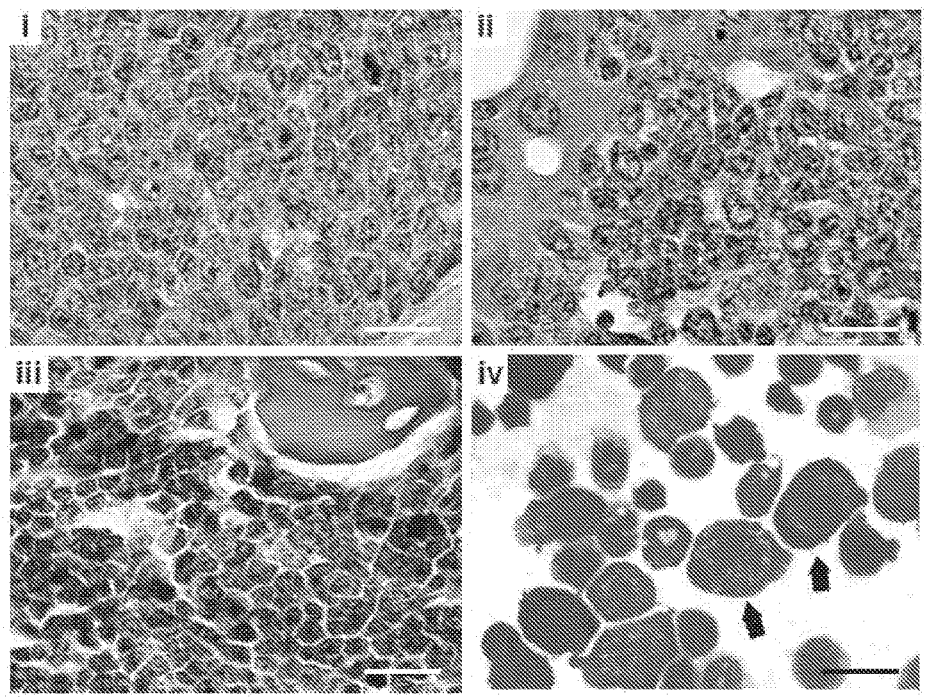

Histopathological analysis showed extensive invasion of spleen and liver and involvement of bone marrow with large lymphoid cells of high mitotic index (FIG. 8b). Phenotypic analysis of the malignant IkE5$^{\Delta/\Delta}$ tumor cells revealed that they were similar to the initially transplanted population with regards to both large pre-B cell surface antigen expression (CD19$^+$CD43$^+$BP1$^+$CD2$^-$; FIG. 15a), expression of adhesion molecules (FIG. 8c), and adherence to stroma (see below). However, in contrast to the polyclonal nature of the transplanted IkE5$^{\Delta/\Delta}$ pre-B cell population (FIG. 1g and FIG. 15b), the IkE5$^{\Delta/\Delta}$ leukemic cells were oligoclonal by Igh gene rearrangement (FIG. 15c, d).

Figure 8C:
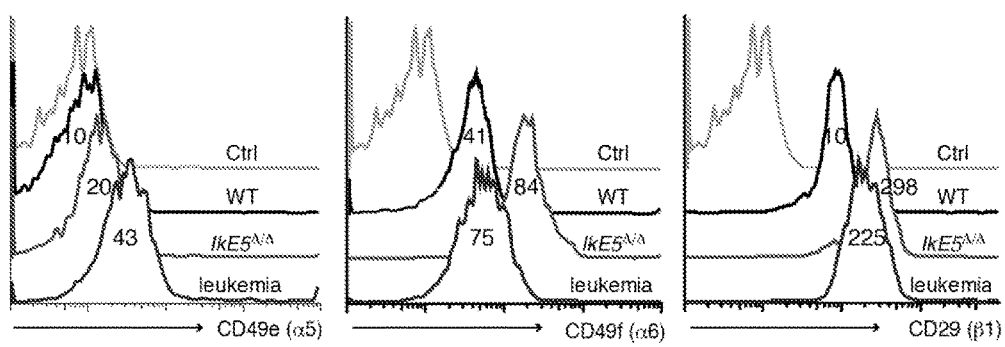
Figure 8D:
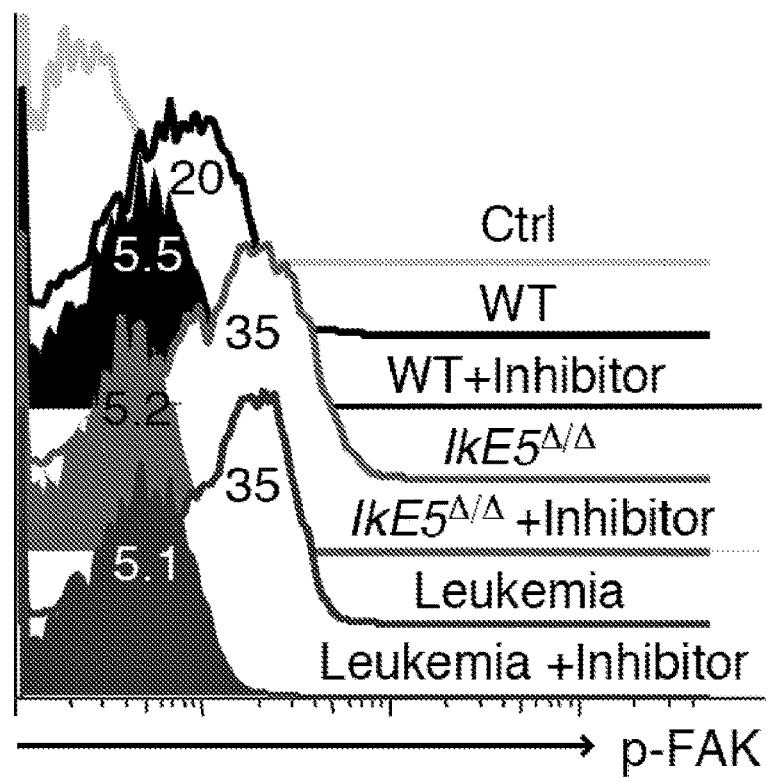
Figure 8E:
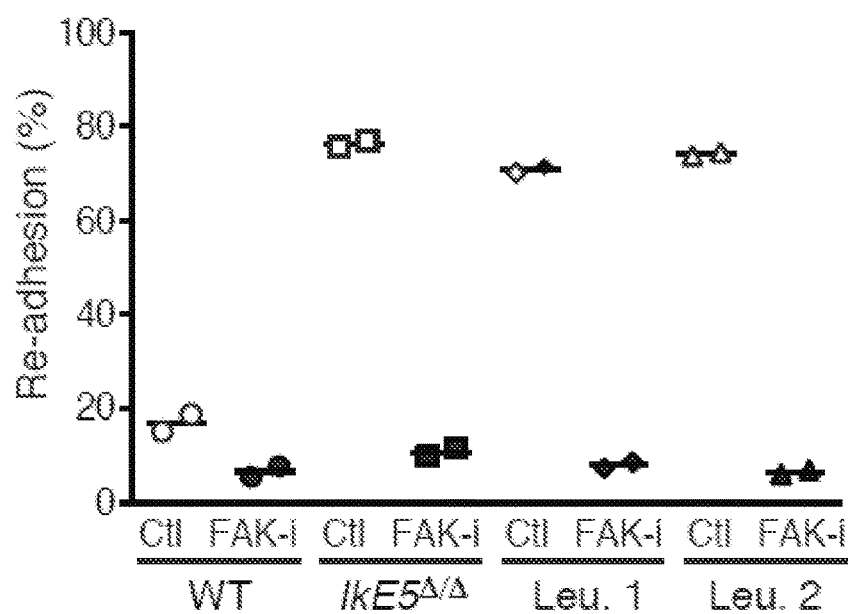
Figure 8F:
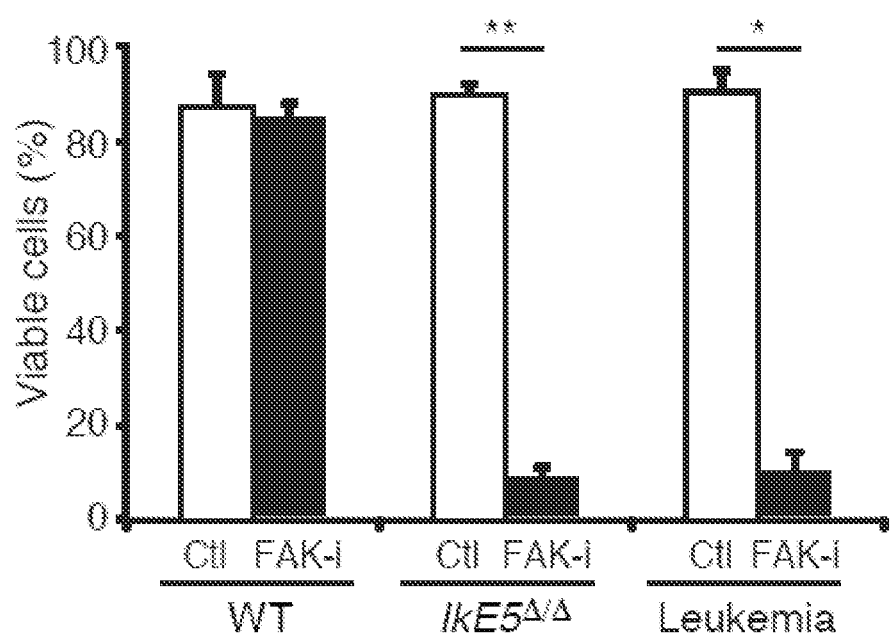

Given that the stromal-adhesion phenotype was maintained in IkE5$^{\Delta/\Delta}$ leukemic pre-B cells, the status of integrin signaling and whether these cells were sensitive to FAK inhibition in vitro was examined. Both integrin expression and FAK activation were elevated in the leukemic cells (FIG. 8c, d). Similar to the pre-leukemic mutant pre-B cells, IkE5$^{\Delta/\Delta}$ leukemic pre-B cells were highly sensitive to FAK inhibition undergoing both loss of adhesion and dramatic increase in apoptosis (FIG. 8e, f) that correlated with suppression of p-FAK (FIG. 8d). Thus, the arrest at the adherent large pre-B cell stage mediated by loss of Ikaros predisposes this population for transformation to a leukemic state, which however appears to be sensitive to inhibition of adhesion-based signaling pathways supported by FAK, thereby opening a new avenue for therapy of poor prognosis B cell precursor leukemias in humans.

Example 9

Effects of FAK Inhibition on Mouse Leukemic Samples with Ikaros Mutation

As noted above, the preB cells that accumulated in the mice that express the IkE5$^{\Delta/\Delta}$ (also referred to herein as Ikaros DN) mutant were arrested in development but non-malignant. They filled the bone marrow B-lymphoid niche but did not expand in peripheral lymphoid organs (lymph nodes or spleen) nor do they interfere with normal bone marrow myeloid or erythroid function (See Example 1, e.g., FIG. 1D). In addition, after transplantation IK6Ph+ human B-ALL cells behave the same way, i.e., they stay in the BM and do not go out in the periphery Based on the observation that Ikaros mutations are highly associated with Ph$^+$ B-ALL in humans, the hypothesis was tested that the product of the Ph chromosome, the BCR-ABL1 tyrosine kinase, could cooperate with the Ikaros DN mutation to generate a full-blown leukemia. Mouse leukemic cell samples were established by transplantation and expansion of primary Ikaros DN preB cells, prior to or after infection with a BCR-ABL1 expressing retrovirus, into NSG mice (FIG. 16). WT preB cells were also infected with the BCR-ABL1 expressing retrovirus and leukemic lines were established in a similar fashion. FAK inhibition assays with these cells were performed with the commercially available FAK inhibitors PF-562271 (also known as VS-6062) and PF-04554878 (also known as VS-6063 or defactinib).

As shown in FIGS. 17A-D and 18A-D, the strong stromal adhesion property of Ikaros DN leukemic pre-B cells detected with or without BCR-ABL1 was greatly reduced (3-4 fold) in the presence of FAK inhibitor. The VS-6062 inhibitor exhibited the most potency at the 1 micromolar range (FIGS. 17A-D and 18A-D). It is important to note that BCR-ABL1 preB cells that are WT for Ikaros show much less stromal attachment than do IKDN or even WT preB cells but in the presence of the Ikaros mutation they acquire a strong stromal adhesion phenotype, characteristic of the Ikaros loss of function. Thus the Ikaros mutation effect was dominant over the negative effect of BCR-ABL1 on cell adhesion and integrin signaling in preB cells.

PreB cell stromal adhesion is dictated by the state of Ikaros activity. However survival appeared to correlate with BCR-ABL1 kinase activity (FIGS. 19A-E and 20A-E). Although survival of both Ikaros pre-leukemic and leukemic preB cells was reduced by 2-3 fold upon FAK inhibitor treatment, the effect on preB cells harboring both IkDN and BCR-ABL1 was much smaller (20-30%). IkDN BCR-ABL1 pre-B cells after FAK inhibitor treatment lost stromal adhesion like IKDN pre-leukemic or leukemic preB cells that lack the active ABL1 kinase but survive better in culture than these latter cell types. Nevertheless, FAK inhibitor treatment significantly reduced the survival of Ikaros DN BCR-ABL1 preB cells compared to WT BCR-ABL preB cells (FIGS. 19A-E and 20A-E). Given these data, the combined effect of FAK and ABL1 kinase inhibition was examined on IKDN BCR-ABL leukemic preB cells.

Example 10

FAK and ABL1 Inhibitors are Synergistic Against Mouse Ikaros-Mutant BCR-ABL1 Leukemic Cells To test the hypothesis that inhibition of FAK and reversal of the adhesive phenotype of Ikaros-mutant BCR-ABL1$^+$ leukemic cells might increase their sensitivity to ABL1 kinase inhibitors, a leukemic cell line isolated from diseased mice was incubated on stroma in the presence of varying concentrations of a FAK inhibitor (VS-6063) and the ABL1 kinase inhibitor dasatinib. The results (FIG. 21) demonstrate the combination of dasatinib and FAK inhibitor showed a synergistic effect of killing Ikaros-mutant BCR-ABL1+ leukemic cells across a wide range of concentrations. These results support the hypothesis that combination FAKi-dasatinib therapy might be more effective at eliminating Ikaros-mutant B-ALL in vivo in mice and in patients.

Example 11

Response of Human Ikaros-Mutant B-ALL Samples to FAK Inhibition

Figure 22A:
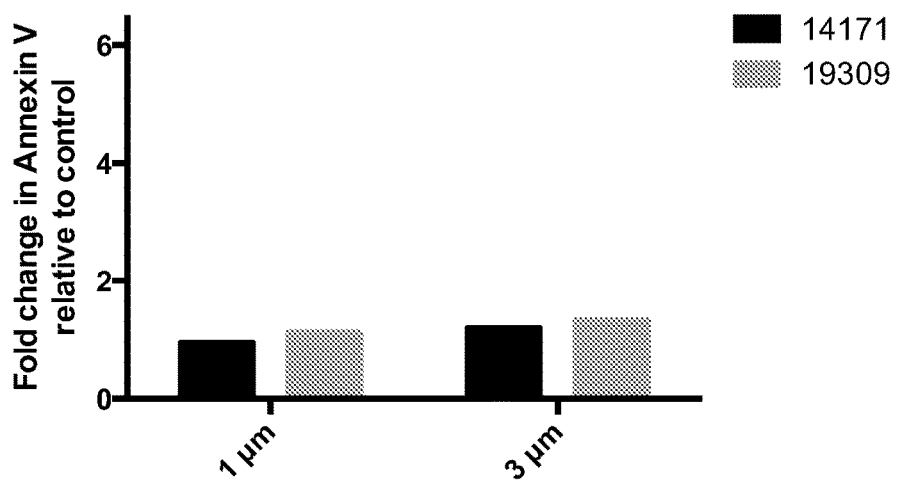
Figure 22B:
Figure 23A:
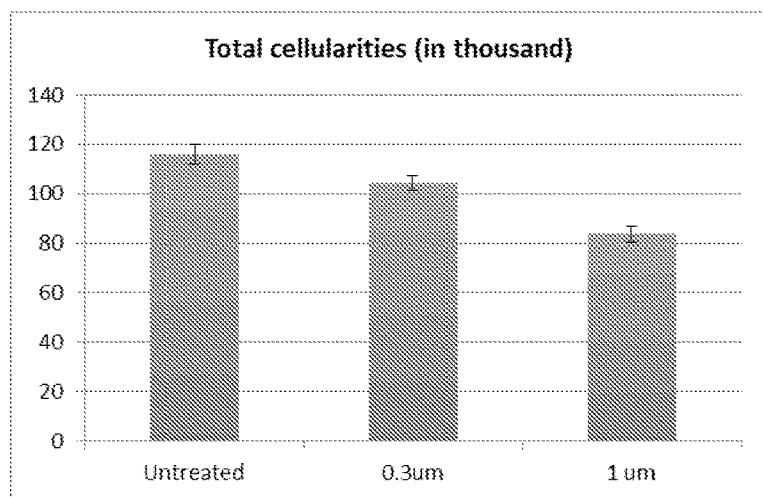
Figure 23B:
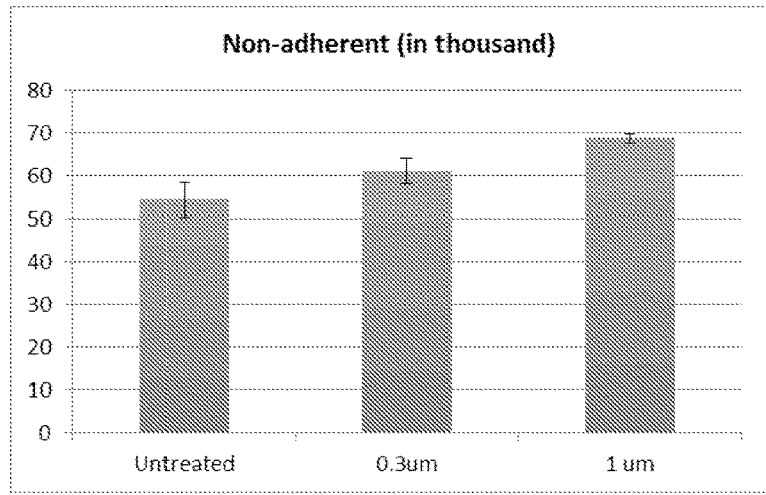
Figure 23C:
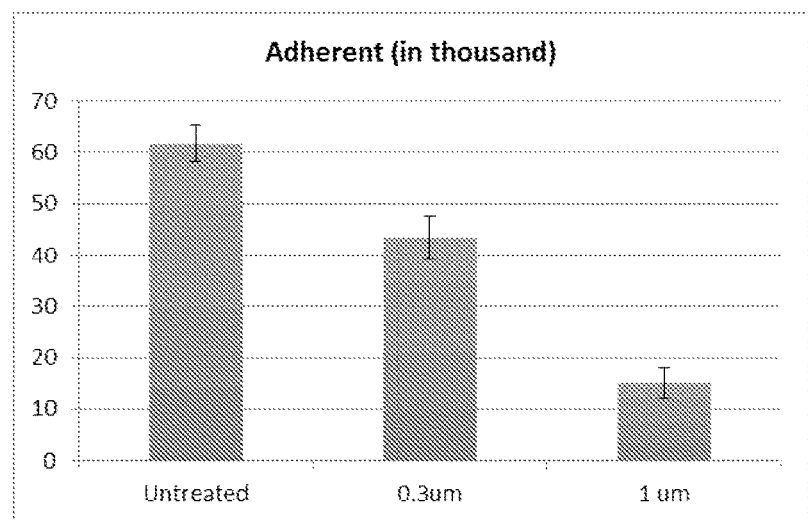

The effect of FAK inhibitors was tested on human B-ALL samples. In one experiment with two Ph+ (BCR-ABL1+) B-ALL samples without and with an Ikaros DN (Ik6) mutation (14171 and 19309 respectively) a greater increase in apoptosis (increase in Anexin V$^{+ve}$ cells) was seen with the IK6 Ph$^{+e}$ sample (19309) compared to the Ph$^{+e}$ sample (14171) that was WT for Ikaros (FIGS. 22A-B). Due to the paucity of cells in this culture, effects on adhesion could not be measured. A second human B-ALL sample with an Ikaros DN mutation that was not Ph$^{+e}$ (#128, E.P) was tested. A strong stromal adhesion phenotype was noted for these cells with a ratio of 1:1 for adherent vs. non-adherent cells (FIG. 21). Cells treated with the FAK inhibitor (vs-6062) at 1 micromolar concentration exhibited a 4-fold reduction in adhesion (FIGS. 23A-C). Notably, survival was greatly compromised in the non-adherent fraction of these cells with 2 to 3 fold increase in apoptosis (FIG. 24).

Example 12

Mechanisms of FAK Action in IKDN B-ALL; a Study in a Mouse Genetic Model

The mechanism by which FAK inhibition (FAKi) affects the survival of Ikaros-mutant preB cells was investigated. The effect of FAK inhibitor treatment on FAK-induced signaling events was first examined in the WT and Ikaros-mutant pre-leukemic preB cells. FAK p397, an autophosphorylation event used as a measure of FAK activity, was prominent in IKDN pre-leukemic cells compared to WT. In both WT and IKDN preB cells FAK pY397 was inhibited by the FAK inhibitor (vs6062 1 μM) (FIG. 25). The phosphorylation state of STAT5, a transcription factor that lies downstream of IL-7R signaling and whose phosphorylation is required for nuclear localization and activation of survival genes in WT preB cells, was also tested. Notably, pSTAT5 was decreased by FAK inhibition in the Ikaros-mutant preB cells but not in the WT preB cells (FIG. 25). These data suggest that FAK is specifically responsible for STAT5 activation in Ikaros-mutant pre-leukemic pre-B cells, possibly acting through a non-canonical pathway (FAK-JAK-STAT or FAK-STAT instead of IL7R-JAK-STAT) and supporting survival.

Whether FAK inhibition affected the global pattern of tyrosyl-phosphorylated (pTyr) proteins (tyrosine phosphoproteome) of Ikaros-mutant preB cells compared to WT was also examined. First, a difference in the overall pTyr pattern between WT and Ikaros-mutant preB cells was detected especially in the range between 75-150 kDa with strong pTyr species detected only in the IKDN pre-B cells (FIG. 26). Strikingly FAK inhibitor treatment greatly decreased the overall level of pTyr in the Ikaros-mutant cells whereas no effect on the pTyr level in WT preB cells was detected (FIG. 26), although FAK itself was inhibited as assessed by levels of pY397 (FIG. 25) in both WT and mutant. These results suggest FAK signaling is the major mediator of pTyr events and signaling in Ikaros-mutant premalignant preB cells.

The pTyr phosphorylation events that are directly dependent on FAK activity, such FAK pY397 and FAK pY925 (and pSTAT5), were ablated within 30 mins of FAK inhibitor treatment of Ikaros mutant preleukemic preB cells (FIG. 27). Phosphorylation of the ERK1/2 and AKT proteins, downstream of the MEK-MAPK and PI3K signaling pathways respectively and involved in proliferation and survival, was also affected but at a later time point (FIG. 27, 3 hrs), indicating an indirect and not direct effect of FAK inhibition. Similar to FAK phosphorylation, global pTyr levels fell rapidly, indicating that these events were directly affected by FAK.

Ikaros mutant BCR-ABL1+ leukemic pre-B cells had increased levels of activated FAK (FAK pY397), consistent with their strong phenotype of adhesion to stromal cells compared to WT BCR-ABL1+ leukemic preB cells (FIG. 28). A higher level of activated FAK (FAK pY397 and FAK pY576) was seen in Ikaros-mutant BCR-ABL1+ preB cells and was abolished by FAK inhibitor treatment. The high level of pSTAT5 detected in BCR-ABL1+ expressing preB cells was partly inhibited by FAK, although a significant level of pSTAT5 remained, likely a consequence of the kinase activity of BCR-ABL1. Similar to pSTAT5, the global level of pTyr in Ikaros-mutant BCR-ABL1+ leukemic preB cell was seen after FAK inhibitor treatment but a significant level remained.

These data indicate that FAK activation, downstream of integrin signaling activation in Ikaros-mutant preB cells, serves as a central node for a tyrosine phosphorylation network that supports the mutant preB cell interactions with the microenvironment and their survival. This process is readily reversible by FAK inhibitor treatment. Apparently, this FAK activity is still contributing to the pTyr signaling network even in the presence of activation of another strong tyrosine kinase such as BCR-ABL1, providing a strong rationale for combination treatments with FAK inhibitors and ABL1 inhibitors in Ph+ and FAK and inhibitors to other tyrosine kinases such as JAK2, which can be activated in some cases of "Ph-like" human B-ALL disease.

REFERENCES

1. Monroe, J. G. ITAM-mediated tonic signalling through pre-BCR and BCR complexes. *Nat Rev Immunol* 6, 283-294 (2006).

2. Herzog, S., Reth, M. & Jumaa, H. Regulation of B-cell proliferation and differentiation by pre-B-cell receptor signalling. *Nat Rev Immunol* 9, 195-205 (2009).

3. Gauld, S. B. & Cambier, J. C. Src-family kinases in B-cell development and signaling. *Oncogene* 23, 8001-8006 (2004).

4. Kitamura, D. et al. A critical role of lambda 5 protein in B cell development. *Cell* 69, 823-831 (1992).

5. Gong, S. & Nussenzweig, M. C. Regulation of an early developmental checkpoint in the B cell pathway by Ig beta. *Science* 272, 411-414 (1996).

6. Kraus, M. et al. Interference with immunoglobulin (Ig)alpha immunoreceptor tyrosine-based activation motif (ITAM) phosphorylation modulates or blocks B cell development, depending on the availability of an Igbeta cytoplasmic tail. *J Exp Med* 194, 455-469 (2001).

7. Pelanda, R., Braun, U., Hobeika, E., Nussenzweig, M. C. & Reth, M. B cell progenitors are arrested in maturation but have intact VDJ recombination in the absence of Ig-alpha and Ig-beta. *J Immunol* 169, 865-872 (2002).

8. Cheng, A. M. et al. Syk tyrosine kinase required for mouse viability and B-cell development. *Nature* 378, 303-306 (1995).

9. Schweighoffer, E., Vanes, L., Mathiot, A., Nakamura, T. & Tybulewicz, V. L. Unexpected requirement for ZAP-70 in pre-B cell development and allelic exclusion. *Immunity* 18, 523-533 (2003).

10. Saijo, K. et al. Essential role of Src-family protein tyrosine kinases in NF-kappaB activation during B cell development. *Nat Immunol* 4, 274-279 (2003).

11. Marshall, A. J., Fleming, H. E., Wu, G. E. & Paige, C. J. Modulation of the IL-7 dose-response threshold during pro-B cell differentiation is dependent on pre-B cell receptor expression. *J Immunol* 161, 6038-6045 (1998).

12. Fleming, H. E. & Paige, C. J. Pre-B cell receptor signaling mediates selective response to IL-7 at the pro-B to pre-B cell transition via an ERK/MAP kinase-dependent pathway. *Immunity* 15, 521-531 (2001).

13. Malin, S. et al. Role of STAT5 in controlling cell survival and immunoglobulin gene recombination during pro-B cell development. *Nat Immunol* 11, 171-179 (2010).

14. Yasuda, T. et al. Erk kinases link pre-B cell receptor signaling to transcriptional events required for early B cell expansion. *Immunity* 28, 499-508 (2008).

15. Kersseboom, R. et al. Bruton's tyrosine kinase cooperates with the B cell linker protein SLP-65 as a tumor suppressor in Pre-B cells. *J Exp Med* 198, 91-98 (2003).

16. Middendorp, S. et al. Tumor suppressor function of Bruton tyrosine kinase is independent of its catalytic activity. *Blood* 105, 259-265 (2005).

17. Wen, R. et al. Essential role of phospholipase C gamma 2 in early B-cell development and Myc-mediated lymphomagenesis. *Mol Cell Biol* 26, 9364-9376 (2006).

18. Herzog, S. et al. SLP-65 regulates immunoglobulin light chain gene recombination through the PI(3)K-PKB-Foxo pathway. *Nat Immunol* 9, 623-631 (2008).

19. Johnson, K. et al. Regulation of immunoglobulin light-chain recombination by the transcription factor IRF-4 and the attenuation of interleukin-7 signaling. *Immunity* 28, 335-345 (2008).

20. Ochiai, K. et al. A self-reinforcing regulatory network triggered by limiting IL-7 activates pre-BCR signaling and differentiation. *Nat Immunol* 13, 300-307 (2012).

21. Cobaleda, C. & Sanchez-Garcia, I. B-cell acute lymphoblastic leukaemia: towards understanding its cellular origin. *Bioessays* 31, 600-609 (2009).

22. Mullighan, C. G. et al. Genome-wide analysis of genetic alterations in acute lymphoblastic leukaemia. *Nature* 446, 758-764 (2007).

23. Mullighan, C. G. et al. Deletion of IKZF1 and Prognosis in Acute Lymphoblastic Leukemia. *N Engl J Med* (2009).

24. Iacobucci, I. et al. Expression of spliced oncogenic Ikaros isoforms in Philadelphia-positive acute lymphoblastic leukemia patients treated with tyrosine kinase inhibitors: implications for a new mechanism of resistance. *Blood* 112, 3847-3855 (2008).

25. Iacobucci, I. et al. Identification and molecular characterization of recurrent genomic deletions on 7p12 in the IKZF1 gene in a large cohort of BCR-ABL1-positive acute lymphoblastic leukemia patients: on behalf of Gruppo Italiano Malattie Ematologiche dell'Adulto Acute Leukemia Working Party (GIMEMA AL WP). *Blood* 114, 2159-2167 (2009).

26. Harvey, R. C. et al. Identification of novel cluster groups in pediatric high-risk B-precursor acute lymphoblastic leukemia with gene expression profiling: correlation with genome-wide DNA copy number alterations, clinical characteristics, and outcome. *Blood* (2010).

27. Georgopoulos, K. Acute Lymphoblastic Leukemia—On the Wings of IKAROS. *N Engl J Med* (2009).

28. Georgopoulos, K. et al. The Ikaros gene is required for the development of all lymphoid lineages. *Cell* 79, 143-156 (1994).

29. Ng, S. Y., Yoshida, T., Zhang, J. & Georgopoulos, K. Genome-wide lineage-specific transcriptional networks underscore Ikaros-dependent lymphoid priming in hematopoietic stem cells. *Immunity* 30, 493-507 (2009).

30. Morgan, B. et al. Aiolos, a lymphoid restricted transcription factor that interacts with Ikaros to regulate lymphocyte differentiation. *Embo J* 16, 2004-2013 (1997).

31. Thompson, E. C. et al. Ikaros DNA-binding proteins as integral components of B cell developmental-stage-specific regulatory circuits. *Immunity* 26, 335-344 (2007).

32. Sun, L., Liu, A. & Georgopoulos, K. Zinc finger-mediated protein interactions modulate Ikaros activity, a molecular control of lymphocyte development. *Embo J* 15, 5358-5369 (1996).

33. Pelanda, R., Schaal, S., Torres, R. M. & Rajewsky, K. A prematurely expressed Ig(kappa) transgene, but not V(kappa)J(kappa) gene segment targeted into the Ig(kappa) locus, can rescue B cell development in lambda5-deficient mice. *Immunity* 5, 229-239 (1996).

34. Rolink, A. G., Winkler, T., Melchers, F. & Andersson, J. Precursor B cell receptor-dependent B cell proliferation and differentiation does not require the bone marrow or fetal liver environment. *J Exp Med* 191, 23-32 (2000).

35. Kierney, P. C. & Dorshkind, K. B lymphocyte precursors and myeloid progenitors survive in diffusion chamber cultures but B cell differentiation requires close association with stromal cells. *Blood* 70, 1418-1424 (1987).

36. Hayashi, S. et al. Stepwise progression of B lineage differentiation supported by interleukin 7 and other stromal cell molecules. *J Exp Med* 171, 1683-1695 (1990).

37. Glodek, A. M. et al. Focal adhesion kinase is required for CXCL12-induced chemotactic and pro-adhesive responses in hematopoietic precursor cells. *Leukemia* 21, 1723-1732 (2007).

38. Tse, K. W. et al. B cell receptor-induced phosphorylation of Pyk2 and focal adhesion kinase involves integrins and the Rap GTPases and is required for B cell spreading. *J Biol Chem* 284, 22865-22877 (2009).

39. Rolink, A., Streb, M., Nishikawa, S. & Melchers, F. The c-kit-encoded tyrosine kinase regulates the proliferation of early pre-B cells. *Eur J Immunol* 21, 2609-2612 (1991).

40. Sudo, T. et al. Expression and function of the interleukin 7 receptor in murine lymphocytes. *Proceedings of the National Academy of Sciences of the United States of America* 90, 9125-9129 (1993).

41. Winandy, S., Wu, P. & Georgopoulos, K. A dominant mutation in the Ikaros gene leads to rapid development of leukemia and lymphoma. *Cell* 83, 289-299 (1995).

42. Ye, F., Kim, C. & Ginsberg, M. H. Reconstruction of integrin activation. *Blood* 119, 26-33 (2012).

43. Wehrle-Haller, B. Structure and function of focal adhesions. *Curr Opin Cell Biol* 24, 116-124 (2012).

44. Galbraith, C. G., Yamada, K. M. & Galbraith, J. A. Polymerizing actin fibers position integrins primed to probe for adhesion sites. *Science* 315, 992-995 (2007).

45. Vicente-Manzanares, M., Choi, C. K. & Horwitz, A. R. Integrins in cell migration—the actin connection. *J Cell Sci* 122, 199-206 (2009).

46. Smith, A. et al. A talin-dependent LFA-1 focal zone is formed by rapidly migrating T lymphocytes. *J Cell Biol* 170, 141-151 (2005).

47. Choi, C. K. et al. Actin and alpha-actinin orchestrate the assembly and maturation of nascent adhesions in a myosin II motor-independent manner. *Nature cell biology* 10, 1039-1050 (2008).

48. Heasman, S. J. & Ridley, A. J. Mammalian Rho GTPases: new insights into their functions from in vivo studies. *Nat Rev Mol Cell Biol* 9, 690-701 (2008).

49. Park, S. Y. et al. Focal adhesion kinase regulates the localization and retention of pro-B cells in bone marrow microenvironments. *J Immunol* 190, 1094-1102 (2013).

53. Fuxa, M. et al. Pax5 induces V-to-DJ rearrangements and locus contraction of the immunoglobulin heavy-chain gene. *Genes Dev* 18, 411-422 (2004).

54. Osmond, D. G., Melchers, F. & Paige, C. J. Pre-B cells in mouse bone marrow: in vitro maturation of peanut agglutinin binding B lymphocyte precursors separated from bone marrow by fluorescence-activated cell sorting. *J Immunol* 133, 86-90 (1984).

55. Bernardi, P., Patel, V. P. & Lodish, H. F. Lymphoid precursor cells adhere to two different sites on fibronectin. *J Cell Biol* 105, 489-498 (1987).

56. Roumiantsev, S., de Aos, I. E., Varticovski, L., Ilaria, R. L. & Van Etten, R. A. The src homology 2 domain of Bcr/Abl is required for efficient induction of chronic myeloid leukemia-like disease in mice but not for lymphoid leukemogenesis or activation of phosphatidylinositol 3-kinase. *Blood* 97, 4-13 (2001)

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

```
                        SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: synthetic adhesion-blocking peptide

<400> SEQUENCE: 1

Gly Arg Gly Asp Ser Pro
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic control peptide

<400> SEQUENCE: 2

Gly Arg Gly Glu Ser
1               5
```

50. Waanders, E. et al. Integrated use of minimal residual disease classification and IKZF1 alteration status accurately predicts 79% of relapses in pediatric acute lymphoblastic leukemia. *Leukemia* 25, 254-258 (2011).

51. Yoshida, T., Ng, S. Y., Zuniga-Pflucker, J. C. & Georgopoulos, K. Early hematopoietic lineage restrictions directed by Ikaros. *Nat Immunol* 7, 382-391 (2006).

52. Schlissel, M. S., Corcoran, L. M. & Baltimore, D. Virus-transformed pre-B cells show ordered activation but not inactivation of immunoglobulin gene rearrangement and transcription. *J Exp Med* 173, 711-720 (1991).

What is claimed is:

1. A method of treating a subject who has B cell acute lymphoblastic leukemia (B-ALL), comprising:

(i) identifying a subject comprising leukemic cells having a mutation in IKZF1, wherein the mutation results in haploinsufficiency or expression of a dominant negative form of Ikaros and/or in hyperactivation of FAK activity; and (ii) administering a therapeutically effective amount of VS-4718 and dasatinib to the subject.

2. The method of claim 1, further comprising selecting the subject for treatment comprising:
- obtaining a sample from the subject comprising B cells that are known or suspected to be leukemic; and
- (i) performing an assay to determine a level of FAK activity in the sample;
- comparing the level of FAK activity in the sample to a reference level of FAK activity;
- identifying a subject as having cells with a level of FAK activity that is above the reference level; or
- (ii) performing an assay to detect the presence or absence of a mutation in IKZF1 in the cells;
- identifying a subject as having cells with a mutation in IKZF1; and
- selecting the identified subject for treatment with an inhibitor of FAK.

3. The method of claim 2, wherein performing an assay to determine a level of FAK activity in the sample comprises determining a level of phosphorylated FAK in the subject.

4. The method of claim 2, wherein the mutation in IKZF1 results in haploinsufficiency or expression of a dominant-negative isoform of Ikaros.

5. The method of claim 2, wherein the mutation in IKZF1 results in hyperactivation of FAK activity.

6. The method of claim 2, wherein the subject has been diagnosed with B-ALL.

7. The method of claim 2, wherein the subject has not been diagnosed with B-ALL.

8. The method of claim 2, wherein the sample comprises peripheral blood B cells.

9. The method of claim 2, wherein the sample comprises bone marrow B cells.

* * * * *